US011633596B2

(12) United States Patent
Schwarz et al.

(10) Patent No.: US 11,633,596 B2
(45) Date of Patent: Apr. 25, 2023

(54) DEVICE AND METHOD FOR UNATTENDED TREATMENT OF A PATIENT

(71) Applicant: BTL Healthcare Technologies A.S., Prague (CZ)

(72) Inventors: Tomás Schwarz, Prague (CZ); Lucia Jelínková, Prague (CZ); Vojtech Kubík, Brevnov (CZ)

(73) Assignee: BTL Healthcare Technologies A.S., Prague (CZ)

( * ) Notice: Subject to any disclaimer, the term of this patent is extended or adjusted under 35 U.S.C. 154(b) by 0 days.

(21) Appl. No.: 17/941,777

(22) Filed: Sep. 9, 2022

(65) Prior Publication Data

US 2023/0027939 A1    Jan. 26, 2023

Related U.S. Application Data

(63) Continuation of application No. 17/664,161, filed on May 19, 2022, which is a continuation-in-part of (Continued)

(51) Int. Cl.
*A61N 1/04* (2006.01)
*A61N 1/36* (2006.01)
(Continued)

(52) U.S. Cl.
CPC ....... *A61N 1/36034* (2017.08); *A61N 1/0452* (2013.01); *A61N 1/0492* (2013.01);
(Continued)

(58) Field of Classification Search
CPC ........... A61N 1/0452; A61N 1/0492; A61N 1/36034; A61N 5/0616; A61N 2005/0642; A61N 2007/0008; A61N 2007/0034
See application file for complete search history.

(56) References Cited

U.S. PATENT DOCUMENTS 1,973,387 A    9/1934  Neymann et al.
2,021,676 A    11/1935 Wood et al.
(Continued)

FOREIGN PATENT DOCUMENTS

AU    747678 B2     5/2002
AU    2011265424 B2 7/2014
(Continued)

OTHER PUBLICATIONS

US 10,398,895, 9/2019, Tomas (withdrawn)
(Continued)

*Primary Examiner* — Mark R Gaworecki
(74) *Attorney, Agent, or Firm* — Sterne, Kessler, Goldstein & Fox P.L.L.C.

(57) ABSTRACT

An unattended approach can increase the reproducibility and safety of the treatment as the chance of over/under treating of a certain area is significantly decreased. On the other hand, unattended treatment of uneven or rugged areas can be challenging in terms of maintaining proper distance or contact with the treated tissue, mostly on areas which tend to differ from patient to patient (e.g. facial area). Delivering energy via a system of active elements embedded in a flexible pad adhesively attached to the skin offers a possible solution. The unattended approach may include delivering of multiple energies to enhance a visual appearance.

28 Claims, 14 Drawing Sheets

Related U.S. Application Data application No. 17/518,243, filed on Nov. 3, 2021, which is a continuation-in-part of application No. PCT/IB2021/000300, filed on May 3, 2021.

(60) Provisional application No. 63/019,619, filed on May 4, 2020.

(51) Int. Cl.
*A61N 5/06* (2006.01)
*A61N 7/00* (2006.01)

(52) U.S. Cl.
CPC .... *A61N 5/0616* (2013.01); *A61N 2005/0642* (2013.01); *A61N 2007/0008* (2013.01); *A61N 2007/0034* (2013.01)

(56) References Cited

U.S. PATENT DOCUMENTS

| | | |
|---|---|---|
| 3,163,161 A | 12/1964 | Jacques et al. |
| 3,566,877 A | 3/1971 | Smith et al. |
| 3,658,051 A | 4/1972 | Maclean et al. |
| 3,841,306 A | 10/1974 | Hallgren et al. |
| 3,915,151 A | 10/1975 | Kraus |
| 3,946,349 A | 3/1976 | Haldeman, III |
| 3,952,751 A | 4/1976 | Yarger |
| 3,971,387 A | 7/1976 | Mantell |
| 4,068,292 A | 1/1978 | Berry et al. |
| 4,143,661 A | 3/1979 | LaForge et al. |
| 4,197,851 A | 4/1980 | Fellus |
| 4,237,898 A | 12/1980 | Whalley |
| 4,305,115 A | 12/1981 | Armitage |
| 4,315,503 A | 2/1982 | Ryaby et al. |
| 4,392,040 A | 7/1983 | Rand et al. |
| 4,454,883 A | 6/1984 | Fellus |
| 4,456,001 A | 6/1984 | Pescatore |
| 4,550,714 A | 11/1985 | Talish et al. |
| 4,556,056 A | 12/1985 | Fischer et al. |
| 4,665,898 A | 5/1987 | Costa et al. |
| 4,674,482 A | 6/1987 | Waltonen et al. |
| 4,674,505 A | 6/1987 | Pauli et al. |
| 4,723,536 A | 2/1988 | Rauscher et al. |
| 4,850,959 A | 7/1989 | Findl |
| 4,889,526 A | 12/1989 | Rauscher et al. |
| 4,957,480 A | 9/1990 | Morenings |
| 4,989,604 A | 2/1991 | Fang |
| 4,993,413 A | 2/1991 | McLeod et al. |
| 5,061,234 A | 10/1991 | Chaney |
| 5,067,940 A | 11/1991 | Liboff et al. |
| 5,085,626 A | 2/1992 | Frey |
| 5,143,063 A | 9/1992 | Fellner |
| 5,156,587 A | 10/1992 | Montone |
| 5,181,902 A | 1/1993 | Erickson et al. |
| 5,199,951 A | 4/1993 | Spears |
| 5,334,181 A | 8/1994 | Rubinsky et al. |
| 5,344,384 A | 9/1994 | Ostrow et al. |
| 5,401,233 A | 3/1995 | Erickson et al. |
| 5,415,617 A | 5/1995 | Kraus |
| 5,419,344 A | 5/1995 | Dewitt |
| 5,433,737 A | 7/1995 | Aimone |
| 5,433,740 A | 7/1995 | Yamaguchi |
| 5,584,863 A | 12/1996 | Rauch et al. |
| 5,620,463 A | 4/1997 | Drolet |
| 5,660,836 A | 8/1997 | Knowlton |
| 5,674,218 A | 10/1997 | Rubinsky et al. |
| 5,690,692 A | 11/1997 | Fleming |
| 5,691,873 A | 11/1997 | Masaki |
| 5,718,662 A | 2/1998 | Jalinous |
| 5,725,471 A | 3/1998 | Davey et al. |
| 5,755,753 A | 5/1998 | Knowlton |
| 5,766,124 A | 6/1998 | Polson |
| 5,782,743 A | 7/1998 | Russell |
| 5,807,232 A | 9/1998 | Espinoza et al. |
| 5,857,957 A | 1/1999 | Lin |
| 5,908,444 A | 6/1999 | Azure |
| 5,919,219 A | 7/1999 | Knowlton |
| 5,968,527 A | 10/1999 | Litovitz |
| 5,984,854 A | 11/1999 | Ishikawa et al. |
| 6,017,337 A | 1/2000 | Pira |
| 6,032,675 A | 3/2000 | Rubinsky |
| 6,038,485 A | 3/2000 | Axelgaard |
| 6,047,215 A | 4/2000 | McClure et al. |
| 6,063,108 A | 5/2000 | Salansky et al. |
| 6,067,474 A | 5/2000 | Schulman et al. |
| 6,086,525 A | 7/2000 | Davey et al. |
| 6,094,599 A | 7/2000 | Bingham et al. |
| 6,099,459 A | 8/2000 | Jacobson |
| 6,099,523 A | 8/2000 | Kim et al. |
| 6,117,066 A | 9/2000 | Abrams et al. |
| 6,132,361 A | 10/2000 | Epstein et al. |
| 6,141,985 A | 11/2000 | Cluzeau et al. |
| 6,155,966 A | 12/2000 | Parker |
| 6,161,757 A | 12/2000 | Morris |
| 6,179,769 B1 | 1/2001 | Ishikawa et al. |
| 6,179,770 B1 | 1/2001 | Mould |
| 6,179,771 B1 | 1/2001 | Mueller |
| 6,200,259 B1 | 3/2001 | March |
| 6,213,933 B1 | 4/2001 | Lin |
| 6,223,750 B1 | 5/2001 | Ishikawa et al. |
| 6,246,905 B1 | 6/2001 | Mogul |
| 6,255,815 B1 | 7/2001 | Davey |
| 6,261,301 B1 | 7/2001 | Knesch et al. |
| 6,273,862 B1 | 8/2001 | Privitera et al. |
| 6,273,884 B1 | 8/2001 | Altshuler et al. |
| 6,280,376 B1 | 8/2001 | Holcomb |
| 6,282,448 B1 | 8/2001 | Katz et al. |
| D447,806 S | 9/2001 | Davey et al. |
| 6,311,090 B1 | 10/2001 | Knowlton |
| 6,324,430 B1 | 11/2001 | Zarinetchi et al. |
| 6,324,432 B1 | 11/2001 | Rigaux et al. |
| 6,334,069 B1 | 12/2001 | George et al. |
| 6,334,074 B1 | 12/2001 | Spertell |
| 6,350,276 B1 | 2/2002 | Knowlton |
| 6,402,678 B1 | 6/2002 | Fischell et al. |
| 6,413,255 B1 | 7/2002 | Stern |
| 6,418,345 B1 | 7/2002 | Tepper et al. |
| 6,424,864 B1 | 7/2002 | Matsuura |
| 6,425,852 B1 | 7/2002 | Epstein et al. |
| 6,443,883 B1 | 9/2002 | Ostrow et al. |
| 6,445,955 B1 | 9/2002 | Michelson et al. |
| 6,447,440 B1 | 9/2002 | Markoll |
| 6,453,202 B1 | 9/2002 | Knowlton |
| 6,461,375 B1 | 10/2002 | Baudry et al. |
| 6,491,620 B1 | 12/2002 | Davey |
| 6,500,110 B1 | 12/2002 | Davey et al. |
| 6,520,903 B1 | 2/2003 | Yamashiro |
| 6,527,694 B1 | 3/2003 | Ishikawa et al. |
| 6,527,695 B1 | 3/2003 | Davey et al. |
| 6,537,197 B1 | 3/2003 | Ruohonen et al. |
| 6,569,078 B2 | 5/2003 | Ishikawa et al. |
| 6,605,080 B1 | 8/2003 | Altshuler et al. |
| 6,635,053 B1 | 10/2003 | Lalonde et al. |
| 6,658,301 B2 | 12/2003 | Loeb et al. |
| 6,662,054 B2 | 12/2003 | Kreindel et al. |
| 6,663,556 B2 | 12/2003 | Barker |
| 6,663,659 B2 | 12/2003 | McDaniel |
| 6,701,185 B2 | 3/2004 | Burnett et al. |
| 6,735,481 B1 | 5/2004 | Bingham et al. |
| 6,738,667 B2 | 5/2004 | Deno et al. |
| 6,749,624 B2 | 6/2004 | Knowlton |
| 6,827,681 B2 | 12/2004 | Tanner et al. |
| 6,849,040 B2 | 2/2005 | Ruohonen et al. |
| 6,860,852 B2 | 3/2005 | Schonenberger et al. |
| 6,871,099 B1 | 3/2005 | Whitehurst et al. |
| 6,879,859 B1 | 4/2005 | Boveja |
| 6,889,090 B2 | 5/2005 | Kreindel |
| 6,920,883 B2 | 7/2005 | Bessette et al. |
| 6,939,287 B1 | 9/2005 | Ardizzone et al. |
| 6,960,202 B2 | 11/2005 | Cluzeau et al. |
| 6,990,427 B2 | 1/2006 | Kirsch et al. |
| 7,024,239 B2 | 4/2006 | George et al. |
| 7,030,764 B2 | 4/2006 | Smith et al. |
| 7,041,100 B2 | 5/2006 | Kreindel |
| 7,083,580 B2 | 8/2006 | Bernabei |

(56) References Cited

U.S. PATENT DOCUMENTS

| | | |
|---|---|---|
| 7,186,209 B2 | 3/2007 | Jacobson et al. |
| 7,217,265 B2 | 5/2007 | Hennings et al. |
| 7,276,058 B2 | 10/2007 | Altshuler et al. |
| 7,309,309 B2 | 12/2007 | Wang et al. |
| 7,318,821 B2 | 1/2008 | Lalonde et al. |
| 7,351,252 B2 | 4/2008 | Altshuler et al. |
| 7,367,341 B2 | 5/2008 | Anderson et al. |
| 7,369,895 B2 | 5/2008 | Hurtado |
| 7,372,271 B2 | 5/2008 | Roozen et al. |
| 7,376,460 B2 | 5/2008 | Bernabei |
| 7,396,326 B2 | 7/2008 | Ghiron et al. |
| 7,496,401 B2 | 2/2009 | Bernabei |
| 7,520,849 B1 | 4/2009 | Simon |
| 7,520,875 B2 | 4/2009 | Bernabei |
| 7,532,926 B2 | 5/2009 | Bernabei |
| 7,571,003 B2 | 8/2009 | Pozzato |
| 7,591,776 B2 | 9/2009 | Phillips et al. |
| 7,601,115 B2 | 10/2009 | Riehl |
| 7,608,035 B2 | 10/2009 | Farone |
| 7,618,429 B2 | 11/2009 | Mulholland |
| 7,630,774 B2 | 12/2009 | Karni et al. |
| 7,643,883 B2 | 1/2010 | Kreindel |
| 7,697,998 B2 | 4/2010 | Axelgaard |
| 7,699,768 B2 | 4/2010 | Kishawi et al. |
| 7,740,574 B2 | 6/2010 | Pilla et al. |
| 7,744,523 B2 | 6/2010 | Epstein |
| 7,783,348 B2 | 8/2010 | Gill et al. |
| 7,785,358 B2 | 8/2010 | Lach |
| 7,854,754 B2 | 12/2010 | Ting et al. |
| 7,909,786 B2 | 3/2011 | Bonnefin et al. |
| 7,914,469 B2 | 3/2011 | Torbati |
| 7,945,321 B2 | 5/2011 | Bernabei |
| 7,946,973 B2 | 5/2011 | Peterchev |
| 7,953,500 B2 | 5/2011 | Bingham et al. |
| 7,998,053 B2 | 8/2011 | Aho |
| 8,035,385 B2 | 10/2011 | Tomiha et al. |
| RE43,007 E | 12/2011 | Lalonde et al. |
| 8,088,058 B2 | 1/2012 | Juliana et al. |
| 8,128,549 B2 | 3/2012 | Testani et al. |
| 8,133,191 B2 | 3/2012 | Rosenberg et al. |
| 8,137,258 B1 | 3/2012 | Dennis et al. |
| 8,172,835 B2 | 5/2012 | Leyh et al. |
| 8,192,474 B2 | 6/2012 | Levinson |
| 8,204,446 B2 | 6/2012 | Scheer et al. |
| 8,251,986 B2 | 8/2012 | Chornenky et al. |
| 8,265,763 B2 | 9/2012 | Fahey |
| 8,271,090 B1 | 9/2012 | Hartman et al. |
| 8,275,442 B2 | 9/2012 | Allison |
| 8,285,390 B2 | 10/2012 | Levinson et al. |
| 8,335,566 B2 | 12/2012 | Muller et al. |
| 8,337,539 B2 | 12/2012 | Ting et al. |
| 8,366,756 B2 | 2/2013 | Tucek et al. |
| 8,376,825 B2 | 2/2013 | Guinn et al. |
| 8,376,925 B1 | 2/2013 | Dennis et al. |
| 8,454,591 B2 | 6/2013 | Leyh et al. |
| 8,457,751 B2 | 6/2013 | Pozzato |
| 8,475,354 B2 | 7/2013 | Phillips et al. |
| 8,493,286 B1 | 7/2013 | Agrama |
| 8,523,927 B2 | 9/2013 | Levinson et al. |
| 8,548,599 B2 | 10/2013 | Zarsky et al. |
| 8,565,888 B2 | 10/2013 | Buhlmann et al. |
| 8,579,953 B1 | 11/2013 | Dunbar et al. |
| 8,588,930 B2 | 11/2013 | DiUbaldi et al. |
| 8,593,245 B2 | 11/2013 | Zeng et al. |
| 8,603,073 B2 | 12/2013 | Allison |
| 8,646,239 B2 | 2/2014 | Rulon |
| 8,666,492 B2 | 3/2014 | Muller et al. |
| 8,676,338 B2 | 3/2014 | Levinson |
| 8,684,901 B1 | 4/2014 | Zabara |
| 8,700,176 B2 | 4/2014 | Azar et al. |
| 8,702,774 B2 | 4/2014 | Baker et al. |
| 8,725,270 B2 | 5/2014 | Towe |
| 8,771,326 B2 | 7/2014 | Myeong et al. |
| 8,788,060 B2 | 7/2014 | Nebrigic et al. |
| 8,795,148 B2 | 8/2014 | Schneider et al. |
| 8,834,547 B2 | 9/2014 | Anderson et al. |
| 8,840,608 B2 | 9/2014 | Anderson et al. |
| 8,864,641 B2 | 10/2014 | Riehl et al. |
| 8,868,177 B2 | 10/2014 | Simon et al. |
| 8,906,009 B2 | 12/2014 | Nebrigic et al. |
| 8,915,948 B2 | 12/2014 | Altshuler et al. |
| 8,932,338 B2 | 1/2015 | Lim et al. |
| 8,979,727 B2 | 3/2015 | Ron et al. |
| 8,985,331 B2 | 3/2015 | Guenter et al. |
| 8,998,791 B2 | 4/2015 | Ron Edoute et al. |
| 9,002,477 B2 | 4/2015 | Burnett |
| 9,008,793 B1 | 4/2015 | Cosman, Sr. et al. |
| 9,028,469 B2 | 5/2015 | Jones et al. |
| 9,037,247 B2 | 5/2015 | Simon et al. |
| 9,044,595 B2 | 6/2015 | Araya et al. |
| 9,061,128 B2 | 6/2015 | Hall et al. |
| 9,072,891 B1 | 7/2015 | Rao |
| 9,078,634 B2 | 7/2015 | Gonzales et al. |
| 9,089,719 B2 | 7/2015 | Simon et al. |
| 9,101,524 B2 | 8/2015 | Aghion |
| 9,132,031 B2 | 9/2015 | Levinson et al. |
| 9,149,650 B2 | 10/2015 | Shanks et al. |
| 9,168,096 B2 | 10/2015 | Kreindel |
| 9,233,257 B1 | 1/2016 | Zabara |
| 9,254,395 B1 | 2/2016 | Shambayati |
| 9,261,574 B2 | 2/2016 | Boskamp et al. |
| 9,265,690 B2 | 2/2016 | Kriksunov et al. |
| 9,308,120 B2 | 4/2016 | Anderson et al. |
| 9,314,368 B2 | 4/2016 | Allison et al. |
| 9,326,910 B2 | 5/2016 | Eckhouse et al. |
| 9,339,641 B2 | 5/2016 | Rajguru et al. |
| 9,358,068 B2 | 6/2016 | Schomacker et al. |
| 9,358,149 B2 | 6/2016 | Anderson et al. |
| 9,375,345 B2 | 6/2016 | Levinson et al. |
| 9,387,339 B2 | 7/2016 | Sham et al. |
| 9,398,975 B2 | 7/2016 | Moller et al. |
| 9,408,745 B2 | 8/2016 | Levinson et al. |
| 9,414,759 B2 | 8/2016 | Lang et al. |
| 9,433,797 B2 | 9/2016 | Pilla et al. |
| 9,439,805 B2 | 9/2016 | Gonzales et al. |
| 9,446,258 B1 | 9/2016 | Schwarz |
| 9,468,774 B2 | 10/2016 | Arsk et al. |
| 9,532,832 B2 | 1/2017 | Ron Edoute et al. |
| 9,545,523 B2 | 1/2017 | Nanda |
| 9,561,357 B2 | 2/2017 | Hall et al. |
| 9,586,057 B2 | 3/2017 | Ladman et al. |
| 9,596,920 B2 | 3/2017 | Shalev et al. |
| 9,610,429 B2 | 4/2017 | Harris et al. |
| 9,610,459 B2 | 4/2017 | Burnett et al. |
| 9,615,854 B2 | 4/2017 | Matsushita |
| 9,636,516 B2 | 5/2017 | Schwarz |
| 9,636,519 B2 | 5/2017 | Ladman et al. |
| 9,649,220 B2 | 5/2017 | Anderson et al. |
| 9,655,770 B2 | 5/2017 | Levinson et al. |
| 9,694,194 B2 | 7/2017 | Ron Edoute et al. |
| 9,737,238 B2 | 8/2017 | Wright et al. |
| 9,737,434 B2 | 8/2017 | Allison |
| 9,757,584 B2 | 9/2017 | Burnett |
| 9,782,324 B2 | 10/2017 | Crunick et al. |
| 9,814,897 B2 | 11/2017 | Ron Edoute et al. |
| 9,844,460 B2 | 12/2017 | Weber et al. |
| 9,844,461 B2 | 12/2017 | Levinson et al. |
| 9,855,166 B2 | 1/2018 | Anderson et al. |
| 9,861,421 B2 | 1/2018 | O'Neil et al. |
| 9,861,520 B2 | 1/2018 | Baker et al. |
| 9,867,996 B2 | 1/2018 | Zarsky et al. |
| 9,901,743 B2 | 2/2018 | Ron Edoute et al. |
| 9,919,161 B2 | 3/2018 | Schwarz |
| 9,937,358 B2 | 4/2018 | Schwarz |
| 9,962,553 B2 | 5/2018 | Schwarz et al. |
| 9,968,797 B2 | 5/2018 | Sham et al. |
| 9,974,519 B1 | 5/2018 | Schwarz |
| 9,974,684 B2 | 5/2018 | Anderson et al. |
| 9,980,765 B2 | 5/2018 | Avram et al. |
| 9,981,143 B2 | 5/2018 | Ron Edoute et al. |
| 9,999,780 B2 | 6/2018 | Weyh et al. |
| 10,037,867 B2 | 7/2018 | Godyak |
| 10,039,929 B1 | 8/2018 | Schwarz et al. |
| 10,080,906 B2 | 9/2018 | Schwarz |

(56) References Cited

U.S. PATENT DOCUMENTS

| | | |
|---|---|---|
| 10,092,346 B2 | 10/2018 | Levinson |
| 10,111,770 B2 | 10/2018 | Harris et al. |
| 10,111,774 B2 | 10/2018 | Gonzales et al. |
| 10,124,187 B2 | 11/2018 | Schwarz et al. |
| 10,183,172 B2 | 1/2019 | Ghiron et al. |
| 10,195,453 B2 | 2/2019 | Schwarz et al. |
| 10,195,454 B2 | 2/2019 | Yamashiro |
| 10,201,380 B2 | 2/2019 | Debenedictis et al. |
| 10,245,439 B1 | 4/2019 | Schwarz et al. |
| 10,271,900 B2 | 4/2019 | Marchitto et al. |
| 10,342,988 B2 | 7/2019 | Midorikawa et al. |
| 10,413,745 B2 | 9/2019 | Riehl |
| 10,463,869 B2 | 11/2019 | Ron Edoute et al. |
| 10,471,269 B1 | 11/2019 | Schwarz et al. |
| 10,478,588 B2 | 11/2019 | Walpole et al. |
| 10,478,633 B2 | 11/2019 | Schwarz et al. |
| 10,478,634 B2 | 11/2019 | Schwarz et al. |
| 10,493,293 B2 | 12/2019 | Schwarz et al. |
| 10,518,098 B2 | 12/2019 | Hong et al. |
| 10,549,109 B2 | 2/2020 | Schwarz et al. |
| 10,549,110 B1 | 2/2020 | Schwarz et al. |
| 10,556,121 B2 | 2/2020 | Gurfein |
| 10,556,122 B1 | 2/2020 | Schwarz et al. |
| 10,569,094 B2 | 2/2020 | Schwarz et al. |
| 10,569,095 B1 | 2/2020 | Schwarz et al. |
| 10,583,287 B2 | 3/2020 | Schwarz |
| 10,596,386 B2 | 3/2020 | Schwarz et al. |
| 10,610,696 B1 | 4/2020 | Peled |
| 10,632,321 B2 | 4/2020 | Schwarz et al. |
| 10,639,490 B2 | 5/2020 | Simon et al. |
| 10,675,819 B2 | 6/2020 | Li et al. |
| 10,688,310 B2 | 6/2020 | Schwarz et al. |
| 10,695,575 B1 | 6/2020 | Schwarz et al. |
| 10,695,576 B2 | 6/2020 | Schwarz et al. |
| 10,709,894 B2 | 7/2020 | Schwarz et al. |
| 10,709,895 B2 | 7/2020 | Schwarz et al. |
| 10,806,943 B2 | 10/2020 | Sokolowski |
| 10,821,295 B1 | 11/2020 | Schwarz et al. |
| 10,849,784 B2 | 12/2020 | Jurna et al. |
| 11,141,219 B1 | 10/2021 | Schwarz |
| 11,185,690 B2 | 11/2021 | Schwarz |
| 11,247,039 B2 | 2/2022 | Schwarz |
| 2001/0018547 A1 | 8/2001 | Mechlenburg et al. |
| 2002/0128686 A1 | 9/2002 | Minogue et al. |
| 2002/0143365 A1 | 10/2002 | Herbst |
| 2003/0032900 A1 | 2/2003 | Ella |
| 2003/0078646 A1 | 4/2003 | Axelgaard |
| 2003/0093133 A1 | 5/2003 | Crowe et al. |
| 2003/0216729 A1 | 11/2003 | Marchitto et al. |
| 2004/0034346 A1 | 2/2004 | Stern et al. |
| 2004/0039279 A1 | 2/2004 | Ruohonen |
| 2004/0077977 A1 | 4/2004 | Ella et al. |
| 2004/0210282 A1 | 10/2004 | Flock et al. |
| 2005/0038313 A1 | 2/2005 | Ardizzone |
| 2005/0107656 A1 | 5/2005 | Jang et al. |
| 2005/0187599 A1 | 8/2005 | Sharkey et al. |
| 2006/0094924 A1 | 5/2006 | Riehl |
| 2006/0293719 A1 | 12/2006 | Naghavi |
| 2007/0016274 A1 | 1/2007 | Boveja et al. |
| 2007/0027411 A1 | 2/2007 | Ella et al. |
| 2007/0088419 A1 | 4/2007 | Fiorina et al. |
| 2007/0142886 A1 | 6/2007 | Fischell et al. |
| 2007/0179534 A1 | 8/2007 | Firlik et al. |
| 2007/0293918 A1 | 12/2007 | Thompson et al. |
| 2008/0046053 A1 | 2/2008 | Wagner et al. |
| 2008/0082153 A1 | 4/2008 | Gadsby et al. |
| 2009/0099405 A1 | 4/2009 | Schneider et al. |
| 2009/0118790 A1 | 5/2009 | Van Herk |
| 2009/0270945 A1 | 10/2009 | Markoll et al. |
| 2010/0036191 A1 | 2/2010 | Walter et al. |
| 2010/0185042 A1 | 7/2010 | Schneider et al. |
| 2010/0256438 A1 | 10/2010 | Mishelevich et al. |
| 2010/0256439 A1 | 10/2010 | Schneider et al. |
| 2010/0261992 A1 | 10/2010 | Axelgaard |
| 2010/0274327 A1 | 10/2010 | Carroll et al. |
| 2010/0286470 A1 | 11/2010 | Schneider et al. |
| 2010/0298623 A1 | 11/2010 | Mishelevich et al. |
| 2010/0331602 A1 | 12/2010 | Mishelevich et al. |
| 2011/0105826 A1 | 5/2011 | Mishelevich et al. |
| 2011/0118722 A1 | 5/2011 | Lischinsky et al. |
| 2011/0196438 A1 | 8/2011 | Mnozil et al. |
| 2011/0237921 A1 | 9/2011 | Askin, III et al. |
| 2011/0273251 A1 | 11/2011 | Mishelevich et al. |
| 2011/0275927 A1 | 11/2011 | Wagner et al. |
| 2011/0276108 A1 | 11/2011 | Crowe et al. |
| 2011/0319700 A1 | 12/2011 | Schneider |
| 2012/0035608 A1 | 2/2012 | Marchitto et al. |
| 2012/0101326 A1 | 4/2012 | Simon et al. |
| 2012/0226330 A1 | 9/2012 | Kolen et al. |
| 2012/0253098 A1 | 10/2012 | George et al. |
| 2012/0259382 A1 | 10/2012 | Trier et al. |
| 2012/0303076 A1 | 11/2012 | Fahey |
| 2012/0310035 A1 | 12/2012 | Schneider et al. |
| 2013/0006039 A1 | 1/2013 | Sadler |
| 2013/0096363 A1 | 4/2013 | Schneider et al. |
| 2013/0158634 A1* | 6/2013 | Ron Edoute ............ A61N 1/40 607/101 |
| 2013/0289433 A1 | 10/2013 | Jin et al. |
| 2014/0005759 A1* | 1/2014 | Fahey ................. A61N 1/0476 607/114 |
| 2014/0012064 A1 | 1/2014 | Riehl et al. |
| 2014/0221990 A1 | 8/2014 | Kreindel |
| 2014/0235928 A1 | 8/2014 | Zangen et al. |
| 2014/0249355 A1 | 9/2014 | Martinez |
| 2014/0249601 A1 | 9/2014 | Bachinski et al. |
| 2014/0324120 A1 | 10/2014 | Bogie et al. |
| 2014/0357935 A1 | 12/2014 | Ilmoniemi et al. |
| 2015/0005569 A1 | 1/2015 | Missoli |
| 2015/0005759 A1 | 1/2015 | Welches et al. |
| 2015/0018667 A1 | 1/2015 | Radman et al. |
| 2015/0094788 A1 | 4/2015 | Pierenkemper |
| 2015/0133718 A1 | 5/2015 | Schneider et al. |
| 2015/0148858 A1 | 5/2015 | Kaib |
| 2016/0136462 A1 | 5/2016 | Lewis, Jr. et al. |
| 2017/0036019 A1 | 2/2017 | Matsushita |
| 2017/0106203 A1 | 4/2017 | Schneider et al. |
| 2017/0361095 A1 | 12/2017 | Mueller et al. |
| 2018/0000347 A1 | 1/2018 | Perez et al. |
| 2018/0021565 A1 | 1/2018 | Dar et al. |
| 2018/0036548 A1 | 2/2018 | Nusse |
| 2018/0043151 A1 | 2/2018 | Ejiri et al. |
| 2018/0071544 A1 | 3/2018 | Ghiron et al. |
| 2018/0177996 A1 | 6/2018 | Gozani et al. |
| 2018/0296831 A1 | 10/2018 | Matsushita |
| 2018/0353767 A1 | 12/2018 | Biginton |
| 2019/0111255 A1 | 4/2019 | Errico et al. |
| 2019/0117965 A1 | 4/2019 | Iger et al. |
| 2019/0168012 A1 | 6/2019 | Biginton |
| 2019/0192853 A1 | 6/2019 | Kim et al. |
| 2019/0209836 A1 | 7/2019 | Yakoub et al. |
| 2019/0255346 A1 | 8/2019 | Ghiron |
| 2019/0269909 A1 | 9/2019 | Gozani et al. |
| 2019/0275320 A1 | 9/2019 | Kim et al. |
| 2020/0094066 A1 | 3/2020 | Heath |
| 2020/0114160 A1 | 4/2020 | Blendermann |
| 2020/0171297 A1 | 6/2020 | Kirson et al. |
| 2020/0197696 A1 | 6/2020 | Nagel et al. |
| 2020/0330782 A1 | 10/2020 | Zabara |
| 2020/0352633 A1 | 11/2020 | Treen et al. |
| 2020/0353244 A1 | 11/2020 | Yamazaki |
| 2020/0353273 A1 | 11/2020 | Zucco |
| 2020/0360681 A1 | 11/2020 | Lay |
| 2021/0008369 A1 | 1/2021 | Crosson |
| 2021/0038894 A1 | 2/2021 | Mowery et al. |
| 2021/0146150 A1 | 5/2021 | Frangineas, Jr. et al. |
| 2021/0275825 A1 | 9/2021 | Kreindel |
| 2021/0283395 A1 | 9/2021 | Kreindel |
| 2021/0361938 A1 | 11/2021 | Gershonowitz |

FOREIGN PATENT DOCUMENTS

| | | |
|---|---|---|
| AU | 2012244313 B2 | 11/2014 |
| AU | 2014203094 B2 | 7/2015 |
| AU | 2013207657 B2 | 11/2015 |

(56) References Cited

FOREIGN PATENT DOCUMENTS

| | | |
|---|---|---|
| BR | PI0812502 A2 | 6/2015 |
| CA | 2484880 A1 | 4/2006 |
| CA | 2604112 C | 7/2016 |
| CA | 3019140 A1 | 10/2017 |
| CA | 3019410 A1 | 10/2017 |
| CA | 3023821 A1 | 11/2017 |
| CH | 714113 A2 | 3/2019 |
| CN | 86204070 U | 9/1987 |
| CN | 87203746 U | 12/1987 |
| CN | 87215926 U | 7/1988 |
| CN | 1026953 C | 12/1994 |
| CN | 1027958 C | 3/1995 |
| CN | 2192348 Y | 3/1995 |
| CN | 1206975 C | 6/2005 |
| CN | 101234231 A | 8/2008 |
| CN | 101327358 A | 12/2008 |
| CN | 201906360 U | 7/2011 |
| CN | 102319141 A | 1/2012 |
| CN | 102711706 A | 10/2012 |
| CN | 10284 7231 A | 1/2013 |
| CN | 202637725 U | 1/2013 |
| CN | 203169831 U | 9/2013 |
| CN | 102319141 B | 8/2014 |
| CN | 106540375 A | 3/2017 |
| CN | 107613914 A | 1/2018 |
| CN | 108882992 A | 11/2018 |
| CN | 109310516 A | 2/2019 |
| CN | 112221015 A | 1/2021 |
| DE | 718637 C | 3/1942 |
| DE | 1118902 B | 12/1961 |
| DE | 2748780 A1 | 5/1978 |
| DE | 3205048 A1 | 8/1983 |
| DE | 3340974 A1 | 5/1985 |
| DE | 3610474 A1 | 10/1986 |
| DE | 3825165 A1 | 1/1990 |
| DE | 3340974 C2 | 7/1994 |
| DE | 69318706 T2 | 1/1999 |
| DE | 10062050 A1 | 4/2002 |
| DE | 102004006192 A1 | 9/2005 |
| DE | 60033756 T2 | 6/2007 |
| DE | 102009023855 A1 | 12/2010 |
| DE | 102009050010 A1 | 5/2011 |
| DE | 102010004307 A1 | 7/2011 |
| DE | 102011014291 A1 | 9/2012 |
| DE | 102013211859 B4 | 7/2015 |
| DE | 102016116399 A1 | 3/2018 |
| DE | 202016008884 U1 | 7/2020 |
| DE | 102010014157 B4 | 2/2021 |
| DK | 0633008 T3 | 3/1999 |
| EA | 000494 B1 | 8/1999 |
| EA | 002087 B1 | 12/2001 |
| EA | 002179 B1 | 2/2002 |
| EA | 003851 B1 | 10/2003 |
| EA | 007347 B1 | 8/2006 |
| EA | 007975 B1 | 2/2007 |
| EP | 0048451 A1 | 3/1982 |
| EP | 0209246 A1 | 1/1987 |
| EP | 0459101 A1 | 12/1991 |
| EP | 0459401 A1 | 12/1991 |
| EP | 0633008 A1 | 1/1995 |
| EP | 0788813 A1 | 8/1997 |
| EP | 0633008 B1 | 5/1998 |
| EP | 0692993 B1 | 9/1999 |
| EP | 1022034 A1 | 7/2000 |
| EP | 1916013 A1 | 4/2008 |
| EP | 2069014 A2 | 6/2009 |
| EP | 2139560 A1 | 1/2010 |
| EP | 2124800 B1 | 11/2010 |
| EP | 1917935 B1 | 1/2011 |
| EP | 2308559 A2 | 4/2011 |
| EP | 2139560 B1 | 5/2012 |
| EP | 2461765 A | 6/2012 |
| EP | 2069014 B1 | 6/2013 |
| EP | 2614807 A1 | 7/2013 |
| EP | 2676700 A2 | 12/2013 |
| EP | 2694159 A2 | 2/2014 |
| EP | 2749259 A1 | 7/2014 |
| EP | 2814445 A1 | 12/2014 |
| EP | 2856986 A | 4/2015 |
| EP | 3009167 A1 | 4/2016 |
| EP | 2501352 B1 | 7/2016 |
| EP | 3209246 A1 | 8/2017 |
| EP | 3342379 A1 | 7/2018 |
| EP | 3389532 A1 | 10/2018 |
| EP | 3434323 A1 | 1/2019 |
| EP | 3721939 A1 | 10/2020 |
| ES | 2118925 T3 | 10/1998 |
| ES | 2300569 T3 | 6/2008 |
| ES | 2305698 T3 | 11/2008 |
| ES | 2359581 T3 | 5/2011 |
| ES | 2533145 A2 | 4/2015 |
| ES | 2533145 B1 | 7/2016 |
| ES | 2533145 R1 | 10/2018 |
| FR | 3041881 A1 | 4/2017 |
| FR | 3061012 A1 | 6/2018 |
| GB | 260116 A | 10/1926 |
| GB | 304587 A | 3/1930 |
| GB | 390500 A | 4/1933 |
| GB | 871672 A | 6/1961 |
| GB | 2176009 A | 12/1986 |
| GB | 2188238 A | 9/1987 |
| GB | 2176009 B | 12/1989 |
| GB | 2261820 A | 6/1993 |
| GB | 2286660 A | 8/1995 |
| GB | 2395907 B | 12/2004 |
| GB | 2504984 A | 2/2014 |
| GB | 2521240 A | 6/2015 |
| GB | 2552004 A | 1/2018 |
| GR | 3027678 T3 | 11/1998 |
| IT | 1217550 B | 3/1990 |
| IT | RE20120010 A1 | 8/2013 |
| IT | UB20159823 A1 | 7/2017 |
| JP | 2003305131 A | 10/2003 |
| JP | 2006130055 A | 5/2006 |
| JP | 4178762 B2 | 11/2008 |
| JP | 4324673 B2 | 9/2009 |
| JP | 2010207268 A | 9/2010 |
| JP | 2010533054 A | 10/2010 |
| JP | 2011194176 A | 10/2011 |
| JP | 2013063285 A | 4/2013 |
| JP | 2017518857 A | 7/2017 |
| JP | 2018501927 A | 1/2018 |
| JP | 2018018650 A | 2/2018 |
| KR | 20030065126 A | 8/2003 |
| KR | 100484618 B1 | 4/2005 |
| KR | 100491988 B1 | 5/2005 |
| KR | 200407524 Y1 | 1/2006 |
| KR | 100556230 B1 | 3/2006 |
| KR | 200410065 Y1 | 3/2006 |
| KR | 100841596 B1 | 6/2008 |
| KR | 20090063618 A | 6/2009 |
| KR | 20090095143 A | 9/2009 |
| KR | 100936914 B1 | 1/2010 |
| KR | 1020100026107 A | 3/2010 |
| KR | 101022244 B1 | 3/2011 |
| KR | 20110123831 A | 11/2011 |
| KR | 20120037011 A | 4/2012 |
| KR | 101233286 B1 | 2/2013 |
| KR | 101233287 B1 | 2/2013 |
| KR | 20130072244 A | 7/2013 |
| KR | 101292289 B1 | 8/2013 |
| KR | 20130128391 A | 11/2013 |
| KR | 101413022 B1 | 7/2014 |
| KR | 101415141 B1 | 7/2014 |
| KR | 101447532 B1 | 10/2014 |
| KR | 101511444 B1 | 4/2015 |
| KR | 20150058102 A | 5/2015 |
| KR | 101539633 B1 | 7/2015 |
| KR | 20150079619 A | 7/2015 |
| KR | 20150106379 A | 9/2015 |
| KR | 101650155 B1 | 8/2016 |
| KR | 101673182 B1 | 11/2016 |
| KR | 20170090654 A | 8/2017 |
| KR | 20170107603 A | 9/2017 |

(56) References Cited

FOREIGN PATENT DOCUMENTS

| | | | |
|---|---|---|---|
| KR | 101794269 B1 | 11/2017 | |
| KR | 20180059114 A | 6/2018 | |
| KR | 20180092020 A | 8/2018 | |
| KR | 101941863 B1 | 1/2019 | |
| KR | 20190005981 A | 1/2019 | |
| KR | 102000971 B1 | 7/2019 | |
| KR | 20190001779 U | 7/2019 | |
| KR | 200491572 Y1 | 5/2020 | |
| KR | 20200000889 U | 5/2020 | |
| KR | 20200052602 A | 5/2020 | |
| KR | 20200056692 A | 5/2020 | |
| KR | 20200056693 A | 5/2020 | |
| KR | 20200056801 A | 5/2020 | |
| KR | 20200056802 A | 5/2020 | |
| KR | 20200057154 A | 5/2020 | |
| KR | 20210002973 A | 1/2021 | |
| KR | 20210002974 A | 1/2021 | |
| MX | 2012012158 A | 4/2014 | |
| NL | 7510644 A | 3/1977 | |
| NL | 1037451-02 | 5/2011 | |
| RU | 2212909 C2 | 9/2003 | |
| RU | 2226115 C2 | 3/2004 | |
| RU | 2281128 C2 | 8/2006 | |
| RU | 2373971 C2 | 11/2009 | |
| RU | 2392979 C2 | 6/2010 | |
| RU | 2395267 C2 | 7/2010 | |
| RU | 2496532 C2 | 10/2013 | |
| RU | 2529471 C2 | 9/2014 | |
| RU | 2596053 C2 | 8/2016 | |
| RU | 2637104 C2 | 11/2017 | |
| RU | 2645923 C2 | 2/2018 | |
| SI | 24921 A | 8/2016 | |
| TW | 200423986 A | 11/2004 | |
| WO | WO-9312835 A1 | 7/1993 | |
| WO | WO-9521655 A1 | 8/1995 | |
| WO | WO-9527533 A1 | 10/1995 | |
| WO | WO-9932191 A1 | 7/1999 | |
| WO | WO-0013749 A1 | 3/2000 | |
| WO | WO-0044346 A1 | 8/2000 | |
| WO | WO-0107111 A2 | 2/2001 | |
| WO | WO-0112089 A1 | 2/2001 | |
| WO | WO-0193797 A2 | 12/2001 | |
| WO | WO-0225675 A1 | 3/2002 | |
| WO | WO-03078596 A2 | 9/2003 | |
| WO | WO-03079916 A1 | 10/2003 | |
| WO | WO-03090863 A1 | 11/2003 | |
| WO | WO-03103769 A1 | 12/2003 | |
| WO | WO-2004078255 A1 | 9/2004 | |
| WO | WO-2004087255 A1 | 10/2004 | |
| WO | WO-2004095385 A2 | 11/2004 | |
| WO | WO-2004095835 A1 | 11/2004 | |
| WO | WO-2004096343 A2 | 11/2004 | |
| WO | WO-2004108211 A1 | 12/2004 | |
| WO | WO-2005032660 A1 | 4/2005 | |
| WO | WO-2005107866 A1 | 11/2005 | |
| WO | WO-2006115120 A1 | 11/2006 | |
| WO | WO-2007096206 A1 | 8/2007 | |
| WO | WO-2007140584 A1 | 12/2007 | |
| WO | WO-2008012827 A2 | 1/2008 | |
| WO | WO-2008049775 A1 | 5/2008 | |
| WO | WO-2008060494 A2 | 5/2008 | |
| WO | WO-2008109058 A1 | 9/2008 | |
| WO | WO-2008127011 A2 | 10/2008 | |
| WO | WO-2008145260 A2 | 12/2008 | |
| WO | WO-2009011708 A1 | 1/2009 | |
| WO | WO-2009013729 A2 | 1/2009 | |
| WO | WO-2009036040 A1 | 3/2009 | |
| WO | WO-2009042863 A1 | 4/2009 | |
| WO | WO-2009044400 A2 | 4/2009 | |
| WO | WO-2009047628 A2 | 4/2009 | |
| WO | WO-2009083915 A2 | 7/2009 | |
| WO | WO-2010007614 A2 | 1/2010 | |
| WO | WO-2010022278 A1 | 2/2010 | |
| WO | WO-2010007614 A3 | 5/2010 | |
| WO | WO-2010135425 A1 | 11/2010 | |
| WO | WO-2010139376 A1 | 12/2010 | |
| WO | WO-2011011749 A1 | 1/2011 | |
| WO | WO-2011016019 A1 | 2/2011 | |
| WO | WO-2011021184 A1 | 2/2011 | |
| WO | WO-2011045002 A1 | 4/2011 | |
| WO | WO-2011053607 A1 | 5/2011 | |
| WO | WO-2011058556 A2 | 5/2011 | |
| WO | WO-2011058565 A2 | 5/2011 | |
| WO | WO-2011156495 A2 | 12/2011 | |
| WO | WO-2012005766 A1 | 1/2012 | |
| WO | WO-2012029065 A2 | 3/2012 | |
| WO | WO-2012040243 A1 | 3/2012 | |
| WO | WO-2012073232 A1 | 6/2012 | |
| WO | WO-2012103632 A1 | 8/2012 | |
| WO | WO-2012119293 A1 | 9/2012 | |
| WO | WO-2012138169 A2 | 10/2012 | |
| WO | WO-2013021380 A1 | 2/2013 | |
| WO | WO-2013026393 A1 | 2/2013 | |
| WO | WO-2013035088 A1 | 3/2013 | |
| WO | WO-2013074576 A2 | 5/2013 | |
| WO | WO-2013098815 A | 7/2013 | |
| WO | WO-2013191699 A1 | 12/2013 | |
| WO | WO-2014009875 A2 | 1/2014 | |
| WO | WO-2014016820 A2 | 1/2014 | |
| WO | WO-2014109653 A1 | 7/2014 | |
| WO | WO-2014137344 A1 | 9/2014 | |
| WO | WO-2014141229 A1 | 9/2014 | |
| WO | WO-2014149021 A2 | 9/2014 | |
| WO | WO-2014151431 A2 | 9/2014 | |
| WO | WO-2014163020 A1 | 10/2014 | |
| WO | WO-2014164926 A1 | 10/2014 | |
| WO | WO-2015004540 A2 | 1/2015 | |
| WO | WO-2015012639 A1 | 1/2015 | |
| WO | WO-2015012672 A1 | 1/2015 | |
| WO | WO-2015052705 A1 | 4/2015 | |
| WO | WO-2015083305 A1 | 6/2015 | |
| WO | WO-2015137733 A1 | 9/2015 | |
| WO | WO-2015157725 A1 | 10/2015 | |
| WO | WO-2015179571 A1 | 11/2015 | |
| WO | WO-2016116747 A1 | 7/2016 | |
| WO | WO-2016140871 A1 | 9/2016 | |
| WO | WO-2017002065 A1 | 1/2017 | |
| WO | WO-2017103923 A1 | 6/2017 | |
| WO | WO-2017106878 A1 * | 6/2017 | ........... A61N 1/0456 |
| WO | WO-2017159959 A1 | 9/2017 | |
| WO | WO-2017160097 A2 | 9/2017 | |
| WO | WO-2017176621 A1 | 10/2017 | |
| WO | WO-2017196548 A1 | 11/2017 | |
| WO | WO-2017212253 A1 | 12/2017 | |
| WO | WO-2018006086 A1 | 1/2018 | |
| WO | WO-2018008023 A1 | 1/2018 | |
| WO | WO-2018044825 A1 | 3/2018 | |
| WO | WO-2018121998 A2 | 7/2018 | |
| WO | WO-2018122535 A1 | 7/2018 | |
| WO | WO-2017160097 A3 | 9/2018 | |
| WO | WO-2018208992 A1 | 11/2018 | |
| WO | WO-2019120420 A1 | 6/2019 | |
| WO | WO-2019150378 A1 | 8/2019 | |
| WO | WO-2019166965 A1 | 9/2019 | |
| WO | WO-2019173866 A1 | 9/2019 | |
| WO | WO-2019183622 A1 | 9/2019 | |
| WO | WO-2020002801 A1 | 1/2020 | |
| WO | WO-2020035852 A2 | 2/2020 | |
| WO | WO-2020041502 A1 | 2/2020 | |
| WO | WO-2020142470 A1 | 7/2020 | |
| WO | WO-2020144486 A1 | 7/2020 | |
| WO | WO-2020174444 A1 | 9/2020 | |
| WO | WO-2020183508 A1 | 9/2020 | |
| WO | WO-2020190514 A1 | 9/2020 | |
| WO | WO-2020208590 A1 | 10/2020 | |
| WO | WO-2020264263 A1 | 12/2020 | |
| WO | WO-2021013654 A1 | 1/2021 | |
| WO | WO-2021102365 A1 | 5/2021 | |

OTHER PUBLICATIONS

2018 Cutera University, Clinical Forum, Cutera 20, 26 pages.
501(k) K030708 Slendertone FLEX Letter from Department of

(56) References Cited

OTHER PUBLICATIONS

Health and Humane Serivces, Public Health Service, Jun. 25, 2003, 6 pages.
501(k) K163165 AM-100 Letter from Department of Health and Human Services, Public Health Service, Feb. 16, 2017, 9 pages.
Abulhasan, J.F., et al., "Peripheral Electrical and Magnetic Stimulation to Augment Resistance Training," Journal of Functional Morphology and Kinesiology, 1(3):328-342, (Sep. 2016).
Accent Radiofrequency System, Operator's Manual, Alma Lasers, Wellbeing Through Technology, 2008, 82 Pages.
Agilent Technologies, Inc., "Agilent 33500 Series 30 MHz Function/Arbitrary Waveform Generator User's Guide," Publication No. 33520-90001 (Dec. 2010), 278 pages.
Agilent Technologies, Inc., "Agilent Announces 30 MHz Function/Arbitrary Waveform Generators," Microwave J., URL: (Aug. 3, 2010), 8 pages.
*Allergan, Inc. et al* v. *BTL Healthcare Technologies A.S.*, PTAB-PGR2021-00015, Paper 16 (Decision Denying Institution of Post-Grant Review), Jun. 17, 2021, 20 pages.
*Allergan, Inc. et al* v. *BTL Healthcare Technologies A.S.*, PTAB-PGR2021-00016, Paper 16 (Decision Denying Institution of Post-Grant Review), Jun. 17, 2021, 20 pages.
*Allergan, Inc. et al* v. *BTL Healthcare Technologies A.S.*, PTAB-PGR2021-00017, Paper 16 (Decision Denying Institution of Post-Grant Review), Jun. 16, 2021, 33 pages.
*Allergan, Inc. et al* v. *BTL Healthcare Technologies A.S.*, PTAB-PGR2021-00018, Paper 16 (Decision Denying Institution of Post-Grant Review), Jun. 16, 2021, 42 pages.
*Allergan, Inc. et al* v. *BTL Healthcare Technologies A.S.*, PTAB-PGR2021-00020, Paper 16 (Decision Denying Institution of Post-Grant Review), Jun. 16, 2021, 35 pages.
*Allergan, Inc. et al* v. *BTL Healthcare Technologies A.S.*, PTAB-PGR2021-00021, Paper 17 (Decision Denying Institution of Post-Grant Review), Jun. 16, 2021, 33 pages.
*Allergan, Inc. et al* v. *BTL Healthcare Technologies A.S.*, PTAB-PGR2021-00022; PTAB-PGR2021-00023; PTAB-PGR2021-00024; PTAB-PGR2021-00025; PTAB-IPR2021-00296; PTAB-IPR2021-00312, Paper 11 (Decision Settlement Prior to Institution of Trial), Jul. 6, 2021, 4 pages.
Alma Lasers., "Accent Radiofrequency System, Operator's Manual," Wellbeing Through Technology, 2008, Chapters 1-8, Appendix A.
Arjunan, P.A., et al., "Computation and Evaluation of Features of Surface Electromyogram to Identify the Force of Muscle Contraction and Muscle Fatigue," BioMed research international 2014:197960, Hindawi Pub. Co, United States (2014).
Avram, M.M and Harry, R.S.,"Cryolipolysis for Subcutaneous Fat Layer Reduction," Lasers in Surgery and Medicine, 41(10):703-708, Wiley-Liss, United States (Dec. 2009).
Bachasson, D., et al., "Quadriceps Function Assessment Using an Incremental Test and Magnetic Neurostimulation: a Reliability Study," Journal of Electromyography and Kinesiology, 23(3):649-658, Elsevier, England, (Jun. 2013).
Barker, A.T, "An Introduction to the Basic Principles of Magnetic Nerve Stimulation," Journal of Clinical Neurophysiology, 8(1):26-37, Lippincott Williams & Wilkins, United States, (Jan. 1991).
Barker, A.T., et al., "Non-Invasive Magnetic Stimulation of Human Motor Cortex," Lancet 1(8437):1106-1107, Elsevier, England (May 1985).
Barker, A.T., "The History and Basic Principles of Magnetic Nerve Stimulation," Electroencephalography and Clinical Neurophysiology 51:3-21, Elsevier, Netherlands (1999).
Barrett, J., et al., "Mechanisms of Action Underlying the Effect of Repetitive Transcranial Magnetic Stimulation on Mood: Behavioral and Brain Imaging Studies," Neuropsychopharmacology 29(6):1172-1189, Nature Publishing Group, England (Jan. 14, 2004).
Behrens, M., et al., "Repetitive Peripheral Magnetic Stimulation (15 Hz RPMS) of the Human Soleus Muscle did not Affect Spinal Excitability," Journal of Sports Science and Medicine, 10(1):39-44, Dept. of Sports Medicine, Medical Faculty of Uludag University, Turkey (Mar. 2011).

Beilin, G., et al., "Electromagnetic Fields Applied to the Reduction of Abdominal Obesity," Journal of Cosmetic & Laser Therapy, 14(1):24-42, Informa Healthcare, England, (Feb. 2012).
Belanger, A-Y., "Chapter 13: Neuromuscular Electrical Stimulation," in Therapeutic Electrophysical Agents: Evidence Behind Practice, 3rd Edition, Lupash, E., ed., pp. 220-255, Lippincott Williams & Wilkins, United States (2015).
Benton, et al., "Functional Electrical Stimulation—A Practical Clinical Guide," Second Edition, The Professional Staff Association of the Rancho Los Amigos Hospital, Inc., 42 pages (1981).
Benton, L.A., et al., "Chapter 2: Physiological Basis of Nerve and Muscle Excitation" and "Chapter 4: General Uses of Electrical Stimulation," in Functional Electrical Stimulation: A Practical Guide, 2nd Edition, pp. 11-30 and 53-71, Rancho Los Amigos Rehabilitation Engineering Center, Downey, CA (1981), 42 pages.
Bergh, U., and Ekblom, B., "Influence of Muscle Temperature on Maximal Muscle Strength and Power Output in Human Skeletal Muscles," Acta Physiologica Scandinavica 107(1):33-37, Blackwell Scientific Publications, England (Aug. 1979).
Binder-Macleod, S.A., et al., "Force Output of Cat Motor Units Stimulated with Trains of Linearly Varying Frequency," Journal of Neurophysiology 61(1):208-217, American Physiological Society, United States (Jan. 1989).
Binder-Macleod, S.A., et al., "Use of a Catchlike Property of Human Skeletal Muscle to Reduce Fatigue," Muscle & Nerve 14(9):850-857, John Wiley & Sons, United States (Sep. 1991).
Bio Medical Research Limited., "Slendertone Flex Abdominal Training System, Instructions for Use," All pages (Aug. 2006).
Bio Medical Research Limited., "Slendertone Flex Max Instruction Manual," All pages (Apr. 2006).
Bio-Medical Research Ltd., K010335, 510(k) Summary, Slendertone Flex, All pages (Sep. 2001).
Bio-Medical Research Ltd., K022855 510(k) Summary, Slendertone, 1-6 (Mar. 2003).
Bischoff, C., et al., "Repetitive Magnetic Nerve Stimulation: Technical Considerations and Clinical Use in the Assessment of Neuromuscular Transmission," Electroencephalography and Clinical Neurophysiology 93(1):15-20, Elsevier, Ireland (Feb. 1994).
Bourland, J.D., et al., "Transchest Magnetic (Eddy-Current) Stimulation of the Dog Heart," Medical & Biological Engineering & Computing 28(2):196-198, Springer, United States (Mar. 1990).
BTL Industries, Inc., K163165 510(k) Summary, AM-100, All pages (Feb. 2017).
BTL Industries, Inc., K180813 510(k) Summary, Emsculpt, All pages (Mar. 2018).
*BTL Industries, Inc.* v. *Allergan Ltd. et al* DDE-1-20-cv-01046, Complaint for Patent Infringement and Exhibits 1-38, 821 pages (Aug. 2020).
*BTL Industries, Inc.* v. *Allergan Ltd. et al.,* DDE-1-20-cv-01046, Order Administratively Closing Case, Jul. 26, 2021, 1 page.
*BTL Industries, Inc.* v. *Allergan Ltd. et al* DDE-1-20-cv-01046, Order Granting Motion to Stay Pending Resolution of Proceedings at the International Trade Commission (Unopposed), 2 pages (Oct. 2020).
*BTL Industries, Inc.* v. *Allergan PLC et al* DDE-1-19-cv-02356, Complaint for Patent Infringement and Exhibits 1-34, 375 pages (Dec. 2019).
*BTL Industries, Inc.* v. *Allergan PLC et al* DDE-1-19-cv-02356, Order Granting Stipulation to Stay, Oct. 1, 2020, 1 page.
*BTL Industries, Inc.* v. *Allergan USA, Inc. et al.,* DDE-1-19-cv-02356, Order Administratively Closing Case, Jul. 26, 2021, 1 page.
Buenos Aires, Oct. 14, 2014, Venus Concept, Provision No. 7246, 56 pages (With Machine Translation).
Burge, S.M and Dawber, R.P.,"Hair Follicle Destruction and Regeneration in Guinea Pig Skin After Cutaneous Freeze Injury," Cryobiology, 27(2):153-163, Elsevier, Netherlands (Apr. 1990).
Busso, M. and Denkova, R., "Efficacy of High Intensity Focused Electro-Magnetic (HIFEM) Field Therapy When Used For Non-Invasive Buttocks Augmentation and Lifting: A Clinical Study" American Society for Laser Medicine and Surgery Abstracts, 382 (2018).

(56) References Cited

OTHER PUBLICATIONS

Bustamante, V., et al., "Muscle Training With Repetitive Magnetic Stimulation of the Quadriceps in Severe COPD Patients," Respiratory Medicine, 104(2):237-245, Elsevier, England, (Feb. 2010).

Bustamante, V., et al., "Redox Balance Following Magnetic Stimulation Training in the Quadriceps of Patients With Severe COPD," Free Radical Research, 42(11-12):939-948, Informa Healthcare, England, (Nov. 2008).

Callaghan, M.J., et al., "Electric Muscle Stimulation of the Quadriceps in the Treatment of Patellofemoral Pain," Archives of Physical Medicine and Rehabilitation 85(6):956-962, W.B. Saunders, United Staes (Jun. 2004).

Carbonaro, M., et al., "Architectural Changes in Superficial and Deep Compartments of the Tibialis Anterior during Electrical Stimulation over Different Sites," IEEE transactions on Neural Systems and Rehabilitation Engineering 28(11):2557-2565, IEEE, United States (Nov. 2020).

Caress, J.B., et al., "A Novel Method of Inducing Muscle Cramps Using Repetitive Magnetic Stimulation," Muscle Nerve, 23(1):126-128, John Wiley & Sons, United States, (Jan. 2000).

Certain Non-Invasive Aesthetic Body Contouring Devices, Components Thereof, and Methods of Using the Same, Inv. No. 337-TA-1219, BTL's Statement of Suggested Claim Terms to Be Construed Pursuant to Ground Rule 6b, Nov. 4, 2020, 2 pages.

Certain Non-Invasive Aesthetic Body Contouring Devices, Components Thereof, and Methods of Using the Same, Inv. No. 337-TA-1219, Complainant BTL's Proposed Construction of Disputed Claim Terms, Dec. 8, 2020, 19 pages.

Certain Non-Invasive Aesthetic Body Contouring Devices, Components Thereof, and Methods of Using the Same, Inv. No. 337-TA-1219, Complaint, Aug. 5, 2020, 93 pages.

Certain Non-Invasive Aesthetic Body Contouring Devices, Components Thereof, and Methods of Using the Same, Inv. No. 337-TA-1219, Joint Claim Construction Chart, Dec. 14, 2020, 15 pages.

Certain Non-Invasive Aesthetic Body Contouring Devices, Components Thereof, and Methods of Using the Same; Inv. No. 337-TA-1219, Joint Claim Construction Chart, Dec. 18, 2020, 15 pages.

Certain Non-Invasive Aesthetic Body Contouring Devices, Components Thereof, and Methods of Using the Same, Inv. No. 337-TA-1219, Respondents' Allergan Limited, Allergan USA, Inc., Allergan, Inc., Zeltiq Aesthetics, Inc., Zeltiq Ireland Unlimited Company, and Zimmer MedizinSysteme GmbH's Notice of Prior Art, Nov. 20, 2020, 5 pages.

Certain Non-Invasive Aesthetic Body Contouring Devices, Components Thereof, and Methods of Using the Same, Inv. No. 337-TA-1219, Respondents' List of Claim Terms for Construction, Nov. 4, 2020, 8 pages.

Certain Non-Invasive Aesthetic Body Contouring Devices, Components Thereof, and Methods of Using the Same; Inv. No. 337-TA-1219, Respondents' List of Proposed Claim Constructions and Their Intrinsic and Extrinsic Support, filed Dec. 15, 2020, 23 pages.

Certain Non-Invasive Aesthetic Body Contouring Devices, Components Thereof, and Methods of Using the Same, Inv. No. 337-TA-1219, Response of Respondent Zimmer MedizinSysteme GmbH to the Complaint and Notice of Investigation, Oct. 22, 2020, 68 pages.

Certain Non-Invasive Aesthetic Body Contouring Devices, Components Thereof, and Methods of Using the Same, Inv. No. 337-TA-1219, Response of Respondents Allergan Limited, Allergan USA, Inc., Allergan, Inc., Zeltiq Aesthetics, Inc., and Zeltiq IrelandUnlimited Company to the Complaint and Notice of Investigation, Oct. 22, 2020, 69 pages.

Certain Non-Invasive Aesthetic Body-Contouring Devices, Components Thereof, and Methods of Using Same, Notice of Institution of Investigation, Inv. No. 337-TA-1219, Notice of Institution of Investigation, Sep. 2, 2020, 21 pages.

Certain Non-Invasive Aesthetic Body-Contouring Devices, Components Thereof, and Methods of Using the Same, Inv. No. 337-TA-1219, Order No. 21 (Initial Determination), Apr. 28, 2021, 5 pages.

Certain Non-Invasive Aesthetic Body-Contouring Devices, Components Thereof, and Methods of Using the Same, Inv. No. 337-TA-1219, Order No. 30 (Order Concerning the Procedural Schedule), Aug. 4, 2021, 3 pages.

Certain Non-Invasive Aesthetic Body-Contouring Devices, Components Thereof, and Methods of Using the Same, Inv. No. 337-TA-1219, Order No. 17: Amending Procedural Schedule, Apr. 9, 2021, 4 pages.

Certified English Translation of Belyaev, A.G., "Effect of Magnetic Stimulation on the Strength Capacity of Skeletal Muscles," Ph.D. Thesis Abstract, Smolensk State Academy of Physical Culture, Sport, and Tourism, Dec. 11, 2020, 23 pages.

Certified English Translation of Belyaev, A.G., "Effect of Magnetic Stimulation on the Strength Capacity of Skeletal Muscles," Ph.D. Thesis, Smolensk State Academy of Physical Culture, Sport, and Tourism, Dec. 11, 2020, 117 pages.

Chattanooga Group of Encore Medical, L.P., "Intelect SWD 100 User Manual, Operation & Installation Instructions for Intelect SWD 00-Model 1600," All pages (2009).

Chesterton, L.S., et al.,"Skin Temperature Response to Cryotherapy," Archives of Physical Medicine and Rehabilitation, 83(4):543-549, W.B. Saunders, United States (Apr. 2002).

Collins, D.F., et al., "Large Involuntary Forces Consistent With Plateau-Like Behavior of Human Motoneurons," Journal of Neuroscience 21(11):4059-4065, Society for Neuroscience, United States (Jun. 2001).

Colson, S., et al., "Re-Examination of Training Effects by Electrostimulation in the Human Elbow Musculoskeletal System," International Journal of Sports Medicine 21(4):281-288, Stuttgart, Thieme (May 2000).

Course in Physical Therapy, Presentation, Jan. 4, 2013, 156 pages.

CR Technologies, "Salus Talent Pop Manual KFDA First Approval Document" (English Translation), Nov. 25, 2011, 47 pages.

CR Technologies, "Notification of medical device manufacturing item permission, Salus Talent Pop KFDA Approval Document" (English Translation), 3 pages (Sep. 2011).

CR Technology Co, Ltd., "Salus-Talent Double Sales Brochure" 2 pages, (Oct. 2020).

CR Technology Co. Ltd., "Medical Laser Irradiator Salus-Talent-Pop User Manual Version 1.00" (Nov. 2020).

CR Technology Co. Ltd., Salus Talent Pop User Manual, Ver. 1.00, All pages, Approx. 2012.

CR Technology, Salus-Talent, Technical File of Electro-magnetic Stimulator, Document No. TF-C05, 2008, 241 pages.

CR Technology, Technology for Health and Business for Human Being, investor relations, 2008, 21 pages.

Currier, D. P., "Effects of Electrical and Electromagnetic Stimulation after Anterior Cruciate Ligament Reconstruction," The Journal of Orthopaedic and Sports Physical Therapy 17(4):177-84, Williams And Wilkins, United States (1993).

Cutera, truSculptflex, Brochure, dated 2019, 2 pages.

Cynosure, SculpSure TM, The New Shape of Energy-Based body Contouring, 2015, Cynosure Inc, 2 pages.

Cynosure,Smooth Shapes XV, Now with Smoothshape petite, Transforming non-invasive Body Shaping,Retrieved from the Internet: (www.cynosure.com), 2011, Cynosure Inc, 8 pages.

Davies, C.T., et al., "Contractile Properties of the Human Triceps Surae With Some Observations on the Effects of Temperature and Exercise," European Journal of Applied Physiology and Occupational Physiology 49(2):255-269, Springer Verlag, Germany (Aug. 1982).

Deng, Z.D., et al., "Electric Field Depth-Focality Tradeoff in Transcranial Magnetic Stimulation: Simulation Comparison of 50 Coil Designs," Brain stimulation 6(1):1-13, Elsevier, New York (Jan. 2013).

Department of Health and Human Services, 501(k) Letter and Summary for K092476 Body Control System 4M Powered Muscle Stimulator, dated May 7, 2010, 5 pages.

Department of Health and Human Services, 501(k) Letter and Summary for K160992 HPM-6000 Powered Muscle Stimulator, dated Oct. 21, 2016, 9 pages.

(56) References Cited

OTHER PUBLICATIONS

Department of Health and Human Services, 501(k) Letter and Summary for K163415 SlimShape System Powered Muscle Stimulator, dated Apr. 20, 2017, 8 pages.
Depatment of Health and Human Services, 501(k) Letter and Summary for K182106 BTL 799-2T Powered Muscle Stimulator, dated Oct. 23, 2018, 9 pages.
Depatment of Health and Human Services, 501(k) Letter and Summary for K190456 BTL 799-2L Powered Muscle Stimulator, dated Jul. 5, 2019, 9 pages.
Depatment of Health and Human Services, 501(k) Letter and Summary for K192224 BTL 899 Powered Muscle Stimulator, dated Dec. 5, 2019, 11 pages.
Doucet, B., et al., "Neuromuscular Electrical Stimulation for Skeletal Muscle Function," Yale Journal of Biology & Medicine 85:201-215, Yale Journal of Biology and Medicine, United States (Jun. 2012).
Dudley, G. and Stevenson, S., "Use of Electrical Stimulation in Strength and Power Training," Special Problems in Strength and Power Training :426-435 (2003).
Duncan, D., et al., "Noninvasive Induction of Muscle Fiber Hypertrophy and Hyperplasia: Effects of High-Intensity Focused Electromagnetic Field Evaluated in an In-Vivo Porcine Model: A Pilot Study," Aesthetic Surgery Journal 40(5):568-574, Oxford University Press, United States (Apr. 2020).
DuoMAG Magnetic Stimulator, Alien Technik User Manuel, Jun. 26, 2012,48 pages, Version 2.1.
Dybek, T., et al.,"Impact of 10 Sessions of Whole Body Cryostimulation on Aerobic and Anaerobic Capacity and on Selected Blood Count Parameters," Biology of Sport, 29(1):39-43 (Jan. 2012).
Dynatronics., "Better Rehab Solutions for Better Outcomes," Rehabilitation Products Guide 2.3, 2017, 52 pages.
Effective PEMF Magnetic Fat Reduction Slimming Body Beauty Salon Machine (PEMF Star), Wolfbeauty 1980, PEMF Star, China, Retrieved from the Internet: (URL: https://www.ec21.com/product-details/Effective-PEMF-Magnetic-Fat-Reduction--89287 46.html), 2019, 5 pages.
Elamed, Magnetic Therapeutic Apparatus for Running Pulse Magfield small-sized ALMAG-01 Manual, allegedly accessed on Nov. 18, 2020, All pages.
Eliminate Stubborn Fat without Surgery or Downtime and Feel Great From Every Angle, Fear No Mirror®, Consultation Guide, Coolsculpting, 2014, 20 pages.
Energist Ltd—Acquired Chromogenez—Old Account, ilipo—Laser Liposuction (i-Lipo), Video Screenshots, Aug. 10, 2009, 5 pages.
Enoka, R.M., "Muscle Strength and Its Development," Sports Medicine 6:146-168, Springer (Oct. 1988).
Epstein, C., et al., "The Oxford Handbook of Transcranial Stimulation," 773 pages (2008).
European Commission, Neuodegenerative Disorders, 10 pages printed Dec. 27, 2016.
European Commission, "Neurogenerative Disorders," 10 pages printed Dec. 27, 2016.
European Patent Office, International Search Report and Written Opinion for International Application No. PCT/IB2016/053930, dated Dec. 12, 2016, 19 pages.
Exilis, Operator's Manual, BTL, 2012, 44 Pages.
Faghri, P.D., et al., "The Effects of Functional Electrical Stimulation on Shoulder Subluxation, Arm Function Recovery, and Shoulder Pain in Hemiplegic Stroke Patients," Archives of Physical Medicine and Rehabilitation 75(1):73-79, W.B. Saunders, United States (Jan. 1994).
FDA letter to Venus Legacy, Dec. 19, 2014, 7 pages.
Fischer, J., et al., "Precise Subpixel Position Measurement with Linear Interpolation of CMOS Sensor Image Data," The 6th IEEE International Conference on Intelligent Data Acquisition and Advanced Computing Systems, 500-504 (Sep. 2011).
Fisher, R., et al., "ILAE Official Report: a Practical Clinical Definition of Epilepsy," Epilepsia, 55(4):475-482, Blackwell Science, United States (Apr. 2014).

Fujimura, K., et al., "Effects of Repetitive Peripheral Magnetic Stimulation on Shoulder Subluxations Caused by Stroke: A Preliminary Study," Neuromodulation: Journal of the International Neuromodulation Society 23(6):847-851, Wiley-Blackwell, United States (Nov. 2020).
Gaines, M., "Slendertone Abdominal Training System, the First FDA-Cleared Abdominal Belt, Introduced in United States by Compex Technologies on Time for Holiday Gift-Giving," Business Wire 44199 (Oct. 2003).
Geddes, L.A., "History of Magnetic Stimulation of the Nervous System," Journal of Clinical Neurophysiology 8(1):3-9, Lippincott Williams & Wilkins, United States (Jan. 1991).
Goetz, S.M., et al., "Coil Design for Neuromuscular Magnetic Stimulation Based on a Detailed 3-D Thigh Model," IEEE Transactions on Magnetics, 50(6):10, IEEE, (Jun. 2014).
Goodman, B.E., "Channels Active in the Excitability of Nerves and Skeletal Muscles Across the Neuromuscular Junction: Basic Function and Pathophysiology," Advances in Physiology Education 32(2):127-135, American Physiological Society, United States (Jun. 2008).
Gorgey, A., et al., "Effects of Electrical Stimulation Parameters on Fatigue in Skeletal Muscle," The Journal of Orthopaedic and Sports Physical Therapy 39(9):684-692, Williams And Wilkins, United States (Sep. 2009).
Gorodnichev, R.M., et al., "The Effect of Electromagnetic Stimulation on the Parameters of Muscular Strength," Human Physiology 40:65-69 (2014).
Gorodnichev, R.M., "Magnetic Stimulation of Muscles as New Method to Enhance Their Strength," Velikie Luki State Academy of Physical Culture and Sport, Velikie Luki, 2016, 5 pages.
Guangzhou HEMS Tech, PEMF Star, May 31, 2019, 5 pages.
Halaas, Y. and Bernardy, J., "Biochemical Perspective of Fat Physiology after Application of HIFEM Field Technology: Additional Investigation of Fat Disruption Effects in a Porcine Study," American Society for Laser Medicine and Surgery Abstracts, S4 (2019).
Hamnegard, C.H., et al., "Quadriceps Strength Assessed by Magnetic Stimulation of the Femoral Nerve in Normal Subjects," Clinical Physiology and Functional Imaging, 24(5):276-280, Blackwell, England, (Sep. 2004).
Han, B.H., et al., "Development of four-channel magnetic nerve stimulator," 2001 Proceedings of the 23rd Annual EMBS International Conference, pp. 1325-1327, Turkey (2001).
Han, T.R., et al., "Magnetic Stimulation of the Quadriceps Femoris Muscle: Comparison of Pain With Electrical Stimulation," American Journal of Physical Medicine & Rehabilitation, 85(7):593-599, Lippincott Williams & Wilkins, United States, (Jul. 2006).
Harkey, M.S., "Disinhibitory Interventions and Voluntary Quadriceps Activation: A Systematic Review," Journal of Athletic Training 49(3):411-421, National Athletic Trainers' Association, United States (2014).
Heidland, A., et al., "Neuromuscular Electrostimulation Techniques: Historical Aspects and Current Possibilities in Treatment of Pain and Muscle Waisting," Clinical Nephrology 79 Suppl 1:S12-S23, Dustri-Verlag Dr. Karl Feistle, Germany (Jan. 2012).
Heisel, Jurgen, Physikalische Medizin, Stuttgart: Georg Thieme Verlag KG, 2005. ISBN 3-13-139881-7. p. 159.
Hera Estetik Medikal, "Lipostar" dated Jul. 7, 2014, accessed at https://www.youtube.com/watch?v=-R70nFIK9go, accessed on Dec. 15, 2021.
Hera Estetik Medikal, "Lipostar Manyetik Incelme", accessed at https://www.heraestetik.com/en/urundetay/liposter-manyetik-incelme, accessed on Dec. 15, 2021.
Hill, A., "The Influence of Temperature on the Tension Developed in an Isometric Twitch," Proceeding of the Royal Society B 138:349-354, (Sep. 1951).
Hirvonen, H.E., et al.,"Effectiveness of Different Cryotherapies on Pain and Disease Activity in Active Rheumatoid Arthritis. A Randomised Single Blinded Controlled Trial,"Clinical and Experimental Rheumatology, 24(3):295-301, Clinical and Experimental Rheumatology SAS, Italy (May-Jun. 2006).

(56) References Cited

OTHER PUBLICATIONS

Hovey, C. and Jalinous, R., "The Guide to Magnetic Stimulation" Magstim, Pioneers in Nerve Stimulation and Monitoring, pp. 1-44 (2016).

Hovey, C., et al., "The Guide to Magnetic Stimulation," The Magstim Company Limited, 48 pages (Jul. 2006).

Huang, Y.Z., et al., "Theta Burst Stimulation of the Human Motor Cortex," Neuron 45(2):201-206, Cell Press, United States (Jan. 2005).

I-Lipo by Chroma genex, i-Lipo Ultra is the Intelligent, Non-Surgical Alternative to Liposuction, 2011, 2 pages.

Increasing Physiotherapy Presence in Cosmetology, Spa Inspirations, Jan. 2012, pp. 34-35.

Irazoqui P., Post Grant Review of U.S. Pat. No. 10,695,576, PTAB-PGR2021-00024, filed as EX1085, Dec. 14, 2020, 25 pages.

Iskra Medical, Magneto System, 2012, 2 pages.

Iskra Medical, "TESLA Stym—Functional Magnetic Stimulation FMS," Nov. 2013, http://ww.iskramedical.eu/magneto-therapy-medical/tesla-stym, 5 pages.

Iskra Medical, "TESLA Stym Website," URL: https://web.archive.org/web/20131106123126/http:/www.iskramedical.eu:80/magneto-therapy-medical/tesla-stym (Nov. 6, 2013).

Izumiya, Y., et al., "Fast/Glycolytic Muscle Fiber Growth Reduces Fat Mass and Improves Metabolic Parameters in Obese Mice", Cell Metabolism 7(2):159-172, Cell Press, United States (Feb. 2008).

Jacob, C., et al., "High Intensity Focused Electro-Magnetic Technology (HIFEM) for Non-Invasive Buttock Lifting and Toning of Gluteal Muscles: A Multi-Center Efficacy And Safety Study," Journal of Drugs in Dermatology 17(11):1229-1232, Physicians Continuing Education Corporation, United States (Nov. 2018).

Jacob, C.I., et al., "Safety And Efficacy of a Novel High-Intensity Focused Electromagnetic Technology Device for Noninvasive Abdominal Body Shaping," Journal of Cosmetic Dermatology, 17(5):783-787, Blackwell Science, United States (Oct. 2018).

Jacobm C., and Paskova, "A Novel Non-Invasive Technology Based on Simultaneous Induction of Changes in Adipose and Muscle Tissues: Safety and Efficacy of a High Intensity Focused Electro-Magnetic (HIFEM) Field Device Used For Abdominal Body Shaping," American Society for Laser Medicine and Surgery, 2018 Electronic Posters (ePosters) Town Hall and ePosters, 369, p. 1, Wiley Periodicals, Inc. (2018).

Johari Digital Healthcare Ltd., 510(k)-K062439 Powertone Letter from Department of Health and Humane Services Summary, Public Health Service, Jan. 8, 2007, 6 pages.

Johari Digital Healthcare Ltd., "510(k)-K131291 Torc Body Letter from Department of Health and Humane Services", Public Health Service, Jun. 14, 2013, 10 pages.

Johari Digital Healthcare Ltd., K131291 510(k) Summary, TorcBody, All pages (Jun. 2013).

Jutte, L.S., et al., "The Relationship Between Intramuscular Temperature, Skin Temperature, and Adipose Thickness During Cryotherapy and Rewarming," Archives of Physical Medicine and Rehabilitation, 82(6):845-850, W.B. Saunders, United States (Jun. 2001).

Katuscakova, Z.L., et al., High Induction Magnet Therapy in Rehabilitation, Department of Physiactric Rehabilitation, 2012, 72 pages.

Katz, B., et al., "Changes in Subcutaneous Abdominal Fat Thickness Following High-Intensity Focused Electro-Magnetic (HIFEM) Field Treatments: A Multi Center Ultrasound Study," American Society for Laser Medicine and Surgery Abstracts, 360-361 (2018).

Katz, B., et al., "Ultrasound Assessment of Subcutaneous Abdominal Fat Thickness after Treatments with a High-Intensity Focused Electromagnetic Field Device: A Multicenter Study," Dermatologic Surgery 45(12):1542-1548, Williams & Wilkins, United States (Dec. 2019).

Kavanagh, S., et al., "Use of a Neuromuscular Electrical Stimulation Device for Facial Muscle Toning: A Randomized, Controlled Trial," Journal of Cosmetic Dermatology 11(4):261-266, Blackwell Science, United States (Dec. 2012).

Kent, D., and Jacob C., "Computed Tomography (CT) Based Evidence of Simultaneous Changes in Human Adipose and Muscle Tissues Following a High Intensity Focused Electro-Magnetic Field (HIFEM) Application: A New Method for Non-Invasive Body Sculpting," American Society for Laser Medicine and Surgery Abstracts, p. 370 (2018).

Kent, D,E. and Jacob, C.I., Simultaneous Changes in Abdominal Adipose and Muscle Tissues Following Treatments by High-Intensity Focused Electromagnetic HIFEM Technology-Based Device: Computed Tomography Evaluation, Journal of Drugs in Dermatology 18(11):1098-1102, Physicians Continuing Education Corporation, United States (Nov. 2019).

Kim, Y.H., et al.,"The Effect of Cold Air Application on Intra-Articular and Skin Temperatures in the Knee," Yonsei Medical Journal, 43(5):621-626, Yonsei University, Korea (South) (Oct. 2002).

Kinney, B.M. and Lozanova P., "High Intensity Focused Electromagnetic Therapy Evaluated by Magnetic Resonance Imaging: Safety and Efficacy Study of a Dual Tissue Effect Based Non-Invasive Abdominal Body Shaping," Lasers in Surgery and Medicine 51(1):40-46, Wiley-Liss, United States (Jan. 2019).

Kocbach et al., "A Simulation Approach to Optimizing Performance of Equipment for Thermostimulation of Muscle Tissue using COMSOL Multiphysics" Article in Biophysics & Bioeng. dated 2011, 26 pages.

Kolin, A., et al., "Stimulation of Irritable Tissues by means of an Alternating Magnetic Field," Proceedings of the Society for Experimental Biology and Medicine 102:251-253, Blackwell Science, United States (Oct. 1959).

Korman, P., et al., "Temperature Changes In Rheumatoid Hand Treated With Nitrogen Vapors and Cold Air," Rheumatology International, 32(10):2987-2992, Springer International, Germany (Oct. 2012).

Kotz, Y., "Theory and Practice of Physical Culture," Training of Skeletal Muscle With Method of Electrostimulation, 64-67 (Mar. 1971).

Kotz, Y., "Theory and Practice of Physical Culture," Training of Skeletal Muscle With Method ofElectrostimulation, 66-72 (Apr. 1971).

Krueger, N. et al., "Safety and Efficacy of a New Device Combining Radiofrequency and Low-Frequency Pulsed Electromagnetic Fields for the Treatment of Facial Rhytides," Journal of Drugs in Dermatology 11(11):1306-1309, Physicians Continuing Education Corporation, United States (Nov. 2012).

Kumar, N. and Agnihotri, R.C., "Effect of Frequency and Amplitude of Fes Pulses on Muscle Fatigue During Toning of Muscles," Journal of Scientific and Industrial Research 67(4):288-290, (Apr. 2008).

Lampropoulou, S.I., et al., "Magnetic Versus Electrical Stimulation in the Interpolation Twitch Technique of Elbow Flexors," Journal of Sports Science and Medicine, 11(4):709-718, Dept. of Sports Medicine, Medical Faculty of Uludag University, Turkey (Dec. 2012).

Langford, J. and McCarthy, P.W., "Randomised controlled clinical trial of magnet use in chronic low back pain; a pilot study," Clinical Chiropractic 8(1):13-19, Elsevier (Mar. 2005).

Lee, P.B., et al., "Efficacy of Pulsed Electromagnetic Therapy for Chronic Lower Back Pain: a Randomized, Double-blind, Placebo-controlled Study," The Journal of International Medical Research 34(2):160-167, Cambridge Medical Publications, England (Mar.-Apr. 2006).

Leitch, M., et al., "Intramuscular Stimulation of Tibialis Anterior in Human Subjects: The Effects of Discharge Variability on Force Production and Fatigue," Physiological Reports 5(15):e13326, Wiley Periodicals, Inc., United States (Aug. 2017).

Leon-Salas, W.D., et al., "A Dual Mode Pulsed Electro-Magnetic Cell Stimulator Produces Acceleration of Myogenic Differentiation," Recent Patents on Biotechnology 7(1):71-81, Bentham Science Publishers, United Arab Emirates (Apr. 2013).

Letter from Department of Health and Human Services, Public Health Service, Dec. 19, 2014, 7 pages.

(56) References Cited

OTHER PUBLICATIONS

Lin, V.W., et al., "Functional Magnetic Stimulation: A New Modality for Enhancing Systemic Fibrinolysis," Archives of Physical Medicine and Rehabilitation 80(5):545-550, W.B. Saunders, United States (May 1999).

Lin, V.W., et al., "Functional Magnetic Stimulation for Conditioning of Expiratory Muscles in Patients with Spinal Cord Injury.," Archives of Physical medicine and Rehabilitation 82(2):162-166, W.B. Saunders, United States (Feb. 2001).

Lin, V.W., et al., "Functional Magnetic Stimulation for Restoring Cough in Patients With Tetraplegia," Archives of Physical Medicine and Rehabilitation, 79(5):517-522, W.B. Saunders, United States, (May 1998).

Lin, V.W., et al., "Functional Magnetic Stimulation of Expiratory Muscles: a Noninvasive and New Method for Restoring Cough," Journal of Applied Physiology (1985), 84(4):1144-1150, American Physiological Society, United States, (Apr. 1998).

Lin, V.W., et al., "Functional Magnetic Stimulation of the Respiratory Muscles in Dogs," Muscle & Nerve 21 (8):1048-1057, John Wiley & Sons, United States (Aug. 1998).

Linehan, C., et al., Brainwave the Irish EpilepsyAssoication, "The Prevalence of Epilepsy in Ireland" Summary Report, pp. 1-8 (May 2009).

Lotz, B.P., et al., "Preferential Activation of Muscle Fibers with Peripheral Magnetic Stimulation of the Limb," Muscle & Nerve, 12(8):636-639, John Wiley & Sons, United States (Aug. 1989).

*Lumenis Be Ltd. v. BTL Healthcare Technologies A.S.*, PTAB-IPR2021-01402, Declaration of Dr. Marom Bikson (EX1002), Sep. 13, 2021, 244 pages.

*Lumenis Be Ltd. v. BTL Healthcare Technologies A.S.*, PTAB-IPR2021-01402, U.S. Pat. No. 10,821,295 Petition for Inter Partes Review, Sep. 13, 2021, 81 pages.

*Lumenis Be Ltd. v. BTL Healthcare Technologies A.S.*, PTAB-IPR2021-01403, Declaration of Dr. Marom Bikson (EX1002), Sep. 13, 2021, 243 pages.

*Lumenis Be Ltd. v. BTL Healthcare Technologies A.S.*, PTAB-IPR2021-01403, U.S. Pat. No. 10,821,295 Petition for Inter Partes Review, Sep. 13, 2021, 84 pages.

*Lumenis Be Ltd. v. BTL Healthcare Technologies A.S.*, PTAB-IPR2021-01404, Declaration of Dr. Marom Bikson (EX1002), Sep. 13, 2021, 245 pages.

*Lumenis Be Ltd. v. BTL Healthcare Technologies A.S.*, PTAB-IPR2021-01404, U.S. Pat. No. 10,124,187 Petition for Inter Partes Review, Sep. 13, 2021, 82 pages.

*Lumenis Be Ltd. v. BTL Healthcare Technologies A.S.*, PTAB-IPR2021-01405, Declaration of Dr. Marom Bikson (EX1002), Sep. 13, 2021, 247 pages.

*Lumenis Be Ltd. v. BTL Healthcare Technologies A.S.*, PTAB-IPR2021-01405, U.S. Pat. No. 10,124,187 Petition for Inter Partes Review, Sep. 13, 2021, 86 pages.

*Lumenis Be Ltd. v. BTL Healthcare Technologies A.S.*, PTAB-IPR2022-00126, Declaration of Dr. Marom Bikson (EX1002), Nov. 10, 2021, 263 pages.

*Lumenis Be Ltd. v. BTL Healthcare Technologies A.S.*, PTAB-IPR2022-00126, U.S. Pat. No. 10,695,576 Petition for Inter Partes Review, Nov. 10, 2021, 83 pages.

*Lumenis Be Ltd. v. BTL Healthcare Technologies A.S.*, PTAB-IPR2022-00127, Declaration of Dr. Marom Bikson (EX1002), Nov. 10, 2021, 269 pages.

*Lumenis Be Ltd. v. BTL Healthcare Technologies A.S.*, PTAB-IPR2022-00127, U.S. Pat. No. 10,695,576 Petition for Inter Partes Review, Nov. 10, 2021, 84 pages.

*Lumenis Ltd. v. BTL Healthcare Technologies A.S.*, PTAB-IPR2021-01273, Declaration of Dr. Marom Bikson (EX1002), Aug. 13, 2021, 225 pages.

*Lumenis Ltd. v. BTL Healthcare Technologies A.S.*, PTAB-IPR2021-01273, U.S. Pat. No. 10,478,634, Petition for Inter Partes Review, Aug. 13, 2021, 70 pages.

*Lumenis Ltd. v. BTL Healthcare Technologies A.S.*, PTAB-IPR2021-01275, Declaration of Dr. Marom Bikson (EX1002), Aug. 5, 2021, 282 pages.

*Lumenis Ltd. v. BTL Healthcare Technologies A.S.*, PTAB-IPR2021-01275, U.S. Pat. No. 10,632,321, Petition for Inter Partes Review, Aug. 5, 2021, 92 pages.

*Lumenis Ltd. v. BTL Healthcare Technologies A.S.*, PTAB-IPR2021-01276, Declaration of Dr. Marom Bikson (EX1002), Aug. 5, 2021, 241 pages.

*Lumenis Ltd. v. BTL Healthcare Technologies A.S.*, PTAB-IPR2021-01276, U.S. Pat. No. 10,965,575, Petition for Inter Partes Review, Aug. 5, 2021, 79 pages.

*Lumenis Ltd. v. BTL Healthcare Technologies A.S.*, PTAB-IPR2021-01278, Declaration of Dr. Marom Bikson (EX1002), Aug. 13, 2021, 255 pages.

*Lumenis Ltd. v. BTL Healthcare Technologies A.S.*, PTAB-IPR2021-01278, U.S. Pat. No. 10,709,894, Petition for Inter Partes Review, Aug. 13, 2021, 85 pages.

*Lumenis Ltd. v. BTL Healthcare Technologies A.S.*, PTAB-IPR2021-01279, Declaration of Dr. Marom Bikson (EX1002), Aug. 5, 2021, 258 pages.

*Lumenis Ltd. v. BTL Healthcare Technologies A.S.*, PTAB-IPR2021-01279, U.S. Pat. No. 10,709,895, Petition for Inter Partes Review, Aug. 5, 2021, 88 pages.

*Lumenis Ltd. v. BTL Healthcare Technologies A.S.*, PTAB-IPR2021-01280, Declaration of Dr. Marom Bikson (EX1002), Aug. 13, 2021, 235 pages.

*Lumenis Ltd. v. BTL Healthcare Technologies A.S.*, PTAB-IPR2021-01280, U.S. Pat. No. 10,478,634, Petition for Inter Partes Review, Aug. 13, 2021, 69 pages.

*Lumenis Ltd. v. BTL Healthcare Technologies A.S.*, PTAB-IPR2021-01282, Declaration of Dr. Marom Bikson (EX1002), Aug. 5, 2021, 267 pages.

*Lumenis Ltd. v. BTL Healthcare Technologies A.S.*, PTAB-IPR2021-01282, U.S. Pat. No. 10,632,321, Petition for Inter Partes Review, Aug. 5, 2021, 89 pages.

*Lumenis Ltd. v. BTL Healthcare Technologies A.S.*, PTAB-IPR2021-01283, Declaration of Dr. Marom Bikson (EX1002), Aug. 5, 2021, 241 pages.

*Lumenis Ltd. v. BTL Healthcare Technologies A.S.*, PTAB-IPR2021-01283, U.S. Pat. No. 10,695,575, Petition for Inter Partes Review, Aug. 5, 2021, 84 pages.

*Lumenis Ltd. v. BTL Healthcare Technologies A.S.*, PTAB-IPR2021-01284, Declaration of Dr. Marom Bikson (EX1002), Aug. 5, 2021, 279 pages.

*Lumenis Ltd. v. BTL Healthcare Technologies A.S.*, PTAB-IPR2021-01284, U.S. Pat. No. 10,709,895, Petition for Inter Partes Review, Aug. 5, 2021, 93 pages.

*Lumenis Ltd. v. BTL Healthcare Technologies A.S.*, PTAB-IPR2021-01285, Declaration of Dr. Marom Bikson (EX1002), Aug. 13, 2021, 249 pages.

*Lumenis Ltd. v. BTL Healthcare Technologies A.S.*, PTAB-IPR2021-01285, U.S. Pat. No. 10,709,894, Petition for Inter Partes Review, Aug. 13, 2021, 79 pages.

Madariaga, V.B., et al., "[Magnetic Stimulation of the Quadriceps: Analysis of 2 Stimulators Used for Diagnostic and Therapeutic Applications]," Archives De Bronconeumologfa, 43(7):411-417, Elsevier Espana, Spain, (Jul. 2007).

Maffiuletti, N.A., et al., "Activation of Human Plantar Flexor Muscles Increases After Electromyostimulation Training," Journal of Applied Physiology 92(4):1383-1392, American Physiological Society, United States (Nov. 2001).

Maffiuletti, N.A., et al., "The Effects of Electromyostimulation Training and Basketball Practice on Muscle Strength and Jumping Ability," International journal of sports medicine 21(6):437-443, Thieme, Germany (Aug. 2000).

MagVenture, Magnetic Stimulation, Accessories Catalogue, Accessories Catalogue, 2011, 54 pages.

Magstim Company Limited, K051864 510(k) Summary, Magstim Rapid and Magstim Super Rapid, All pages (Dec. 2005).

Magstim Company US, LLC, K060847 510(k) Summary, Magstim Model 200-2 with Double 70mm Remote Coil, All pages (Sep. 2006).

(56) References Cited

OTHER PUBLICATIONS

Magstim Corporation US, K992911 510(k) Summary, Magstim Rapid, All pages (Jan. 2000).
MagVenture, MagPro® by MagVenture®, Versatility in Magnetic Stimulation, World Leading Transcranial Magnetic Stimulation Systems, 2011, 6 Pages.
Man, W.D-C., et al., "Magnetic Stimulation for the Measurement of Respiratory and Skeletal Muscle Function," The European Respiratory Journal 24(5):846-60, European Respiratory Society, England (2004).
Manstein, D., et al., "Selective Cryolysis: A Novel Method of Non-Invasive Fat Removal," Lasers in Surgery and Medicine, 40(9):595-604, Wiley-Liss, United States (Nov. 2008).
Mantovani, A., et al., "Applications of Transcranial Magnetic Stimulation to Therapy in Pyschiatry," Psychiatric Times 21(9), Intellisphere, 29 pages (Aug. 2004).
Marek Heinfarth, "Lipostar" dated Jan. 9, 2013, accessed at https://www.youtube.com/watch?v=hZurkn8iU_U, accessed on Dec. 15, 2021.
Markov, M.S., "Pulsed Electromagnetic Field Therapy History, State of the Art and Future," Environment Systems and Decisions 27(4):465-475, Springer (Dec. 2007).
MecoTec Freezing Technology, Presentation Cryoair Whole Body Cryotherapy Chambers, Germany, Jul. 2017, 52 Pages.
Medline, Body Temperature Norms, 2 pages (Year: 2019).
Meka\1vy et al., "Influence of Electro-lipolysis on Lipid Profile and Central Obesity in Obese Premenopausal Women" Bull. Fae. Ph. Th. Cairo Univ., vol. 17, No. (1), dated Jan. 2012, pp. 59-68.
Mettler J.A., et al., "Low-Frequency Electrical Stimulation With Variable Intensity Preserves Torque," Journal of Electromyography and Kinesiology: Official Journal of the International Society of Electrophysiological Kinesiology 42:49-56, Oxford:Elsevier, England (Oct. 2018).
Mogyoros, I., et al., "Strength-Duration Properties of Human Peripheral Nerve," Brain 119(Pt 2):439-447, Oxford University Press, England (Apr. 1996).
Moon, Chi-Woong"Study on the Pulsed Electromagnetic Fields Effect of Adipocyte Decomposition" Final Report of a Middle-grade Researcher Support Project, Inje University, 2017.
Morrissey. M., "Electromyostimulation from a Clinical Perspective," Sports Medicine 6(1):29-41, Springer International, New Zealand (Aug. 1988).
Mustafa, B., "Design and Construction of a Low Cost dsPIC Controller Based Repetitive Transcranial Magnetic Stimulator TMS," Journal of medical systems 34(1):15-24, Kluwer Academic/Plenum Publishers, United States (2010).
Nadler, S.F., et al., "The Physiologic Basis and Clinical Applications of Cryotherapy and Thermotherapy for the Pain Practitioner," Pain Physician, 7(3):395-399, American Society of Interventional Pain Physicians, United States (Jul. 2004).
Nassab, R., "The Evidence Behind Noninvasive Body Contouring Devices," Aesthetic Surgery Journal, 35(3):279-293, Oxford University Press, England (Mar. 2015).
National Institute of Neurological Disorders and Stroke, Epilepsy Information Page, www.ninds.nih.gov/disorders/epilepsy/epilepsy.htm, pp. 1-6 (Feb. 1, 2016).
Neotonus, Inc., K973096 510(k) Summary, Neotonus Model 1000 Muscle Stimulator System, All pages (Jun. 1998).
Neotonus, Inc., K973929 510(k) Summary and FDA Correspondence, Neotonus, All pages (May 1998).
Neuro Star, TMS Therapy, Bringing Hope to Patients with Depression, 2013, 6 Pages.
Neurosofl, Ivanovo, Since 1992, Magnetic Stimulator, NEURO-MS, Technical Manual, Neurosofl Ltd, Ivanovo, Russia, 2006, 67 Pages.
Nexstim NBS System, Navigated Brain Stimulation, Noninvasive, direct cortical mapping, 2012, 5 Pages.
Neyroud, D., et al., "Comparison of Electrical Nerve Stimulation, Electrical Muscle Stimulation and Magnetic Nerve Stimulation to Assess the Neuromuscular Function of the Plantar Flexor Muscles," European journal of applied physiology 115(7):1429-1439, Springer-Verlag, Germany (2015).
Nielsen, J.F., et al., "A New High-frequency Magnetic Stimulator With an Oil-cooled Coil," Journal of Clinical Neurophysiology 12(5):460-467, Lippincott Williams & Wilkins, United States (Sep. 1995).
Non Final Office Action dated Jun. 23, 2017, in U.S. Appl. No. 15/473,390, Schwarz, T., eta/., filed Mar. 29, 2017.
Notice of Allowance dated Jul. 21, 2021 for U.S. Appl. No. 17/087,850 (pp. 1-8).
Notice of Allowance dated May 6, 2020 for U.S. Appl. No. 16/194,800 (pp. 1-8).
Notice of Allowance dated Oct. 8, 2019 for U.S. Appl. No. 15/603,162 (pp. 1-8).
Notice of Allowance dated Mar. 24, 2021 for U.S. Appl. No. 17/087,850 (pp. 1-8).
Novickij, V., et al., "Compact Microsecond Pulsed Magnetic Field Generator for Application in Bioelectronics," Elektronika ir Elektrotechnika 19(8):25-28 (Oct. 2013).
Novickij, V., et al., "Design and Optimization of Pulsed Magnetic Field Generator for Cell Magneto-Permeabilization," Elektronika ir Elektrotechnika (Electronics and Electrical Engineering) 23(2):21-25 (Apr. 2017).
Novickij, V., et al., "Magneto-Permeabilization of Viable Cell Membrane Using High Pulsed Magnetic Field," IEEE Transactions on Magnetics 51(9), All pages (Sep. 2015).
Novickij, V., et al., "Programmable Pulsed Magnetic Field System for Biological Applications," IEEE Transactions on Magnetics 50(11):5 (Nov. 2014).
NPF Electroapparat, Amplipulse-5Br Manual, allegedly accessed on Nov. 18, 2020, All pages.
Neurosoft Ltd., "Neurosofl—Neuro-MS Transcranial Magnetic Simulator Technical Manual," All pages (Nov. 2014).
Obsluze, "Apparatus for High Induction Magnetic Stimulation," 2016, 42 pages.
Obsluze, N.K., Usage Instructions, User's Manual, Device for high-induction magnetic stimulation of type designation: Saluter Moti, 2016,88 Pages.
Office Action dated Aug. 15, 2019 for U.S. Appl. No. 16/194,800 (pp. 1-12).
Office Action dated Jul. 10, 2020 for U.S. Appl. No. 15/678,915 (pp. 1-9).
Office Action dated Jun. 14, 2021 for U.S. Appl. No. 15/786,303 (pp. 1-13).
Office Action dated Jun. 28, 2021 for U.S. Appl. No. 16/727,458 (pp. 1-11).
Office Action dated Oct. 7, 2019 for U.S. Appl. No. 15/678,915 (pp. 1-8).
Oliveira, P.De., et al., "Neuromuscular Fatigue After Low-and Medium-frequency Electrical Stimulation in Healthy Adults," Muscle & Nerve 58(2):293-299, John Wiley & Sons, United States (Aug. 2018).
Operating Manual: Magstim D702 Coil, MOP06-EN, Revision 01, The Magstim Company Limited, Feb. 2012, 14 Pages.
Operating Manual: Magstim Magstim 2002, MOP01-EN, Revision 01, The Magstim Company Limited, Sep. 2011, 25 Pages.
Operating Manual: Magstim, Magstim Alpha Coil Range, MOP11-EN, Revision 01, Oct. 2012, 18 Pages.
Operating Manual: Magstim, Magstim Bistim2 , MOP02-EN, Revision, The Magstim Company Limited, 01, Sep. 2011, 27 Pages.
Operating Manual, MAGSTIM, Model 200, P/N 3001-01, Double 70mm, Remote Coil, P/N 3190-00, The Magstim Company Limited, 2006, 32 pages.
Operating Manual: Magstim R, 2nd, Generation Coil Family, 3100-23-02, Magstim Coils, The Magstim Company Limited, Nov. 2002, 14 Pages.
Operating Manual, Magstim R Air-Cooled Double 70mm Coil System, 1600-23-04, The Magstim Company Limited, 1999, 18 Pages.
Operating Manual: Magstim R, Bistim System, P/N 3234-23-01, The Magstim Company Limited, Nov. 2004, 30 Pages.

(56) References Cited

OTHER PUBLICATIONS

Operating Manual: Magstim R, Coils & Accessories, 1623-23-07, Magstim Coils & Accessories, May 2010, 24 Pages.
Operating Manual: Magstim, RAPID2, P/N 3576-23-09, The Magstim Company LTD, Nov. 2009, 61 Pages.
Operator's Manual: BTL Emsculpt, BTL Industries Ltd, United Kingdom, 2018, 35 pages.
Operator's Manual: BTL, HPM-6000U, BTL Industries Ltd, United Kingdom, Dec. 2016, 36 pages.
Otte, J.S., et al.,"Subcutaneous Adipose Tissue Thickness Alters Cooling Time During Cryotherapy,"Archives of Physical Medicine and Rehabilitation, 83(11):1501-1505, W.B. Saunders, United States (Nov. 2002).
Pain Management Technologies, "Pain Management Technologies Product Catalog," (2012).
Papimi, For Scientific Research, Pap Ion Magnetic Inductor, Presentation, Magnetotherapeutic Device, Nov. 2009, 61 Pages.
Periso SA, CTU mega Diamagnetic Pump 20: Device For Diamagnetic Therapy, CTU Mega 20 Manual, dated Aug. 28, 2019, 44 pages, Pazzallo Switzerland.
Photograph, Alleged Photograph of Components of a Salus Talent Pop Double Device with An Alleged Manufacture date of Nov. 14, 2012, 1 page.
Physiomed, MAG-Expert, Physiomed Manual, Dec. 19, 2012.
Platil, A., "Magnetopneumography Using Optical Position Reference," Sensor Letters 11(1):69-73, ResearchGate (2013).
Podebradsky. K., et al., Clinical study of high-inductive electromagnetic stimulator SALUS talent, 2010, 8 pages.
Pohanka, J., et al., "An Embedded Stereovision System: Aspects of Measurement Precision," 12th Biennial Baltic Electronics Conference, pp. 157-160 (Oct. 2010).
Polk, C., "Therapeutic Applications of Low-Frequency Sinusoidal and Pulsed Electric and Magnetic Fields," The Biomedical Engineering Handbook, vol. 1, 2000, Second edition, CRC Press LLC, pp. 1625-1636.
Polkey M.I., et al., "Functional Magnetic Stimulation of the Abdominal Muscles in Humans," American Journal of Respiratory and Critical Care Medicine 160(2):513-522, American Thoracic Society, United States (Aug. 1999).
Polkey, M.I., et al., "Quadriceps Strength and Fatigue Assessed by Magnetic Stimulation of the Femoral Nerve in Man," Muscle Nerve 19(5):549-555, John Wiley & Sons, United States, (May 1996).
Pollogen, Trilipo MED Procedure, Brochure, dated Apr. 7, 2021, 76 pages.
Pollogen, Maximus Non-invasive body shaping System, User Manual, dated May 1, 2012, 44 pages, http://download.lifvation.com/Maximus_UserManual.pdf.
Porcari, J.P., et al., "Effects of Electrical Muscle Stimulation on Body Composition, Muscle Strength, and Physical Appearance," Journal of Strength and Conditioning Reasearch 16(2):165-172, Human Kinetics Pub., United States (May 2002).
Porcari, J.P., et al., "The Effects of Neuromuscular Electrical Stimulation Training on Abdominal Strength, Endurance, and Selected Anthropometric Measures," Journal of Sports Science and Medicine 4(1):66-75, Dept. of Sports Medicine, Turkey (Mar. 2005).
Pribula, 0. and Fischer, J., "Real Time Precise Position Measurement Based on Low-Cost CMOS Image Sensor," IEEE, 5 pages (2011).
Pribula, 0., et al., "cost-effective Image Acquisition System for Precise Pc-based Measurements," Przeglad Elektrotechniczny (Electrical Review), 259-263, 2011.
Pribula, 0., et al., "Optical Position Sensor Based on Digital Image Processing: Magnetic Field Mapping Improvement," Radioengineering 20 (1):55-60, (Apr. 2011).
Pribula, 0., et al., "Real-Time Video Sequences Matching Spatio-Temporal Fingerprint," IEEE, 911-916 (Jun. 2010).
Prouza, 0., et al., "High-Intensity Electromagnetic Stimulation Can Reduce Spasticity in Post-Stroke Patients," International Journal of Physiotherapy 5(3):87-91 (2018).
Prouza, 0., "Ex-Post Analyza Spot Rebnich Dani," All pages, (2008).
Prouza, 0., "Targeted Radiofrequency Therapy for Training Induced Muscle Fatigue—Effective or Not?," International Journal of Physiotherapy 3(6):707-710 (Dec. 2016).
PTAB-IPR2021-00296, U.S. Pat. No. 10,493,293, Petition for Inter Partes Review, Dec. 14, 2020, 117 pages.
PTAB-IPR2021-00312, U.S. Pat. No. 10,478,634, Petition for Inter Partes Review, Dec. 14, 2020, 108 pages.
PTAB-PGR2021-00015, U.S. Pat. No. 10,709,895, Petition for Post-Grant Review, Dec. 14, 2020, 140 pages.
PTAB-PGR2021-00016, U.S. Pat. No. 10,709,895, Petition for Post-Grant Review, Dec. 14, 2020, 144 pages.
PTAB-PGR2021-00017, U.S. Pat. No. 10,632,321, Petition for Post-Grant Review, Dec. 14, 2020, 121 pages.
PTAB-PGR2021-00018, U.S. Pat. No. 10,632,321, Petition for Post-Grant Review, Dec. 14, 2020, 140 pages.
PTAB-PGR2021-00020, U.S. Pat. No. 10,695,575, Petition for Post-Grant Review, Dec. 14, 2020, 112 pages.
PTAB-PGR2021-00021, U.S. Pat. No. 10,695,575, Petition for Post-Grant Review, Dec. 14, 2020, 117 pages.
PTAB-PGR2021-00022, U.S. Pat. No. 10,709,894, Petition for Post-Grant Review, Dec. 14, 2020, 119 pages.
PTAB-PGR2021-00023, U.S. Pat. No. 10,709,894, Petition for Post-Grant Review, Dec. 14, 2020, 136 pages.
PTAB-PGR2021-00024, U.S. Pat. No. 10,695,576, Petition for Post-Grant Review, Dec. 14, 2020, 136 pages.
PTAB-PGR2021-00025, U.S. Pat. No. 10,695,576, Petition for Post-Grant Review, Dec. 14, 2020, 135 pages.
Publication of Medical Device Manufacturing Approval of Salus-TALENT-Pro, approval date Mar. 11, 2014, 39 pages.
Quick Start Manuals, Magstim Super Rapid Plus Quick Start, Aalto TMS Laboratory, Aalto School of Science, 2013, 7 Pages.
Radakovic T. and Radakovic N., "The Effectiveness of the Functional Magnetic Stimulation Therapy in Treating Sciatica Syndrome," Open Journal of Therapy and Rehabilitation 3(3):63-69 (2015).
Reaction User Manual, Viora, Doc No. MK-004 A, 2008, 53 Pages.
Reshaping the Future of Your Practice, Cool sculpting, A Revolution in Aesthetic Fat Reduction, 2011, 10 Pages.
Riehl., M., "Chapters: TMS Stimulator Design" The Oxford Handbook of Transcranial Stimulation, Wasserman, E.M., ed., pp. 13-23, Oxford University Press, 26 pages, United Kingdom (2008).
Roots, H., and Ranatunga, K.W., "An Analysis of the Temperature Dependence of Force, During Steady Shortening at Different Velocities, in (Mammalian) Fast Muscle Fibres," Journal of Muscle Research and Cell Motility 29(1):9-24, Springer, Netherlands (Jun. 2008).
Ruiz-Esparza, J. and J. Barba Gomez., "The Medical Face Lift: A Noninvasive, Nonsurgical Approach to Tissue Tightening in Facial Skin Using Nonablative Radiofrequency," Dermatologic Surgery 29(4):325-332, Williams & Wilkins, United States (Apr. 2003).
Russian excerpt of Werner, R., Magnetotherapy, Pulsating energy resonance therapy, 41-67 (Jun. 2007).
Rutkove, S., "Effects of Temperature on Neuromuscular Electro physiology," Muscle & Nerve 24(7):867-882, John Wiley & Sons, United States (Jul. 2001).
Salus Talent Pop, The first sales bill, Authorization No. 20120221-41000096-66667961, 2 pages, (Feb. 2012).
Salus Talent-A, Remed, User Guide, High Intensity Electro Magnetic Field Therapy, 2017, 37 pages.
Sargeant, A.J., "Effect of Muscle Temperature on Leg Extension Force and Short-term Power Output in Humans," European Journal of Applied Physiology and Occupational Physiology 56(6):693-698, Springer Verlag, Germany (Sep. 1987).
Schaefer, D.J., et al., "Review of Patient Safety in Time-Varying Gradient Fields," Journal of Magnetic Resonance Imaging 12:20-29, Wiley-Liss, United States (Jul. 2000).
Shimada, Y., et al., "Effects of therapeutic magnetic stimulation on acute muscle atrophy in rats after hindlimb suspension," Biomedical Research 27(1):23-27, Biomedical Research Foundation, Japan (Feb. 2006).

(56) References Cited

OTHER PUBLICATIONS

Silinskas, V., et al., "Effect of Electrical Myostimulation on the Function of Lower Leg Muscles," Journal of strength and Conditioning Research 31(6):1577-1584, Human Kinetics Pub, United States (2017).
Sport-Elec S.A., K061914 510(k) Summary, Sport-Elec, All pages (Jul. 2007).
Sport-Elec S.A., K081026 510(k) Summary, Sport-Elec, All pages (Nov. 2008).
Starbelle, PEMF Shape, Webpage, dated Feb. 10, 2020, 3 pages, available at http://www.starbelle.cn/info/PEMFShape.html.
Stedman, T.L., "Aponeurosis—Apparatus," in Stedman's Medical Dictionary, 27th Edition, Pugh, M.B., ed., pp. 113-114, Lippincott Williams & Wilkins, Baltimore, MD (2000).
Stevens, J.E., et al., "Neuromuscular Electrical Stimulation for Quadriceps Muscle Strengthening After Bilateral Total Knee Arthroplasty: A Case Series," Journal of Orthopaedic and Sports Physical Therapy 34(1):21-29, Williams And Wilkins, United States (Jan. 2004).
Struppler, A., et al., "Facilitation of Skilled Finger Movements by Repetitive Peripheral Magnetic Stimulation (RPMS)—A New Approach In Central Paresis.," NeuroRehabilitation 18(1):69-82, IOS Press, Amsterdam (2003).
Struppler, A., et al., "Modulatory Effect of Repetitive Peripheral Magnetic Stimulation on Skeletal Muscle Tone in Healthy Subjects: Stabilization of the Elbow Joint," Experimental Brain Research 157(1):59-66, Springer Verlag, Germany (Feb. 2004).
Suarez-Bagnasco, D., et al., "The Excitation Functional for Magnetic Stimulation of Fibers.," Annual International Conference of the IEEE Engineering in Medicine and Biology Society, IEEE Engineering in Medicine and Biology Society, Annual International Conference, 2010:4829-4833, IEEE, United States (2010).
Swallow, E.B., et al., "A Novel Technique for Nonvolitional Assessment of Quadriceps Muscle Endurance in Humans," Journal of Applied Physiology 103(3):739-746, American Physiological Society, United States (Sep. 2007).
Szecsi, J., et al., "A Comparison of Functional Electrical and Magnetic Stimulation for Propelled Cycling of Paretic Patients," Archives of Physical Medicine and Rehabilitation 90(4):564-570, W.B. Saunders, United States, (Apr. 2009).
Szecsi, J., et al., "Force-pain Relationship in Functional Magnetic and Electrical Stimulation of Subjects With Paresis and Preserved Sensation," Clinical Neurophysiology 121(9):1589-1597, Elsevier, Netherlands, (Sep. 2010).
Taylor, J.L, "Magnetic Muscle Stimulation Produces Fatigue Without Effort," Journal of Applied Physiology (1985) 103(3):733-734, American Physiological Society, United States, (Sep. 2007).
Tesla Stym, Iskra Medical, Tone the inner muscle with FMS Functional Magnetic Stimulation, 2013, 4 pages.
The Burn Centre Care, Education, 3 pages, printed from internet Nov. 13, 2017.
The Magstim Company Ltd, K080499 510(k) Summary, Magstim Double 70mm Air Film Coil, All pages (Dec. 2008).
The Magstim Company Ltd., K130403 510(k) Summary, Magstim D702 coil, All pages (Aug. 2013).
Thermi Launches Arvati, powered by Thermi, with newest advances in True Temperature Controlled Radiofrequency Technology, 5 pages (2018).
Thompson, M.T., "Inductance Calculation Techniques—Part II: Approxmiations and Handbook Methods," Power Control and Intelligent Motion, 11 pages (Dec. 1999) http://www.pcim.com/.
Thompson, M.T., "Inductance Calculation Techniques—Part II: Classical Methods," Power Control and Intelligent Motion, 25(12):40-45, (Dec. 1999) http://www.pcim.com/.
Tomek, J., et al., "Magnetopneumography—Incorporation of optical position reference," Journal of Electrical Engineering, All pages (2012).
Torbergsen, T., "Abstracts of the International Course and Symposium in Single Fibre EMG and Quantitative EMG Analysis. Troms0, Norway, Jun. 4-8, 1984," Muscle & Nerve 9(6):562- 574, John Wiley & Sons, United States (Jul.-Aug. 1986).
Trifractional FAQs, http://pollogen.lifvation.com/FAQ/TriFractional%20FAQs.pdf, Aug. 2011 (4pages).
TriLipo MED Procedure, http://download.lifvation.com/Maximus_TrilipoMED_Intro.pdf, Apr. 2013, 76 pages.
TSEM Med Swiss SA, Diamagnetic Therapy: A Revolutionary Therapy, CTU Mega 20 Catalogue, dated 2016, 24 pages, Lugano Switzerland.
Turley, J., "Agilent Technologies Announces 30 MHz Function/Arbitrary Waveform Generators with Unparalleled Signal Accuracy," Elec. Eng'g J., URL: (Aug. 4, 2010), 8 pages.
Ultra Slim Professional, The very best body Contouring, Wardphotonics LLC, 2018, 16 pages.
U.S. Appl. No. 60/848,720, inventor Burnett, D., filed Sep. 30, 2006 (Not Published).
U.S. Appl. No. 62/331,060, inventor Schwarz, T., filed May 3, 2016 (Not Published).
U.S. Appl. No. 62/331,072, inventor Schwarz, T., filed May 3, 2016 (Not Published).
U.S. Appl. No. 62/331,088, inventor Schwarz, T., filed May 3, 2016 (Not Published).
U.S. Appl. No. 62/333,666, inventor Schwarz, T., filed May 9, 2016 (Not Published).
U.S. Appl. No. 62/351,156, inventor Schwarz, T., filed Jun. 16, 2016 (Not Published).
U.S. Appl. No. 62/357,679, inventor Schwarz, T., filed Jul. 1, 2016 (Not Published).
U.S. Appl. No. 62/440,905, inventors Schwarz, T. et al., filed Dec. 30, 2016 (Not Published).
U.S. Appl. No. 62/440,912, inventors Schwarz, T. et al., filed Dec. 30, 2016 (Not Published).
U.S. Appl. No. 62/440,922, inventor Schwarz, T., filed Dec. 30, 2016 (Not Published).
U.S. Appl. No. 62/440,936, inventor Schwarz, T., filed Dec. 30, 2016 (Not Published).
U.S. Appl. No. 62/440,940, inventor Schwarz, T., filed Dec. 30, 2016 (Not Published).
U.S. Appl. No. 62/441,805, inventor Prouza, 0., filed Jan. 3, 2017 (Not Published).
U.S. Appl. No. 62/786,731, inventor Schwarz, T., filed Dec. 31, 2018 (Not Published).
User Guide: Mag Venture, Magpro family, MagPro R30, MagPro R30 with MagOption, MagPro X100, MagPro X100 with MagOption, MagPro software v.5.0, US-edition, MagPro family User Guide, 2010, 52 Pages.
User Guide, Salus Talent Pro, REMED, High Intensity Electro magnetic Field Therapy-2 Channel, 2017, Version M-1.0.0, 45 pages.
User Guide, Salus Talent, REMED, High Intensity Electro magnetic Field Therapy, Version. M-1.0.0, 2017, 40 pages.
User's Manual: BTL-6000, Super Inductive System Elite, BBTL Industries Ltd, United Kingdom, Sep. 2016, 36 pages.
User Manual: Electro-magnetic Stimulator, Salus-Talent, Version 1.00, Rehabilitation Medical Company,2013, 34 Pages.
User Manual: Regenetron PRO, System Information, Regenetron PRO User Manual, Nov. 2014, 7 Pages.
Vance, C., et al., "Effects of Transcutaneous Electrical Nerve Stimulation on Pain, Pain Sensitivity, and Function in People with Knee Osteoarthritis," Physical Therapy 92:898-910 (2012).
Vanquish Operator's Manual, BTL, 2012, 48 Pages.
Venus, Venus legacy marca argentina, Oct. 14, 2014, 20 pages.
Venus Concept Ltd., VenusFreeze MP2, User Manual, dated Jun. 2012, 46 pages.
Venus Concept Ltd., VenusViva, User Manual, dated Aug. 2013, 51 pages.
Venus Legacy, User Manual International, 2009, Venus Concept, 49 pages.
Venus Swan, Experience the Difference, Venus Concept, Delivering the Promise, http://www.medicom.cz/UserFiles/File/LekarskeNenue/020Swan%20EN.pdf, 2 pages (Apr. 2016).

(56) References Cited

OTHER PUBLICATIONS

Verges S., et al., "Comparison of Electrical and Magnetic Stimulations to Assess Quadriceps Muscle Function," Journal of Applied Physiology (1985) 106(2):701-710, American Physiological Society, United States, (Feb. 2009).

Wada, K., et al., "Design and Implementation of Multi-Frequency Magnetic Field Generator Producing Sinusoidal Current Waveform for Biological Researches," IEEE, 9 pages (2016).

Wanitphakdeedecha, R., et al., "Treatment of Abdominal Cellulite and Circumference Reduction With Radiofrequency and Dynamic Muscle Activation" Journal of Cosmetic and Laser Therapy 17(5):246-251, Informa Healthcare, England (2015).

Ward, A.R. and Shkuratova, N., "Russian Electrical Stimulation: The Early Experiments," Physical therapy 82(10):1019-1030, Oxford University Press, United States (2002).

Wasilewski, M.L., Academy of Aesthetic and Anti-Aging Medicine, Application of magnetic fields with deep stimulation in the fight against local obesity of lower limbs, BTL, 2012, 4 pages.

Web MD, what is normal body temperature? 3 pages, printed Mar. 4, 2019.

Weight to volume aluminum, 2 pages printed from internet Sep. 25, 2018.

Weight to volume copper, 2 pages printed from internet Sep. 25, 2018.

Weiss, R.A., et al., "Induction of Fat Apoptosis by a Non-Thermal Device: Mechanism of Action of Non-Invasive High-Intensity Electromagnetic Technology in a Porcine Model," Lasers in surgery and medicine 51(1):47-53, Wiley-Liss, United States (Jan. 2019).

Weng, 0., "Electromagnetic Activation of the Calf Muscle Pump," UMI Dissertation Publishing (2014).

Woehrle, J., et al., "Dry Needling and its Use in Health Care—A Treatment Modality and Adjunct for Pain Management," Journal of Pain & Relief 4(5): 1-3, (Aug. 2015).

Yacyshy, A.F., et al., "The Inclusion of Interstimulus Interval Variability Does Not Mitigate Electrically-evoked Fatigue of the Knee Extensors," European Journal of Applied Physiology 120(12):2649-2656, Springer-Verlag, Germany (Sep. 2020).

Zao 0KB Ritm, Electroneurostimulants, Transdermal Scenar-NT Instructions, All Pages (Nov. 2013).

Zao 0KB Ritm, Percutaneous Electrical Stimulators With Individual Biofeedback Dosing Impact on Reflex Zones, All pages (2017).

Zelickson, B., et al.,"Cryolipolysis For Noninvasive Fat Cell Destruction: Initial Results From a Pig Model," Dermatologic Surgery 35(10):1462-1470, Hagerstown, MD Lippincott, Williams & Wilkins, United States (Oct. 2009).

Zeltiq System User Manual—Print and Binding Specifications, Zeltiq Aesthetics, Inc, Mar. 2011, 88 pages.

Zerona R-Z6 by Erchonia, Specifications, Retrieved from the Internet: (www.myzerona.com), 2015, 1 page.

Zhang, G., et al., "A Method of Nerve Electrical Stimulation by Magnetic Induction," Annual International Conference of the IEEE Engineering in Medicine and Biology Society 2009:622-625, IEEE, United States (2009).

Zhi-De, D., "Electromagnetic Field Modeling of Transcranial Electric and Magnetic Stimulation: Targeting, Individualization, and Safety of Convulsive and Subconvulsive Applications," Academic Commons (2013).

Zhu, Y., et al., "Magnetic Stimulation of Muscle Evokes Cerebral Potentials by Direct Activation of Nerve Afferents: A Study During Muscle Paralysis," Muscle & Nerve 19(12):1570-1575, John Wiley & Sons, United Sates (Dec. 1996).

Pascual-Leone, Alvaro et al. "Handbook of Transcranial Magnetic Stimulation" 2002 Arnold Publishers, Chapters 1-4, 58 pages.

Mantis, The non-invasive solution that restores natural beauty, improves health, and offers a renewed psychophysical sense of balance, MR991 theramagnetic, 2020, 8 pages.

Mantis Theramagnetic Compact: the compact that guarantees utmost efficiency and maximum performance, theramagnetic, 2020, 8 pages.

Pollegen, K200545, Legend Pro OMA, Indications for use, dated Oct. 20, 2021,11 pages.

Jalinous, R., "Technical and Practical Aspects of Magnetic Nerve Stimulation," Journal of Clinical Neurophysiology 8(1):10-25, Lippincott Williams & Wilkins, United States (Jan. 1991).

*Lumenis Be Ltd. v. BTL Healthcare Technologies A.S.*, PTAB-IPR2022-00451, Declaration of Dr. Marom Bikson (EX1002), Jan. 24, 2022, 236 pages.

*Lumenis Be Ltd. v. BTL Healthcare Technologies A.S.*, PTAB-IPR2022-00451, U.S. Pat. No. 10,806,943 Petition for Inter Partes Review, Jan. 24, 2022, 87 pages.

*Lumenis Be Ltd. v. BTL Healthcare Technologies A.S.*, PTAB-IPR2022-00452, Declaration of Dr. Marom Bikson (EX1002), Jan. 24, 2022, 229 pages.

*Lumenis Be Ltd. v. BTL Healthcare Technologies A.S.*, PTAB-IPR2022-00452, U.S. Pat. No. 10,806,943 Petition for Inter Partes Review, Jan. 24, 2022, 81 pages.

Operating Manual: Magstim® 2002, P/N 3001-23-04, The Magstim Company Limited, Mar. 18, 2005, 34 pages.

Stallknecht, B., et al., "Are Blood Flow and Lipolysis in Subcutaneous Adipose Tissue Influenced by Contractions in Adject Muscles in Humans?," American Journal of Physiology. Endocrinology and Metabolism 292(2):E394-E399, American Physiological Society, United States (Feb. 2007).

Weyh, T., et al., "Marked Differences in the Thermal Characteristics of Figure-of-eight Shaped Coils Used for Repetitive Transcranial Magnetic Stimulation," Clinical Neurophysiology 116(6):1477-1486, Elsevier, Netherlands (Mar. 2005).

* cited by examiner

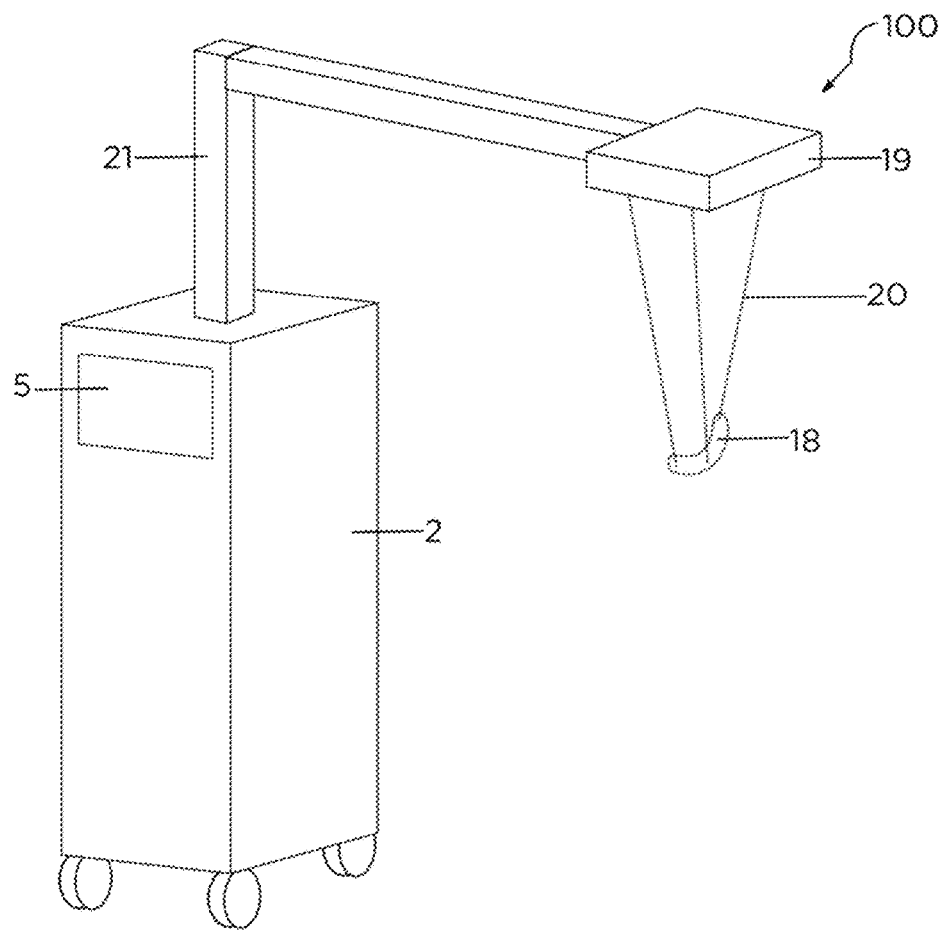
Fig. 8
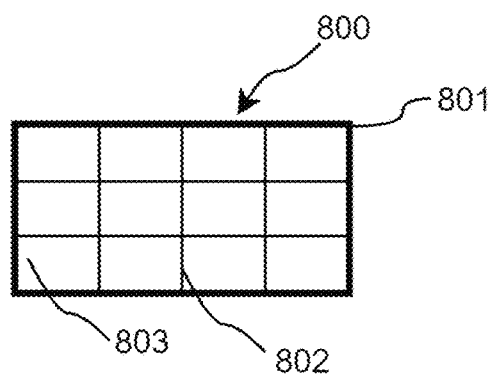 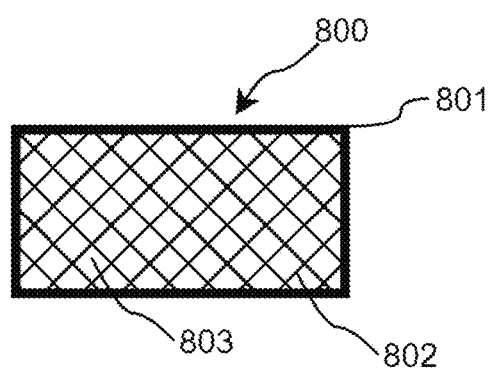
Fig. 9A Fig. 9B

DEVICE AND METHOD FOR UNATTENDED TREATMENT OF A PATIENT

CROSS-REFERENCE TO RELATED APPLICATIONS

This application is a continuation of U.S. application Ser. No. 17/664,161, filed May 19, 2022, now pending, which is a continuation-in-part of U.S. application Ser. No. 17/518,243, filed Nov. 3, 2021, now pending, which is a continuation-in-part of International Application No. PCT/IB2021/000300, filed May 3, 2021, now pending, which claims priority to U.S. Provisional Application No. 63/019,619, filed on May 4, 2020, all of which are incorporated herein by reference in their entirety.

FIELD OF THE INVENTION

The present invention relates to methods and apparatus for patient treatment by means of active elements delivering electromagnetic energy and/or secondary energy in such a way that the treatment area is treated homogeneously without the need for manipulation of the active elements during the therapy.

BACKGROUND OF THE INVENTION

Skin ages with time mostly due to UV exposure—a process known as photoaging. Everyday exposure to UV light gradually leads to decreased skin thickness and a lower amount of the basic building proteins in the skin—collagen and elastin. The amounts of a third major skin component are also diminished, those of hyaluronic acid. These changes appear more quickly on the visible parts of the body, most notably the face. There are several technologies used for facial non-invasive skin rejuvenation such as lasers, high-intensity focused ultrasound and radiofrequency. It is expected that the ultrasound and RF fields also lead to an increase in levels of hyaluronic acid in the dermis.

Delivering various forms of electromagnetic energy into a patient for medical and cosmetic purposes has been widely used in the past. These common procedures for improvement of a visual appearance include, but are by no means limited to, skin rejuvenation, wrinkle removal, rhytides, skin tightening and lifting, cellulite and fat reduction, treatment of pigmented lesions, tattoo removal, soft tissue coagulation and ablation, vascular lesion reduction, face lifting, muscle contractions and muscle strengthening, temporary relief of pain, muscle spasms, increase in local circulation etc.

Besides many indisputable advantages of thermal therapies, these procedures also bring certain limitations and associated risks. Among others is the limited ability of reproducible results as these are highly dependent on applied treatment techniques and the operator's capabilities. Moreover, if the therapy is performed inappropriately, there is an increased risk of burns and adverse events.

It is very difficult to ensure a homogeneous energy distribution if the energy delivery is controlled via manual movement of the operator's hand which is the most common procedure. Certain spots can be easily over- or under-treated. For this reason, devices containing scanning or other mechanisms capable of unattended skin delivery have emerged. These devices usually deliver energy without direct contact with the treated area, and only on a limited, well-defined area without apparent unevenness. Maintaining the same distance between the treated tissue and the energy generator or maintaining the necessary tissue contact may be challenging when treating uneven or rugged areas. Therefore, usage of commonly available devices on such specific areas that moreover differ from patient to patient (e.g. the face) might be virtually impossible.

Facial unattended application is, besides the complications introduced by attachment to rugged areas and necessity of adaptation to the shapes of different patients, specific by its increased need for protection against burns and other side effects. Although the face heals more easily than other body areas, it is also more exposed, leading to much higher requirements for treatment downtime. Another important aspect of a facial procedure is that the face hosts the most important human senses, whose function must not be compromised during treatment. Above all, eye safety must be ensured throughout the entire treatment.

The current aesthetic market offers either traditional manually controlled radiofrequency or light devices enabling facial tissue heating to a target temperature in the range of 40° C.-100° C. or unattended LED facial masks whose operation is based on light effects (phototherapy) rather than thermal effects. These masks are predominantly intended for home use and do not pose a risk to patients of burns, overheating or overtreating. The variability in facial shapes of individual patients does not represent any issue for these masks as the delivered energy and attained temperatures are so low that the risk of thermal tissue damage is minimized and there is no need for homogeneous treatment. Also, due to low temperatures, it is not important for such devices to maintain the predetermined distance between the individual diodes and the patient's skin, and the shape of the masks is only a very approximate representation of the human face. But their use is greatly limited by the low energy and minimal to no thermal effect and they are therefore considered as a preventive tool for daily use rather than a method of in-office skin rejuvenation with immediate effect.

Nowadays, the aesthetic market feels the needs of the combination of the heating treatment made by electromagnetic energy delivered to the epidermis, dermis, hypodermis or adipose tissue with the secondary energy providing muscle contraction or muscle stimulation in the field of improvement of visual appearance of the patient. However, none of the actual devices is adapted to treat the uneven rugged areas like the face. In addition, the commercially available devices are usually handheld devices that need to be operated by the medical professional during the whole treatment.

Thus it is necessary to improve medical devices providing more than one treatment energy (e.g. electromagnetic energy and electric current), such that both energies may be delivered via different active elements or the same active element (e.g. electrode). Furthermore, the applicator or pad of the device needs to be attached to the patient which allows unattended treatment of the patient and the applicator or pad needs to be made of flexible material allowing sufficient contact with the uneven treatment area of the body part of the patient.

SUMMARY OF THE INVENTION

In order to enable well defined unattended treatment of the uneven, rugged areas of a patient (e.g. facial area) while preserving safety, methods and devices of minimally invasive to non-invasive electromagnetic energy delivery via a single or a plurality of active elements have been proposed.

The patient may include skin and a body part, wherein a body part may refer to a body area.

The desired effect of the improvement of visual appearance of the patient may include tissue (e.g. skin) heating in the range of 37.5° C. to 55° C., tissue coagulation at temperatures of 50° C. to 70° C., or tissue ablation at temperatures of 55° C. to 130° C. depending on the patient. Various patients and skin conditions may require different treatment approaches—higher temperatures allow better results with fewer sessions but require longer healing times while lower temperatures enable treatment with no downtime but limited results within more sessions. Another effect of the heating may lead to decreasing the number of the fat cells.

Another desired effect may be muscle contraction causing muscle stimulation (e.g. strengthening or toning) for improving the visual appearance of the patient.

An arrangement for contact or contactless therapy has been proposed.

For contact therapy, the proposed device and methods comprise at least one electromagnetic energy generator inside a main unit that generates an electromagnetic energy which is delivered to the treatment area via at least one active element attached to the skin. At least one active element may be embedded in a pad made of flexible material that adapts to the shape of the rugged surface. An underside of the pad may include an adhesive layer allowing the active elements to adhere to the treatment area and to maintain necessary tissue contact. Furthermore, the device may employ a safety system capable of adjusting one or more therapy parameters based on the measured values from at least one sensor, e.g. thermal sensors or impedance measurement sensors capable of measuring quality of contact with the treated tissue.

For contactless therapy, the proposed device and methods comprise at least one electromagnetic energy generator inside a main unit that generates an electromagnetic energy which is delivered to the treatment area via at least one active element located at a defined distance from the tissue to be treated. A distance of at least one active element from the treatment area may be monitored before, throughout the entire treatment or post-treatment. Furthermore, the device may employ a safety system capable of adjusting one or more therapy parameters based on the measured values from at least one sensor, for example one or more distance sensors. Energy may be delivered by a single or a plurality of static active elements or by moving a single or a plurality of active elements throughout the entire treatment area, for example via a built-in automatic moving system, e.g. an integrated scanner. Treatment areas may be set by means of laser sight—the operator may mark the area to be treated prior to the treatment.

The active element may deliver energy through its entire surface or by means of a so-called fractional arrangement when the active part includes a matrix formed by points of defined size. These points may be separated by inactive (and therefore untreated) areas that allow faster tissue healing. The points surface may make up from 1% to 99% of the active element area.

The electromagnetic energy may be primarily generated by a laser, laser diode module, LED, flash lamp or incandescent light bulb or by radiofrequency generator for causing the heating of the patient. Additionally, an acoustic energy or electric or electromagnetic energy, which does not heat the patient, may be delivered simultaneously, alternately or in overlap with the primary electromagnetic energy.

Additionally, the heating of the patient may be provided by a heated fluid, magnetic field, ultrasound, or by a heating element (e.g. resistance wire or thermoelectric cooler (TEC)).

The active element may deliver more than one energy simultaneously (at the same time), successively or in overlap. For example, the active element may deliver a radiofrequency energy and subsequently an electric energy (electric current). In another example, the active element may deliver the radiofrequency energy and the electric energy at the same time.

Furthermore the device may be configured to deliver the electromagnetic field by at least one active element and simultaneously (at the same time) deliver e.g. electric energy by a different elements.

The proposed methods and devices may provide heating of tissue, contractions of muscles or the combination of heating and muscle contractions.

In one aspect, the proposed device may provide three different types of energies. For example, radiofrequency energy, electric current, and magnetic field; radiofrequency energy, electric current, and pressure pulses; radiofrequency energy, magnetic field, and pressure pulses; or any other possible combinations of energies provided by the proposed device.

Thus the proposed methods and devices may lead to improvement of a visual appearance including, but by no means limited to a proper skin rejuvenation, wrinkle removal, skin tightening and lifting, cellulite and fat reduction, treatment of pigmented lesions, rhytides, tattoo removal, soft tissue coagulation and ablation, vascular lesions reduction, temporary relief of pain, muscle spasms, increase in local circulation, etc. of uneven rugged areas without causing further harm to important parts of the patient's body, e.g. nerves or internal organs. The proposed method and devices may lead to an adipose tissue reduction, e.g. by fat cells lipolysis or apoptosis.

Furthermore, the proposed methods and devices may lead to improvement of a visual appearance, e.g. tissue rejuvenation via muscle strengthening or muscle toning through muscle contractions caused by electric current or electromagnetic energy and via elastogenesis and/or neocollagenesis and/or relief of pain and/or muscle spasms and/or increase in local circulation through heating by radiofrequency energy.

Alternatively, the proposed devices and methods may be used for post-surgical treatment, e.g. after liposuction, e.g. for treatment and/or healing of the wounds caused by surgery.

BRIEF DESCRIPTION OF THE DRAWINGS

FIG. 8 is an illustration of an apparatus for contactless therapy.

FIG. 9A is an illustration of the framed grated electrode.

FIG. 9B is an illustration of another framed grated electrode.

DETAILED DESCRIPTION

Figure 1:
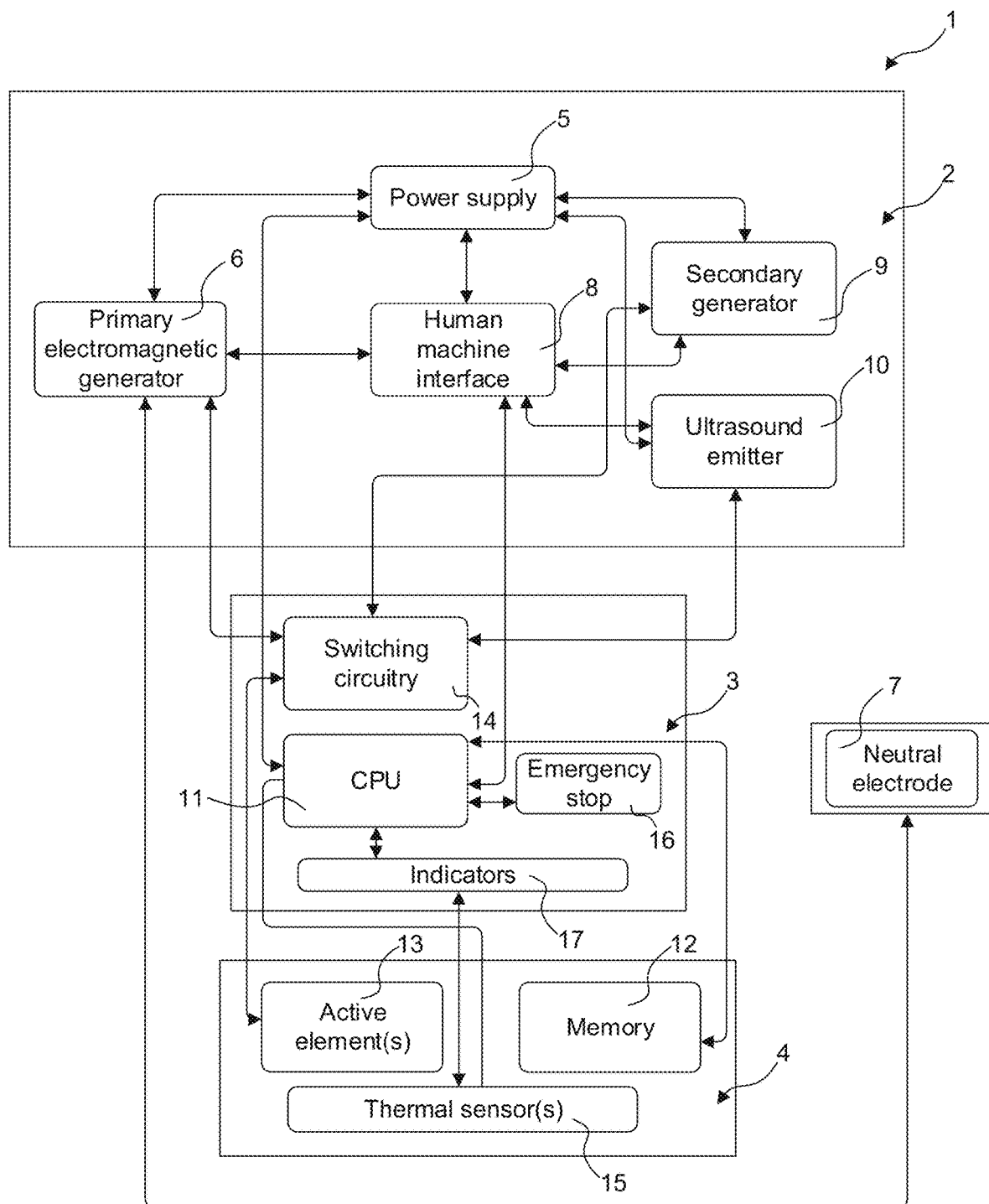
FIG. 1 shows a block diagram of an apparatus for contact therapy.

The presented methods and devices may be used for stimulation and/or treatment of a tissue, including but not limited to skin, epidermis, dermis, hypodermis or muscles. The proposed apparatus is designed for minimally to non-invasive treatment of one or more areas of the tissue to enable well defined unattended treatment of the uneven, rugged areas (e.g. facial area) by electromagnetic energy delivery via a single or a plurality of active elements without causing further harm to important parts of the patient's body, e.g. nerves or internal organs.

Additionally the presented methods and devices may be used to stimulate body parts or body areas like head, neck, bra fat, love handles, torso, back, abdomen, buttocks, thighs, calves, legs, arms, forearms, hands, fingers or body cavities (e.g. vagina, anus, mouth, inner ear etc.).

The proposed methods and devices may include a several protocols improving of visual appearance, which may be preprogramed in the control unit (e.g. CPU—central processing unit, which may include a flex circuit or a printed circuit board and may include a microprocessor or memory for controlling the device).

The desired effect may include tissue (e.g. a surface of the skin) heating (thermal therapy) in the range of 37.5° C. to 55° C. or in the range of 38° C. to 53° C. or in the range of 39° C. to 52° C. or in the range of 40° C. to 50° C. or in the range of 41° C. to 45° C., tissue coagulation at temperatures in the range of 50° C. to 70° C. or in the range of 51° C. to 65° C. or in the range of 52° C. to 62° C. or in the range of 53° C. to 60° C. or tissue ablation at temperatures in the range of 55° C. to 130° C. or in the range of 58° C. to 120° C. or in the range of 60° C. to 110° C. or in the range of 60° C. to 100° C. The device may be operated in contact or in contactless methods. For contact therapy a target temperature of the skin may be typically within the range of 37.5° C. to 95° C. or in the range of 38° C. to 90° C. or in the range of 39° C. to 85° C. or in the range of 40° C. to 80° C. while for contactless therapy a target temperature of the skin may be in the range of 37.5° C. to 130° C. or in the range of 38° C. to 120° C. or in the range of 39° C. to 110° C. or in the range of 40° C. to 100° C. The temperature within the range of 37.5° C. to 130° C. or in the range of 38° C. to 120° C. or in the range of 39° C. to 110° C. or in the range of 40° C. to 100° C. may lead to stimulation of fibroblasts and formation of connective tissue—e.g. collagen, elastin, hyaluronic acid etc. Depending on the target temperature, controlled tissue damage is triggered, physiological repair processes are initiated, and new tissue is formed. Temperatures within the range of 37.5° C. to 130° C. or in the range of 38° C. to 120° C. or in the range of 39° C. to 110° C. or in the range of 40° C. to 100° C. may further lead to changes in the adipose tissue. During the process of apoptosis caused by high temperatures, fat cells come apart into apoptotic bodies and are further removed via the process of phagocytosis. During a process called necrosis, fat cells are ruptured due to high temperatures, and their content is released into an extracellular matrix. Both processes may lead to a reduction of fat layers enabling reshaping of the face. Removing fat from the face may be beneficial for example in areas like submentum or cheeks.

Another desired effect may include tissue rejuvenation, e. g. muscle strengthening through the muscle contraction caused by electric or electromagnetic energy, which doesn't heat the patient, or the muscle relaxation caused by a pressure massage. The combined effect of muscle contractions via electric energy and tissue (e.g. skin) heating by electromagnetic field in accordance to the description may lead to significant improvement of visual appearance.

Figure 2:
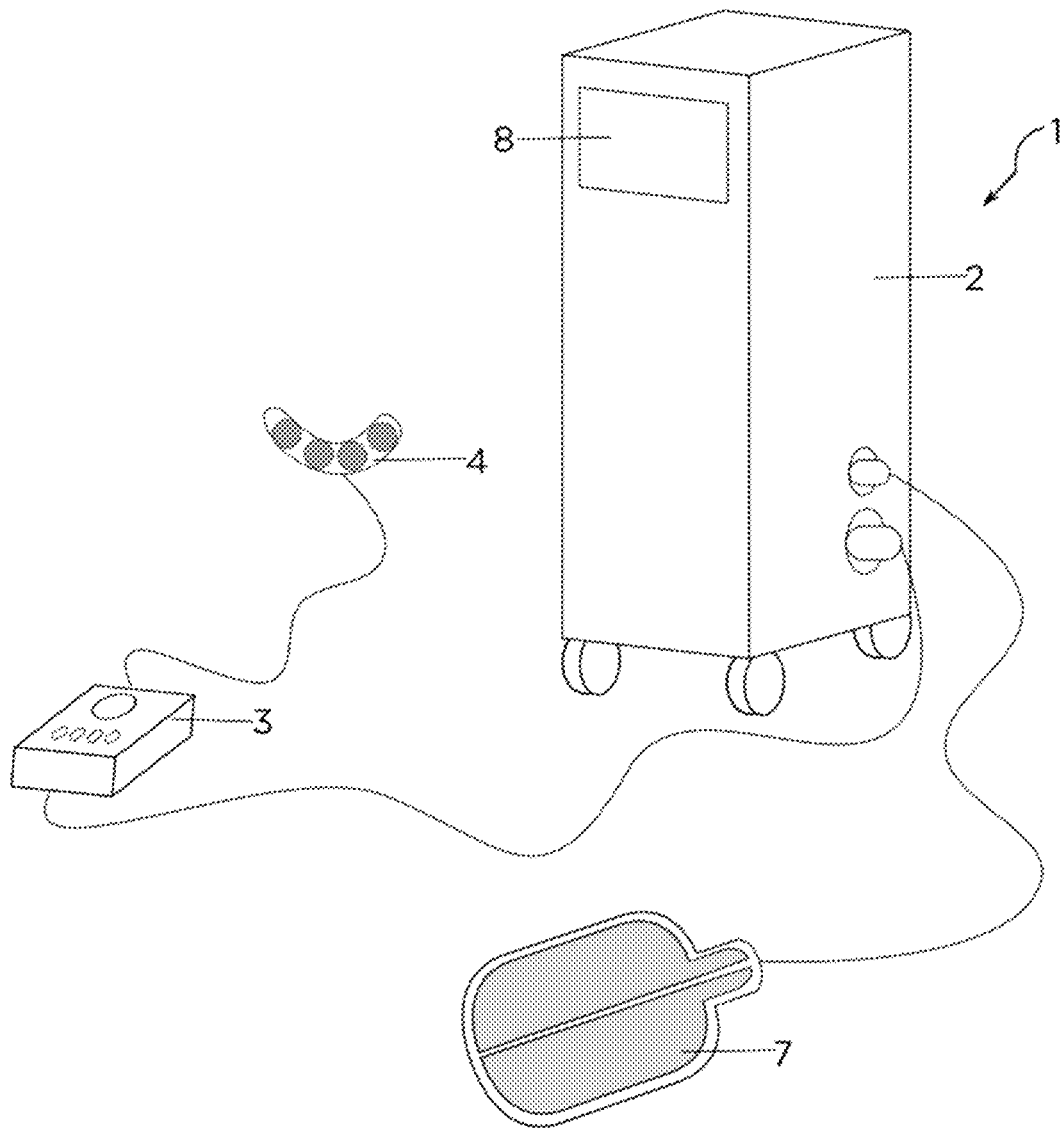
FIG. 2 is an illustration of an apparatus for contact therapy.

FIG. 1 and FIG. 2 are discussed together. FIG. 1 shows a block diagram of an apparatus 1 for contact therapy. FIG. 2 is an illustration of an apparatus 1 for contact therapy. The apparatus 1 for contact therapy may comprise two main blocks: main unit 2 and a pad 4. Additionally, the apparatus 1 may comprise interconnecting block 3 or neutral electrode 7. However, the components of interconnecting block 3, may be implemented into the main unit 2.

Main unit 2 may include one or more generators: a primary electromagnetic generator 6, which may preferably deliver radiofrequency energy in the range of 10 kHz to 300 GHz or 300 kHz to 10 GHz or 400 kHz to 6 GHz, or in the range of 100 kHz to 550 MHz or 250 kHz to 500 MHz or 350 kHz to 100 MHz or 400 kHz to 80 MHz, a secondary generator 9 which may additionally deliver electromagnetic energy, which does not heat the patient, or deliver electric current in the range of 1 Hz to 10 MHz or 5 Hz to 5 MHz or in the range of 10 Hz to 1 MHz or in the range of 20 Hz to 1 kHz or in the range of 40 Hz to 500 Hz or in the range of 50 Hz to 300 Hz and/or an ultrasound emitter 10 which may furthermore deliver an acoustic energy with a frequency in the range of 20 kHz to 25 GHz or 20 kHz to 1 GHz or 50 kHz to 250 MHz or 100 kHz to 100 MHz. In addition, the frequency of the ultrasound energy may be in the range of 20 kHz to 80 MHz or 50 kHz to 50 MHz or 150 kHz to 20 MHz.

The output power of the radiofrequency energy may be less than or equal to 450 W, 300 W, 250 W or 220 W. Additionally, the radiofrequency energy on the output of the primary electromagnetic generator 6 (e.g. radiofrequency generator) may be in the range of 0.1 W to 400 W, or in the range of 0.5 W to 300 W or in the range of 1 W to 200 W or in the range of 10 W to 150 W. The radiofrequency energy may be applied in or close to the ISM bands of 6.78 MHz, 13.56 MHz, 27.12 MHz, 40.68 MHz, 433.92 MHz, 915 MHz, 2.45 GHz and 5.8 GHz.

The primary generator 6 may also provide more than one radiofrequency energy with different parameters. As one non-limiting example, the primary generator may generate one radiofrequency energy with frequency in a range of 100 kHz to 550 MHz, 250 kHz to 500 MHz, 350 kHz to 100 MHz, or 400 kHz to 80 MHz and a second radiofrequency energy with a frequency in a range of 400 kHz to 300 GHz, 500 kHz to 30 GHz, 600 kHz to 10 GHz, or 650 kHz to 6 GHz.

Additionally, the heating of the patient may be provided by a heated fluid. In one aspect, the fluid may be heated in the heat generator inside the main unit 2 and may be coupled to the pad 4 by a fluid conduit, which may be in a form of a closed loop. When the heated fluid is delivered, e.g. via a pump, fan or other fluid delivery system, towards the patient via the active element in the pad 4, it dissipates its heat, and then the fluid is brought back to the heat generator where it is heated again. The fluid may be in form of a liquid (e.g. water, or oil) or a gas (e.g. air, nitrogen, carbon dioxide, carbon oxide, or other suitable gases know in the prior art). The fluid may be heated to the temperature in a range of 37.5° C. to 100° C., in a range of 38° C. to 64° C., or in a range of 40° C. to 57° C. In one aspect, the heated fluid may be supplementary heating energy for the electromagnetic heating energy or vice versa.

In one aspect, the heating may be provided by a heating element, for example a resistance wire or a thermoelectric cooler (TEC) which may be connected to primary electromagnetic generator 6 or secondary generator 9. In this aspect, the active element may be the heating element. The heating element may have the temperature on its surface in a range of 37.5° C. to 68° C., in a range of 38° C. to 62° C., or in a range of 39° C. to 50° C.

Main unit 2 may further comprise a human machine interface 8 represented by a display, buttons, a keyboard, a touchpad, a touch panel or other control members enabling an operator to check and adjust therapy and other device parameters. For example, it may be possible to set the power, treatment time or other treatment parameters of each generator (primary electromagnetic generator 6, secondary generator 9 and ultrasound emitter 10) independently. The human machine interface 8 may be connected to control unit 11 (e.g. CPU). The power supply 5 located in the main unit 2 may include a transformer, disposable battery, rechargeable battery, power plug or standard power cord. The output power of the power supply 5 may be in the range of 10 W to 600 W, or in the range of 50 W to 500 W, or in the range of 80 W to 450 W.

In addition the human machine interface 8 may also display information about the applied therapy type, remaining therapy time and main therapy parameters.

Interconnecting block 3 may serve as a communication channel between the main unit 2 and the pad 4. It may be represented by a simple device containing basic indicators 17 and mechanisms for therapy control. Indicators 17 may be realized through the display, LEDs, acoustic signals, vibrations or other forms capable of providing adequate notice to an operator and/or the patient. Indicators 17 may indicate actual patient temperature, contact information or other sensor measurements as well as a status of a switching process between the active elements, quality of contact with the treated tissue, actual treatment parameters, ongoing treatment, etc. Indicators 17 may be configured to warn the operator in case of suspicious therapy behavior, e.g. temperature out of range, improper contact with the treated tissue, parameters automatically adjusted etc. Interconnecting block 3 may be used as an additional safety feature for heat-sensitive patients. It may contain emergency stop button 16 so that the patient can stop the therapy immediately anytime during the treatment. Switching circuitry 14 may be responsible for switching between active elements or for regulation of energy delivery from primary electromagnetic generator 6, secondary generator 9 or ultrasound emitter 10. The rate of switching between active elements 13 may be dependent on the amount of delivered energy, pulse length etc, and/or on the speed of switching circuitry 14 and control unit 11 (e.g. CPU). The switching circuitry 14 may include relay switch, transistor (bipolar, PNP, NPN, FET, JFET, MOSFET) thyristor, diode, optical switch, opto-electrical switch or opto-mechanical switch or any other suitable switch know in the prior art. The switching circuitry in connection with the control unit 11 (e.g. CPU) may control the switching between the primary electromagnetic energy generated by the primary electromagnetic generator 6 and the secondary energy generated by the secondary generator 9 on the at least one active element 13.

Additionally, the interconnecting block 3 may contain the primary electromagnetic generator 6, the secondary generator 9 or ultrasound emitter 10 or only one of them or any combination thereof.

In one not limiting aspect, the main unit 2 may comprise the primary electromagnetic generator 6, the interconnecting block 3 may comprise the secondary generator 9, and ultrasound emitter 10 may not be present at all.

The control unit 11 (e.g. CPU) controls the primary electromagnetic generator 6 such that the primary electromagnetic energy may be delivered in a continuous mode (CM) or a pulse mode to the at least one active element, having a fluence in the range of 10 mJ/cm$^2$ to 50 kJ/cm$^2$ or in the range of 100 mJ/cm$^2$ to 10 kJ/cm$^2$ or in the range of 0.5 J/cm$^2$ to 1 kJ/cm$^2$. The electromagnetic energy may be primarily generated by a laser, laser diode module, LED, flash lamp or incandescent light bulb or by radiofrequency generator for causing the heating of the patient. The CM mode may be operated for a time interval in the range of 0.05 s to 60 min or in the range of 0.1 s to 45 min or in the range of 0.2 s to 30 min. The pulse duration of the energy delivery operated in the pulse regime may be in the range of 0.1 ms to 10 s or in the range of 0.2 ms to 7 s or in the range of 0.5 ms to 5 s. The primary electromagnetic generator 6 in the pulse regime may be operated by a control unit 11 (e.g. CPU) in a single shot mode or in a repetition mode. The frequency of the repetition mode may be in the range of 0.05 to 10 000 Hz or in the range of 0.1 to 5000 Hz or in the range of 0.3 to 2000 Hz or in the range of 0.5 to 1000 Hz. Alternatively, the frequency of the repetition mode may be in the range of 0.1 kHz to 200 MHz or in the range of 0.5 kHz to 150 MHz or in the range of 0.8 kHz to 100 MHz or in the range of 1 kHz to 80 MHz. The single shot mode may mean generation of just one electromagnetic pulse of specific parameters (e.g. intensity, duration, etc.) for delivery to a single treatment area. The repetition mode may mean generation of an electromagnetic pulses, which may have the specific parameters (e.g. intensity, duration, etc.), with a repetition rate of the above-mentioned frequency for delivery to a single treatment area. The control unit (e.g. CPU) 11 may provide treatment control such as stabilization of the treatment parameters including treatment time, power, duty cycle, time period regulating switching between multiple active elements, temperature of the device 1 and temperature of the primary electromagnetic generator 6 and secondary generator 9 or ultrasound emitter 10. The control unit 11 (e.g. CPU) may drive and provide information from the switching circuitry 14. The control unit 11 (e.g. CPU) may also receive and provide information from sensors located on or in the pad 4 or anywhere in the device 1. The control unit (e.g. CPU) 11 may include a flex circuit or a printed circuit board and may include a microprocessor or memory for controlling the device.

Figure 11A:
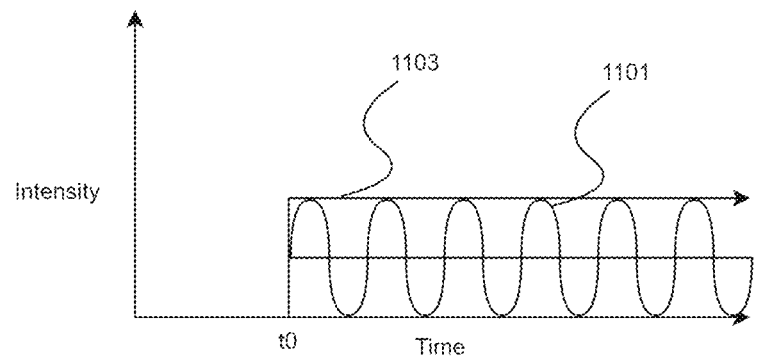
FIG. 11A illustrates a continual mode of electromagnetic energy
Figure 11B:
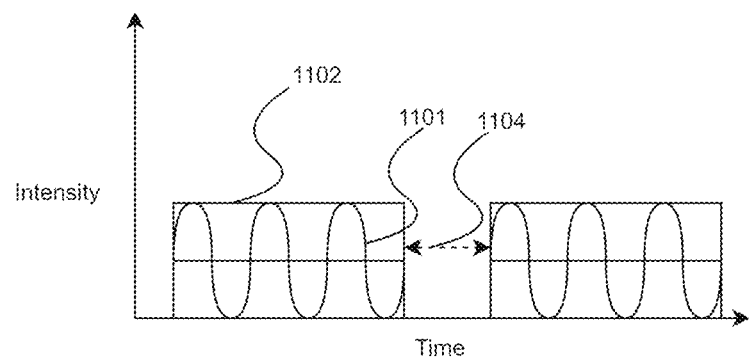
FIG. 11B illustrates a pulse mode of electromagnetic energy

FIG. 11A shows the delivery of the electromagnetic energy in the continuous mode. The electromagnetic waves 1101 (e.g. sinusoidal radiofrequency waves) are delivered continuously from the start time t0 with the continuous electromagnetic envelope 1103 (e.g. radiofrequency envelope). FIG. 11B shows the delivery of the electromagnetic energy in the pulse mode. The electromagnetic waves 1101 (e.g. sinusoidal radiofrequency waves) are delivered in electromagnetic pulses 1102 (e.g. radiofrequency pulses). The electromagnetic pulses 1102 may create at least one electromagnetic envelope 1105 (e.g. radiofrequency envelope), which is depicted as a rectangular electromagnetic envelope 1105 in FIG. 11B. The electromagnetic envelopes (1103, 1105) may have various shapes, e.g. circular, semicircular, sinusoidal, rectangular, triangular, trapezoidal, or polygonal shape.

The electromagnetic waves 1101 (e.g. radiofrequency waves) may be modulated in amplitude or frequency within one electromagnetic pulse (1102 or 1103) or may be modulated differently in different electromagnetic pulses. For example, a first electromagnetic pulse may have a rectangular envelope and a second electromagnetic pulse following the first electromagnetic pulse may have a sinusoidal envelope. The pause time 1104 between two consecutive pulses 1102 may be in the range of 1 µs to 1 s, in the range of 500 µs to 500 ms, in the range of 1 ms to 450 ms, or in the range of 100 ms to 450 ms. The pause time 1104 is a time when there are no electromagnetic waves provided by the device.

The control unit (e.g. CPU) 11 may control the secondary generator 9 such that secondary energy (e.g electric current or magnetic field) may be delivered in a continuous mode (CM) or a pulse mode to the at least one active element, having a fluence in the range of 10 mJ/cm$^2$ to 50 kJ/cm$^2$ or in the range of 100 mJ/cm$^2$ to 10 kJ/cm$^2$ or in the range of 0.5 J/cm$^2$ to 1 kJ/cm$^2$ on the surface of the at least one active element. Applying the secondary energy to the treatment area of the patient may cause a muscle contractions of the patient. The CM mode may be operated for a time interval in the range of 0.05 s to 60 min or in the range of 0.1 s to 45 min or in the range of 0.2 s to 30 min. The pulse duration of the delivery of the secondary energy operated in the pulse regime may be in the range of 0.1 µs to 10 s or in the range of 0.2 µs to 1 s or in the range of 0.5 µs to 500 ms, or in the range of 0.5 to 10 s or in the range of 1 to 8 s or in the range of 1.5 to 5 s or in the range of 2 to 3 s. The secondary generator 9 in the pulse regime may be operated by a control unit 11 (e.g. CPU) in a single shot mode or in a repetition mode. The frequency of the repetition mode may be in the range of 0.1 to 12 000 Hz or in the range of 0.1 to 8000 Hz or in the range of 0.1 to 5000 Hz or in the range of 0.5 to 1000 Hz.

Figure 11C:
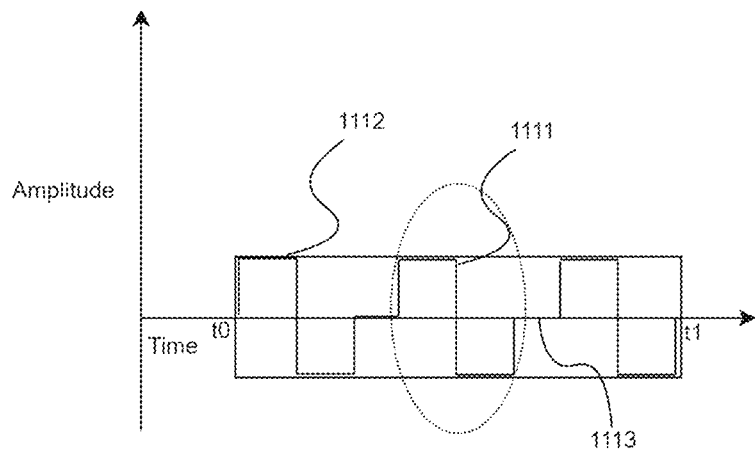
FIG. 11C illustrates a pulse mode of secondary energy

FIG. 11C shows the delivery of the secondary energy in the pulse mode. The secondary energy is delivered in secondary energy pulses 1111 (e.g. biphasic rectangular electric current pulses) which are provided continuously from the start time t0 to the end time t1, creating a secondary energy envelope 1112 (e.g. electric current envelope). One possible secondary energy pulse 1111 (e.g. electric pulse) is highlighted in the doted oval in FIG. 11C. The secondary energy pulses 1111 may be delivered uniformly one after another, or with a secondary energy pulse pause time 1113 between the secondary energy pulses 1111 as seen in FIG. 11C. The secondary energy pulse pause time 1113 means a time when there is no secondary energy delivered/generated between two consecutive secondary energy pulses 1111. A duty cycle of the secondary energy pulse 1111 and the secondary energy pulse pause time 1113 may be in the range of 0.1% to 99%, in the range of 0.5% to 50%, in the range of 0.7% to 33%, in the range of 1% to 17%, or in the range of 1.5% to 10%. In one aspect, the secondary energy pulse pause time 1113 may be in the range of 80 µs to 100 ms or in the range of 160 µs to 50 ms or in the range of 250 µs to 10 ms or in the range of 0.5 ms to 7 ms.

Figure 11D:
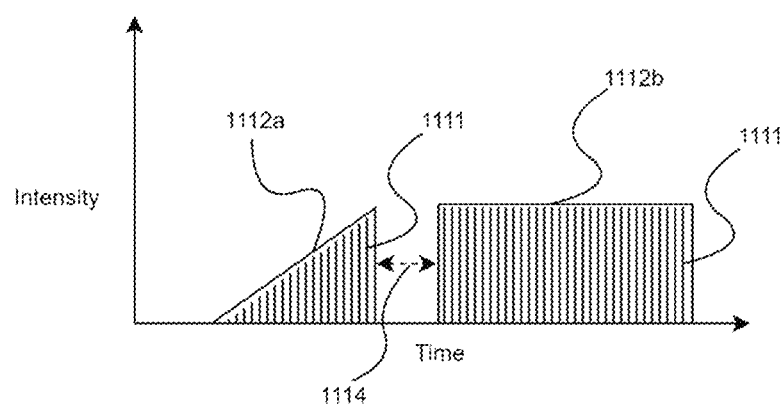
FIG. 11D illustrates possible modulations of energy establishing energy envelopes

The secondary energy (e.g. electric current pulses or magnetic field pulses) generated by the secondary generator 9 may be modulated in frequency or amplitude in the same way as the electromagnetic energy (e.g. radiofrequency waves) generated by the primary generator 6, creating different shapes of the secondary energy envelopes (e.g. electric current envelopes) as seen in FIG. 11D. For example, a first triangle envelope 1112a comprises series of secondary energy pulses 1111 that are modulated in amplitude such, that each consecutive secondary energy pulse has a higher amplitude than the previous one. A second rectangular envelope 1112b comprises series of secondary energy pulses 1111 having the same amplitude. As one can see from FIG. 11D the consecutive envelopes 1112a and 1112b may be separated by an envelope pause time, which is a time when there are no secondary energy pulses generated/delivered and no envelope established. In one aspect, the envelope pause time 1114 is longer than pulse pause time 1113. In another aspect, the envelope pause time 1114 has at least a length of the secondary energy pulse 1111 plus the secondary energy pulse pause time 1113. In one aspect, the secondary energy may be modulated within one secondary energy envelope 1112, and the envelopes may be the same for the whole treatment, e.g. only trapezoid envelope may be delivered through the treatment. In another aspect, the secondary energy may be modulated differently for different secondary energy envelopes 1112 delivered during the treatment, e.g. increasing envelope may be delivered first, than the rectangle envelope may be delivered secondly and then the decreasing triangle envelope may be delivered, wherein the envelopes are separated by the envelope pause time 1114. The secondary energy envelopes 1112 may have a shape of a sinus, triangle, conic, rectangle, trapezoid or polygon.

The secondary energy (e.g. electric current or magnetic field) may be also modulated in frequency within the secondary energy envelope 1112, which may cause an increasing or decreasing treatment response in the patient's body. For example, the electric current or the magnetic field may be modulated such that the frequency of secondary energy pulses 1111 is increasing, which may cause an intensity of muscle contractions to increase. Then the frequency of the secondary energy pulses 1111 may be constant causing the same intensity of muscle contractions and then the frequency of the secondary energy pulses 1111 may be decreasing causing decreasing intensity of the muscle contractions. The same principle may be used for the primary electromagnetic energy, thus creating, for example, series of increasing, constant and decreasing amplitudes of the electromagnetic energy, or series of increasing, constant and decreasing frequencies of the electromagnetic waves, which both may cause an increasing, constant and decreasing heating of the tissue of the patient.

Alternatively, it may be also possible to use only one generator to generate one type of energy/signal and one or more converters that convert the energy/signal to other one or more types of energy/signal. For example, the primary generator may generate a radiofrequency signal that is converted to electric current by the convertor (e.g. by a converting electric circuit).

The proposed device may be multichannel device allowing the control unit (e.g. CPU) 11 to control the treatment of more than one treated area at once.

Alternatively, the interconnecting block 3 may not be a part of the device 1, and the control unit (e.g. CPU) 11, switching circuitry 14, indicators 17 and emergency stop button 16 may be a part of the main unit 2 or pad 4. In addition, some of the control unit (e.g. CPU) 11, switching circuitry 14, indicators 17 and emergency stop button 16 may be a part of the main unit 2 and some of them part of pad 4, e.g. control unit (e.g. CPU) 11, switching circuitry 14 and emergency stop button 16 may be part of the main unit 2 and indicators 17 may be a part of the pad 4.

Pad 4 represents the part of the device which may be in contact with the patient's skin during the therapy. The pads 4 may be made of flexible substrate material—for example polymer-based material, polyimide (PI) films, polytetrafluoroethylene (PTFE, e.g., Teflon®), epoxy, polyethylene terephthalate (PET), polyamide or polyethylene (PE) foam with an additional adhesive layer on an underside, e.g. a hypoallergenic adhesive gel (hydrogel) or adhesive tape that may be bacteriostatic, non-irritating, or water-soluble. The substrate may also be a silicone-based substrate. The substrate may also be made of a fabric, e.g. non-woven fabric. The adhesive layer may have the impedance for a current at a frequency of 500 kHz in the range of 1 to 150Ω or in the range of 5 to 130Ω or in the range of 10 to 100Ω, and the impedance for a current at a frequency of 100 Hz or less is three times or more the impedance for a current at a frequency of 500 kHz. The adhesive hydrogel may be made of a polymer matrix or mixture containing water, a polyhydric alcohol, a polyvinylpyrrolidone, a polyisocyanate component, a polyol component or has a methylenediphenyl structure in the main chain. Additionally, a conductive adhesive may be augmented with metallic fillers, such as silver, gold, copper, aluminum, platinum or titanium or graphite that make up 1 to 90% or 2 to 80% or 5 to 70% of adhesive. The adhesive layer may be covered by "ST-gel®" or "Tensive®" conductive adhesive gel which is applied to the body to reduce its impedance, thereby facilitating the delivery of an electric shock.

The adhesive layer, e.g. hydrogel may cover exactly the whole surface of the pad facing the body area of the patient. The thickness of the hydrogel layer may be in the range of 0.1 to 3 mm or in the range of 0.3 to 2 mm or in the range of 0.4 to 1.8 mm or in the range of 0.5 to 1.5 mm.

The adhesive layer under the pad 4 may mean that the adhesive layer is between the surface of the pad facing the patient and the body of the patient. The adhesive layer may have impedance 1.1 times, 2 times, 4 times or up to 10 times higher than the impedance of the skin of the patient under the pad 4. A definition of the skin impedance may be that it is a portion of the total impedance, measured between two equipotential surfaces in contact with the epidermis, that is inversely proportional to the electrode area, when the internal current flux path is held constant. Data applicable to this definition would be conveniently recorded as admittance per unit area to facilitate application to other geometries. The impedance of the adhesive layer may be set by the same experimental setup as used for measuring the skin impedance. The impedance of the adhesive layer may be higher than the impedance of the skin by a factor in the range of 1.1 to 20 times or 1.2 to 15 times or 1.3 to 10 times.

The impedance of the adhesive layer may have different values for the different types of energy delivered to the patient, e.g. the impedance may be different for radiofrequency and for electric current delivery. The impedance of the hydrogel may be in the range of 100 to 2000 Ohms or in the range of 150 to 1800 Ohms or 200 to 1500 Ohms or 300 to 1200 Ohms in case of delivery of the electric current (e.g. during electrotherapy). In one aspect, the impedance of an adhesive layer (e.g. hydrogel) for AC current at 1 kHz may be in the range of 100 to 5000 Ohms, or of 200 to 4500 Ohms, or of 500 to 4000 Ohms, or of 1000 to 3000 Ohms, or of 1200 to 2800 Ohms, or of 1500 to 2500 Ohms. In another aspect, the impedance of the adhesive layer (e.g. hydrogel) for AC current at 10 Hz may be in the range of 2000 to 4000 Ohms, or of 2300 to 3700 Ohms, or of 2500 to 3500 Ohms.

The electric conductivity of the adhesive layer at radiofrequency of 3.2 MHz may be in the range of 20 to 200 mS/m or in the range of 50 to 140 mS/m or in the range of 60 to 120 mS/m or in the range of 70 to 100 mS/m.

Alternatively, the adhesive layer may be a composition of more elements, wherein some elements may have suitable physical properties (referred to herein as adhesive elements), e.g. proper adhesive and/or conductivity and/or impedance and/or cooling properties and so on; and some elements may have nourishing properties (referred to herein as nourishing elements), e.g. may contain nutrients, and/or vitamins, and/or minerals, and/or organic and/or inorganic substances with nourishing effect, which may be delivered to the skin of the patient during the treatment. The volumetric ratio of adhesive elements to nourishing elements may be in the range of 1:1 to 20:1, or of 2:1 to 10:1, or of 3:1 to 5:1, or of 5:1 to 50:1, or of 10:1 to 40:1, or of 15:1. In one aspect, the adhesive layer composition may contain a hydrogel as an adhesive element and a hyaluronic acid as a nourishing element. In another aspect, the adhesive layer composition may contain a hydrogel as an adhesive element and one or more vitamins as nourishing elements. In another aspect, the adhesive layer composition may contain a hydrogel as an adhesive element and one or more minerals as nourishing elements.

In one aspect, the nourishing element may be released continuously by itself during the treatment. In another aspect, the nourishing element may be released due to delivery of a treatment energy (e.g. heat, radiofrequency, light, electric current, magnetic field or ultrasound), which may pass through the nourishing element and thus cause its release to the skin of the patient.

The pad comprising the adhesive layer may be configured for a single use (disposable).

Alternatively, the pad may not contain the adhesive layer and may comprise at least the substrate and the active element (e.g. electrode).

In one aspect, at the beginning of the treatment the adhesive layer (e.g. hydrogel) may be externally applied on the surface of the patient prior to the application of the pad. The pad is then coupled to the adhesive layer. In another aspect, a covering layer (e.g. thin foil) may be inserted between the adhesive layer and the pad. The foil may be adhesive on one side or on both sides and provide a coupling of the pad with the body of the patient. In this case, it may be possible to use the same pad more than once as the covering layer guarantee the hygienic safety of the pad.

In another aspect, layers of some other substance may be applied on the surface of the patient prior to the application of the pad and the pad is coupled to this layer. This may be active substance layer, cooling layer (e.g. cooling gel), partially adhesive layer, or any other non-adhesive layer. In one aspect, the active substance layer may comprise e.g. hyaluronic acid, one or more vitamins, one or more minerals or any of their combination. The active substance from the active substance layer may be in form of a solution (e.g. gel or cream) applied on the patient or may be coupled to the covering layer (e.g. thin foil), which is then attached to the skin of the patient. The active substance may be continuously released into the skin due to at least one energy provided by the pad (e.g. radiofrequency energy, or heat, or electric current or magnetic field, etc.) throughout the treatment. In another aspect, the active substance may be released into the skin at the beginning, at some time during, or at the end of the treatment in order to visually improve the skin.

The pad 4 may also have a sticker on a top side of the pad. The top side is the opposite side from the underside (the side where the adhesive layer may be deposited) or in other words the top side is the side of the pad that is facing away from the patient during the treatment. The sticker may have a bottom side and a top side, wherein the bottom side of the sticker may comprise a sticking layer and the top side of the sticker may comprise non-sticking layer (eg. polyimide (PI) films, PTFE (e.g. Teflon®), epoxy, polyethylene terephthalate (PET), polyamide or PE foam, PE film or PVC foam). Thus the sticker may be made of two layers (top non-sticking and bottom sticking layer). The sticker covers the top side of the pad and may also cover some sensors situated on the top side of the pad (e.g. thermal sensors).

The sticker may have the same shape as the pad 4 or may have additional overlap over the pad, e.g., extend beyond the shape of the pad 4. The sticker may be bonded to the pad such that the sticking layer of the bottom side of the sticker is facing toward the top side of the pad 4. The top side of the sticker facing away from the pad 4 may be made of a non-adhesive layer. The linear dimension of the sticker with additional overlap may exceed the corresponding dimension of the pad in the range of 0.1 to 10 cm, or in the range of 0.1 to 7 cm, or in the range of 0.2 to 5 cm, or in the range of 0.2 to 3 cm, or in the range of 0.3 to 1 cm. The area of the sticker (with the overlap) may be 0.5% to 50%, 1% to 40%, 1.5% to 33%, 2% to 25% 3% to 20%, or 5% to 15% larger than the area of the pad. This overlap may also comprise an adhesive layer and may be used to form additional and more proper contact of the pad with the patient. The thickness of the sticker may be in the range of 0.05 to 3 mm or in the range of 0.1 to 2 mm or in the range of 0.5 to 1.5 mm. The top side of the sticker may have a printed inscription for easy recognition of the pad, e.g. the brand of the manufacturer or the proposed treated body area.

In one aspect, the adhesive layer, e.g. hydrogel, on the underside of the pad facing the body area of the patient may cover the whole surface of the pad and even overlap the surface of the pad and cover at least partially the overlap of the sticking layer. In another aspect, the underside of the adhesive layer and/or the overlap of the sticker (both parts facing towards the patient) may be covered by a liner, which may be removed just before the treatment. The liner protects the adhesive layer and/or the overlap of the sticker, thus when the liner is removed the proper adhesion to the body area of the patient is ensured.

Alternatively, the pad 4 may comprise at least one suction opening, e.g. small cavities or slits adjacent to active elements or the active element may be embedded inside a cavity. The suction opening may be connected via connecting tube to a pump which may be part of the main unit 2. When the suction opening is brought into contact with the skin, the air sucked from the suction opening flows toward the connecting tube and the pump and the skin may be slightly sucked into the suction opening. Thus by applying a vacuum the adhesion of pad 4 may be provided. Furthermore, the pad 4 may comprise the adhesive layer and the suction openings for combined stronger adhesion.

In addition to the vacuum (negative pressure), the pump may also provide a positive pressure by pumping the fluid to the suction opening. The positive pressure is pressure higher than atmospheric pressure and the negative pressure or vacuum is lower than atmospheric pressure. Atmospheric pressure is a pressure of the air in the room during the therapy.

The pressure (positive or negative) may be applied to the treatment area in pulses providing a massage treatment. The massage treatment may be provided by one or more suction openings changing pressure value to the patient's soft tissue in the meaning that the suction opening apply different pressure to patient tissue. Furthermore, the suction openings may create a pressure gradient in the soft tissue without touching the skin. Such pressure gradients may be targeted on the soft tissue layer, under the skin surface and/or to different soft tissue structure.

Massage accelerates and improves treatment therapy by electromagnetic energy, electric energy or electromagnetic energy which does not heat the patient, improves blood and/or lymph circulation, angioedema, erythema effect, accelerates removing of the fat, accelerate metabolism, accelerates elastogenesis and/or neocolagenesis.

Each suction opening may provide pressure by a suction mechanism, airflow or gas flow, liquid flow, pressure provided by an object included in the suction opening (e.g. massaging object, pressure cells etc.) and/or in other ways.

Pressure value applied on the patient's tissue means that a suction opening providing massaging effect applies positive, negative and/or sequentially changing positive and negative pressure on the treated and/or adjoining patient's tissue structures and/or creates a pressure gradient under the patient's tissue surface Massage applied in order to improve body liquid flow (e.g. lymph drainage) and/or relax tissue in the surface soft tissue layers may be applied with pressure lower than during the massage of deeper soft tissue layers. Such positive or negative pressure compared to the atmospheric pressure may be in a range of 10 Pa to 30 000 Pa, or in a range of 100 Pa to 20 000 Pa or in a range of 0.5 kPa to 19 kPa or in a range of 1 kPa to 15 kPa.

Massage applied in order to improve body liquid flow and/or relaxation of the tissue in the deeper soft tissue layers may be applied with higher pressure. Such positive or negative pressure may be in a range from 12 kPa to 400 kPa or from 15 kPa to 300 kPa or from 20 kPa to 200 kPa. An uncomfortable feeling of too high applied pressure may be used to set a pressure threshold according to individual patient feedback.

Negative pressure may stimulate body liquid flow and/or relaxation of the deep soft tissue layers (0.5 cm to non-limited depth in the soft tissue) and/or layers of the soft tissue near the patient surface (0.1 mm to 0.5 cm). In order to increase effectiveness of the massage negative pressure treatment may be used followed by positive pressure treatment.

A number of suction openings changing pressure values on the patient's soft tissue in one pad 4 may be between 1 to 100 or between 1 to 80 or between 1 to 40 or between 1 to 10.

Sizes and/or shapes of suction openings may be different according to treated area. One suction opening may cover an area on the patient surface between 0.1 $mm^2$ to 1 $cm^2$ or between 0.1 $mm^2$ to 50 $mm^2$ or between 0.1 $mm^2$ to 40 $mm^2$ or between 0.1 $mm^2$ to 20 $mm^2$. Another suction opening may cover an area on the patient surface between 1 $cm^2$ to 1 $m^2$ or between 1 $cm^2$ to 100 $cm^2$ or between 1 $cm^2$ to 50 $cm^2$ or between 1 $cm^2$ to 40 $cm^2$.

Several suction openings may work simultaneously or switching between them may be in intervals between 1 ms to 10 s or in intervals between 10 ms to 5 s or in intervals between 0.5 s to 2 s.

Suction openings in order to provide massaging effect may be guided according to one or more predetermined massage profile included in the one or more treatment protocols. The massage profile may be selected by the operator and/or by a control unit (e.g. CPU) with regard to the patient's condition. For example a patient with lymphedema may require a different level of compression profile and applied pressure than a patient with a healed leg ulcer.

Pressure applied by one or more suction openings may be gradually applied preferably in the positive direction of the lymph flow and/or the blood flow in the veins. According to specific treatment protocols the pressure may be gradually applied in a direction opposite or different from ordinary lymph flow. Values of applied pressure during the treatment may be varied according to the treatment protocol.

A pressure gradient may arise between individual suction openings. Examples of gradients described are not limited for this method and/or device. The setting of the pressure gradient between at least two previous and successive suction openings may be: 0%, i.e. The applied pressure by suction openings is the same (e.g. pressure in all suction openings of the pad is the same);

1%, i.e. The applied pressure between a previous and a successive suction opening decreases and/or increases with a gradient of 1% (e.g. the pressure in the first suction opening is 5 kPa and the pressure in the successive suction opening is 4.95 kPa);

2%, i.e. The pressure decreases or increases with a gradient of 2%. The pressure gradient between two suction openings may be in a range 0% to 100% where 100% means that one suction openings is not active and/or does not apply any pressure on the patient's soft tissue.

A treatment protocol that controls the application of the pressure gradient between a previous and a successive suction opening may be in a range between 0.1% to 95%, or in a range between 0.1% to 70%, or in a range between 1% to 50%.

The suction opening may also comprise an impacting massage object powered by a piston, massage object operated by filling or sucking out liquid or air from the gap volume by an inlet/outlet valve or massage object powered by an element that creates an electric field, magnetic field or electromagnetic field. Additionally, the massage may be provided by impacting of multiple massage objects. The multiple massage objects may have the same or different size, shape, weight or may be created from the same or different materials. The massage objects may be accelerated by air or liquid flowing (through the valve) or by an electric, magnetic or electromagnetic field. Trajectory of the massage objects may be random, circular, linear and/or massage objects may rotate around one or more axes, and/or may do other types of moves in the gap volume.

The massage unit may also comprise a membrane on the side facing the patient which may be accelerated by an electric, magnetic, electromagnetic field or by changing pressure value in the gap volume between wall of the chamber and the membrane. This membrane may act as the massage object.

During the treatment, it may be convenient to use a combination of pads with adhesive layer and pads with suction openings. In that case at least one pad used during the treatment may comprise adhesive layer and at least additional one pad used during the treatment may comprise suction opening. For example, pad with adhesive layer may be suited for treatment of more uneven areas, e.g. periorbital area, and pad with suction openings for treatment of smoother areas, e.g. cheeks.

The advantage of the device where the attachment of the pads may be provided by an adhesion layer or by a suction opening or their combination is that there is no need of any additional gripping system which would be necessary to hold the pads on the treatment area during the treatment, e.g. a band or a felt, which may cause a discomfort of the patient.

In one aspect, the suction openings may provide the heated fluid to cause heating of the patient (e.g. hot air), which may be provided instead of, or as u supplementary energy to the primary electromagnetic energy (e.g. radiofrequency energy).

Yet in another aspect, it is possible to fasten the flexible pads 4 to the face by at least one fastening mechanism, for example—a band or a felt, which may be made from an elastic material and thus adjustable for an individual face. In that case the flexible pads, which may have not the adhesive layer or suction opening, are placed on the treatment area of the patient and their position is then fastened by a band or felt to avoid deflection of the pads from the treatment areas. Alternatively, the band may be replaced by a mask, e.g. an elastic mask that covers from 5% to 100% or from 30% to 99% or from 40% to 95% or from 50% to 90% of the face and may serve to secure the flexible pads on the treatment areas. In another aspect, the mask may be rigid or semi rigid. The mask may contain one connecting part comprising conductive leads which then distributes the conductive leads to specific pads. Furthermore, it may be possible to use the combination of the pad with adhesive layer or suction opening and the fastening band, felt or mask to ensure strong attachment of the pads on the treatment areas.

Additionally, the fastening mechanism may be in the form of a textile or a garment which may be mountable on a patient's body part. In use of the device, a surface of the active element or pad 4 lays along an inner surface of the garment, while the opposite surface of the active element or pad 4 is in contact with the patient's skin, preferably by means of a skin-active element hydrogel interface.

The garment may be fastened for securement of the garment to or around a patient's body part, e.g. by hook and loop fastener, button, buckle, stud, leash or cord, magnetic-guided locking system or clamping band and the garment may be manufactured with flexible materials or fabrics that adapt to the shape of the patient's body or limb. The pad 4 may be in the same way configured to be fastened to the inner surface of the garment. The garment is preferably made of breathable materials. Non limiting examples of such materials are soft Neoprene, Nylon, polyurethane, polyester, polyamide, polypropylene, silicone, cotton or any other material which is soft and flexible. All named materials could be used as woven, non-woven, single use fabric or laminated structures.

The garment and the pad may be modular system, which means module or element of the device (pad, garment) and/or system is designed separately and independently from the rest of the modules or elements, at the same time that they are compatible with each other.

The pad 4 may be designed to be attached to or in contact with the garment, thus being carried by the garment in a stationary or fixed condition, in such a way that the pads are disposed on fixed positions of the garment. The garment ensures the correct adhesion or disposition of the pad to the patient's skin. In use of the device, the surface of one or more active elements not in contact with the garment is in contact with the patient's skin, preferably by means of a hydrogel layer that acts as pad-skin interface. Therefore, the active elements included in the pad are in contact with the patient's skin.

The optimal placement of the pad on the patient's body part, and therefore the garment which carries the pad having the active elements, is determined by a technician or clinician helping the patient.

In addition, the garment may comprise more than one pad or the patient may wear more than one garment comprising one or more pads during one treatment session.

The pad 4 contains at least one active element 13 capable of delivering energy from primary electromagnetic generator 6 or secondary generator 9 or ultrasound emitter 10. In various aspects, the active element is an electrode, an optical element, an acoustic window, an ultrasound emitter, a coil, a fluid conduit, a heating element, or other energy delivering elements known in the art. The electrode may be a radiofrequency (RF) electrode. The RF electrode may be a dielectric electrode coated with insulating (e.g. dielectric) material. The RF electrode may be monopolar, bipolar, unipolar or multipolar. The bipolar arrangement may consist of electrodes that alternate between active and return function and where the thermal gradient beneath electrodes is almost the same during treatment. Bipolar electrodes may form circular or ellipsoidal shapes, where electrodes are concentric to each other. However, a group of bipolar electrode systems may be used as well. A unipolar electrode or one or more multipolar electrodes may be used as well. The system may alternatively use monopolar electrodes, where the so-called return electrode (or neutral electrode or ground electrode or grounding electrode) has larger area than so-called active electrode. The thermal gradient beneath the active electrode is therefore higher than beneath the return electrode. The active electrode may be part of the pad and the passive electrode having larger surface area may be located at least 5 cm, 10 cm, or 20 cm from the pad. A neutral electrode may be used as the passive electrode. The neutral electrode may be on the opposite side of the patient's body than the pad is attached. A unipolar electrode may also optionally be used. During unipolar energy delivery there is one electrode, no neutral electrode, and a large field of RF emitted in an omnidirectional field around a single electrode. Capacitive and/or resistive electrodes may be used. Radiofrequency energy may provide energy flux on the surface of the RF electrode or on the surface of the treated tissue (e.g. skin) in the range of 0.001 W/cm$^2$ to 1500 W/cm$^2$ or 0.01 W/cm$^2$ to 1000 W/cm$^2$ or 0.5 W/cm$^2$ to 500 W/cm$^2$ or 0.5 W/cm$^2$ to 100 W/cm$^2$ or 1 W/cm$^2$ to 50 W/cm$^2$. The energy flux on the surface of the RF electrode may be calculated from the size of the RF electrode and its output value of the energy. The energy flux on the surface of the treated tissue may be calculated from the size of the treated tissue exactly below the RF electrode and its input value of the energy provided by the RF electrode. In addition, the RF electrode positioned in the pad 4 may act as an acoustic window for ultrasound energy.

The active element 13 may provide a secondary energy from secondary generator 9 in the form of an electric current or a magnetic field. By applying the secondary energy to the treated area of the body of the patient, muscle fibers stimulation (e.g. muscle contractions) may be achieved and thus increasing muscle tone, muscle strengthening, restoration of feeling the muscle, relaxation of the musculature and/or stretching musculature.

The magnetic field provided by the active element 13 (e.g. coil) used for simulation of the muscle may be in the range of 0.01 T to 7 T, or in the range of 0.015 T to 4 T or in the range of 0.02 T to 1 T or in the range of 0.05 T to 0.5 T, on the surface of the active element (e.g. coil). The maximum value of the magnetic flux density derivative may be in the range of 1 T/s to 800 kT/s or in the range of 40 T/s to 320 kT/s or in the range of 80 T/s to 250 kT/s or in the range of 100 T/s to 250 kT/s or in the range of 250 T/s to 180 kT/s or in the range of 500 T/s to 100 kT/s or in the range of 1 kT/s to 65 kT/s. The value of magnetic flux density derivative may correspond to induced current within the tissue. The pulse duration of the magnetic field may be in the range of 3 µs to 10 ms, or alternatively 3 µs to 3 ms or alternatively 3 µs to 1 ms. The active element 13 (e.g. coil) may provide pulses of magnetic field with the frequency in the range of 1 Hz to 1200 kHz or in the range of 2 Hz to 600 Hz or in the range of 3 Hz to 250 Hz or in the range of 4 Hz to 150 Hz or in the range of 4 Hz to 65 Hz.

An inductance of the active element 13 (e.g. coil) used for magnetic field generation may be in the range of 1 nH to 500 mH, or in the range of 10 nH to 50 mH, or in the range of 50 nH to 10 mH, or in the range of 500 nH to 1 mH, or in the range of 1 µH to 500 µH. Alternatively, the inductance of the active element (e.g. coil) used for magnetic field generation may be in the range of 1 nH to 100 µH, or in the range of 5 nH to 50 µH, or in the range of 10 nH to 25 µH or in the range of 45 nH to 20 µH.

The proposed device may provide an electrotherapy in case that the secondary energy delivered by the active element 13 (e.g an electrotherapy electrode or simply referred just as an electrode, which may also be the radiofrequency electrode as described above) is the electric current generated by the secondary generator 9. The main effects of electrotherapy are: analgesic, myorelaxation, iontophoresis, anti-edematous effect or muscle stimulation causing a muscle fiber contraction. Each of these effects may be achieved by one or more types of electrotherapy: galvanic current, pulse direct current and alternating current.

Galvanic current (or "continuous") is a current that may have constant electric current and/or absolute value of the electric current is in every moment higher than 0. It may be used mostly for iontophoresis, or its trophic stimulation (hyperemic) effect is utilized. At the present invention this current may be often substituted by galvanic intermittent current. Additionally, galvanic component may be about 95% but due to interruption of the originally continuous intensity the frequency may reach 5-12 kHz or 5-10 kHz or 5-9 kHz or 5-8 kHz.

The pulse direct current (DC) is of variable intensity but only one polarity. The basic pulse shape may vary. It includes e.g. diadynamics, rectangular, triangular and exponential pulse of one polarity. Depending on the used frequency and intensity it may have stimulatory, tropic, analgesic, myorelaxation, iontophoresis, at least partial muscle contraction and anti-edematous effect and/or other.

Alternating Current (AC or biphasic) where the basic pulse shape may vary—rectangular, triangular, harmonic sinusoidal, exponential and/or other shapes and/or combination of mentioned above. It can be alternating, symmetric and/or asymmetric. Use of alternating currents in contact electrotherapy implies much lower stress on the tissue under the electrode. For these types of currents the capacitive component of skin resistance is involved, and due to that these currents are very well tolerated by the patients.

AC therapies may be differentiated into five subtypes: TENS, Classic (four-pole) Interference, Two-pole Interference, Isoplanar Interference and Dipole Vector Field. There also exists some specific electrotherapy energy variants and modularity of period, shape of the energy etc.

Due to interferential electrotherapy, different nerves and tissue structures by medium frequency may be stimulated in a range of 500 Hz to 12 kHz or in a range of 500 Hz to 8 kHz, or 500 Hz to 6 kHz, creating pulse envelopes with frequencies for stimulation of the nerves and tissues e.g. sympathetic nerves (0.1-5 Hz), parasympathetic nerves (10-150 Hz), motor nerves (10-50 Hz), smooth muscle (0.1-10 Hz), sensor nerves (90-100 Hz) nociceptive fibers (90-150 Hz).

Electrotherapy may provide stimulus with currents of frequency in the range from 0.1 Hz to 12 kHz or in the range from 0.1 Hz to 8 kHz or in the range from 0.1 Hz to 6 kHz.

Muscle fiber stimulation by electrotherapy may be important during and/or as a part of the RF treatment. Muscle stimulation increases blood flow and lymph circulation. It may improve removing of treated cells and/or prevent of hot spots creation. Moreover internal massage stimulation of adjoining tissues improves homogeneity of tissue and dispersing of the delivered energy. The muscle fiber stimulation by electrotherapy may cause muscle contractions, which may lead to improvement of a visual appearance of the patient through muscle firming and strenghtening, Another beneficial effect is for example during fat removing with the RF therapy. RF therapy may change structure of the fat tissue. The muscle fiber stimulation may provide internal massage, which may be for obese patient more effective than classical massage.

Muscle stimulation may be provided by e.g. intermittent direct currents, alternating currents (e.g. medium-frequency currents, Russian currents and TENS currents), faradic current as a method for multiple stimulation and/or others.

Frequency of the currents may be in the range from 0.1 Hz to 1500 Hz or from 0.1 to 1000 Hz or from 0.1 to 500 Hz or from 0.1 to 300 Hz.

Frequency of the current envelope is typically in the range from 0.1 Hz to 500 Hz or from 0.1 to 250 Hz or from 0.1 Hz to 150 Hz or from 0.1 to 140 Hz. Additionally, the current envelopes may have an envelope repetition frequency (ERF) in a range of 0.01 to 100 per second, or of 0.05 to 50 per second, or of 0.07 to 30 per second, or of 0.1 to 20 per second, or of 0.2 to 6 per second.

The electrostimulation may be provided in a combined manner where various treatments with various effects may be achieved. As an illustrative example, the electromagnetic energy with the electrostimulation may be dosed in trains of pulses of electric current where the first train of electrostimulation may achieve different effect than second or other successive train of stimulation. Therefore, the treatment may provide muscle fibers stimulation or muscle contractions followed by relaxation, during continual or pulsed radiofrequency thermal heating provided by electromagnetic energy provided by electromagnetic energy generator.

The electrostimulation may be provided by monopolar, unipolar, bipolar or multipolar mode.

Absolute value of voltage between the electrotherapy electrodes operated in bipolar, multipolar mode (electric current flow between more than two electrodes) and/or provided to at least one electrotherapy electrode may be in a range between 0.8 V and 10 kV; or in a range between 1 V and 1 kV; or in a range between 1 V and 300 V or in a range between 1 V and 100 V or in a range between 10 V and 80 V or in a range between 20 V and 60 V or in a range between 30 V and 50 V.

Current density of electrotherapy for a non-galvanic current may be in a range between 0.1 mA/cm$^2$ and 150 mA/cm$^2$, or in a range between 0.1 mA/cm$^2$ and 100 mA/cm$^2$, or in a range between 0.1 mA/cm$^2$ and 50 mA/cm$^2$, or in a range between 0.1 mA/cm$^2$ and 20 mA/cm$^2$; for a galvanic current may be preferably in a range between 0.05 mA/cm$^2$ and 3 mA/cm$^2$, or in a range between 0.1 mA/cm$^2$ and 1 mA/cm$^2$, or in a range between 0.01 mA/cm$^2$ and 0.5 mA/cm$^2$. The current density may be calculated on the surface of the electrode providing the electrotherapy to the patient. In one aspect, the current density of electrotherapy for a non-galvanic current may be in a range between 0.1 mA/cm$^2$ and 200 mA/cm$^2$, or in a range between 0.5 mA/cm$^2$ and 150 mA/cm$^2$, or in a range between 1 mA/cm$^2$ and 120 mA/cm$^2$, or in a range between 5 mA/cm$^2$ and 100 mA/cm$^2$.

The electric current in one pulse in case of a pulsed electric current (e.g. pulse mode) may be in the range of 0.5 mA to 150 mA, in the range of 1 mA to 100 mA, in the range of 5 mA to 75 mA, or in the range of 10 mA to 55 mA. The duration of one electric current pulse may be preferably in the range of 1 to 500 µs, in the range of 10 to 350 µs, in the range of 20 to 200 µs, in the range of 35 to 150 µs, or in the range of 50 to 100 µs.

During electrotherapy, e.g. bipolar electrotherapy, two or more electrodes may be used. If polarity of at least one electrode has a non-zero value in a group of the electrodes during bipolar mode, the group of the electrodes has to include at least one electrode with opposite polarity value. Absolute values of both electrode polarities may or may not be equal. In bipolar electrostimulation mode stimulating signal passes through the tissue between electrodes with opposite polarities.

A distance between two electrodes operating in bipolar mode may be in a range between 0.1 mm and 4 cm or in a range between 0.2 mm to 3 cm or in a range between 0.5 mm and 2 cm or in a range between 1 mm and 1 cm or in a range between 2 mm and 7 mm, or in the range of 0.1 cm and 40 cm or in a range between 1 cm and 30 cm, or in the range between 1 cm and 20 cm, wherein the distance is between the two closest points of two electrodes operating in bipolar mode.

During monopolar electrotherapy mode stimulating signal may be induced by excitement of action potential by changing polarity of one electrode that change polarization in the nerve fiber and/or neuromuscular plague.

During the electrotherapy, one of the bipolar or monopolar electrotherapy mode may be used or bipolar or monopolar electrotherapy mode may be combined.

The ultrasound emitters may provide focused or defocused ultrasound energy. The ultrasound energy may be transferred to the tissue through an acoustic window. The output power of the ultrasound energy on the surface of the active element 13 may be less than or equal to 20 W or 15 W or 10 W or 5 W. Ultrasound energy may provide energy flux on the surface of the active element 13 or on the surface of the treated tissue (e.g. skin) in the range of 0.001 $W/cm^2$ to 250 $W/cm^2$, or in the range of 0.005 $W/cm^2$ to 50 $W/cm^2$, or in the range of 0.01 $W/cm^2$ to 25 $W/cm^2$, or in the range of 0.05 $W/cm^2$ to 20 $W/cm^2$. The treatment depth of ultrasound energy may be in the range of 0.1 mm to 100 mm or 0.2 mm to 50 mm or 0.25 mm to 25 mm or 0.3 mm to 15 mm. At a depth of 5 mm the ultrasound energy may provide an energy flux in the range of 0.01 $W/cm^2$ to 20 $W/cm^2$ or 0.05 $W/cm^2$ to 15 $W/cm^2$. An ultrasound beam may have a beam non-uniformity ratio (RBN) in the range of 0.1 to 20 or 2 to 15 to 4 to 10. In addition, an ultrasound beam may have a beam non-uniformity ratio below 15 or below 10. An ultrasound beam may be divergent, convergent and/or collimated. The ultrasound energy may be transferred to the tissue through an acoustic window. It is possible that the electrode may act as the acoustic window. Furthermore, the ultrasound emitter 10 may be a part of the active element 13, thus ultrasound emitter 10 may be a part of the pad 4.

In one aspect, the ultrasound may provide heating of the patient, and the ultrasound emitter 10 may be used instead of the primary electromagnetic generator 6, which may not be presented in the device. In another aspect, the ultrasound may provide supplementary heating energy to the energy generated by the primary electromagnetic generator 6.

At least some of the active elements 13 may be capable of delivering energy from primary electromagnetic generator 6 or secondary generator 9 or ultrasound emitter 10 simultaneously (at the same time) successively or in an overlapping method or in any combination thereof. For example, the active element 13 (e.g. electrode) may be capable of delivering radiofrequency energy and electric current sequentially, which may mean that firstly the active element 13 may provide primary electromagnetic energy generated by the primary electromagnetic generator 6 and subsequently the active element 13 may provide the secondary energy generated by the secondary generator 9. Thus the active element 13 may e.g. apply radiofrequency energy to the tissue of the patient and then the same active element 13 may apply e.g. electrical current to the tissue of the patient. In one aspect, the primary electromagnetic generator may generate both, the radiofrequency energy and the electric current.

In one aspect, the proposed device 1 may provide only one treatment energy, e.g. only electric current to cause a muscle stimulation or only radiofrequency energy to cause heating of the tissue.

The active element (e.g. electrode or coil) may be cooled. A cooling member may provide cooling by any known mechanism including e.g. water cooling, sprayed coolant, presence of an active solid cooling element (e.g. thermoelectric cooler), or air flow cooling. Cooling of the active element (e.g. electrode or coil) may be provided during, before, or after the active element provides an energy to the patient. The temperature of the cooling member may be in the range of −80° C. to 36° C., in the range of −70° C. to 35° C., in the range of −60° C. to 34° C., in the range of −20° C. to 30° C., in the range of 0° C. to 27° C., in the range of 5° C. to 25° C.

Pad 4 may further comprise thermal sensors 15 enabling temperature control during the therapy, providing feedback to control unit (e.g. CPU) 11, enabling adjustment of treatment parameters of each active element and providing information to the operator. The thermal sensor 15 may be a contact sensor, contactless sensor (e.g. infrared temperature sensor) or invasive sensor (e.g. a thermocouple) for precise temperature measurement of deep layers of skin, e.g. epidermis, dermis or hypodermis. The control unit (e.g. CPU) 11 may also use algorithms to calculate the deep or upper-most temperatures. A temperature feedback system may control the temperature and based on set or pre-set limits alert the operator in human perceptible form, e.g. on the human machine interface 8 or via indicators 17. In a limit temperature condition, the device may be configured to adjust one or more treatment parameters, e.g. output power, switching mode, pulse length, etc. or stop the treatment. A human perceptible alert may be a sound, alert message shown on human machine interface 8 or indicators 17 or change of color of any part of the interconnecting block 3 or pad 4.

The pad may comprise at least one electromyography (EMG) sensing electrode configured to monitor, to record or to evaluate the electrical activity produced by skeletal muscles (e.g. twitch or contraction) in response to delivered energy (e.g. electric current). The at least one EMG sensing electrode being disposed on the pad may be electrically insulated from the active elements (e.g. electrodes used for treatment). An electromyograph detects the electric potential generated by muscle cells when these cells are electrically or neurologically activated. The signals can be analyzed to detect abnormalities, activation level, or recruitment order, or to analyze the biomechanics of the patient's movement. The EMG may be one of a surface EMG or an intramuscular EMG. The surface EMG can be recorded by a pair of electrodes or by a more complex array of multiple electrodes. EMG recordings display the potential difference (voltage difference) between two separate electrodes. Alternatively the active elements, e.g. electrodes, may be used for EMG, for example when the active element is not active (e.g. does not provide/deliver any type of energy/signal to the patient) it may be used for EMG detection/recording. The intramuscular EMG may be recorded by one (monopolar) or more needle electrodes. This may be a fine wire inserted into a muscle with a surface electrode as a reference; or more fine wires inserted into muscle referenced to each other. Muscle tissue at rest is normally electrically inactive. After the electrical activity caused by delivered energy (e.g. electric current), action potentials begin to appear. As the strength of a muscle contraction is increased, more and more muscle fibers produce action potentials. When the muscle is fully contracted, a disorderly group of action potentials of varying rates and amplitudes should appear (a complete recruitment and interference pattern).

The pad may also comprise at least one capacitive sensor for measurement of the proper contact of the pad with the patient. The capacitive sensor may be connected to at least two complementary metal-oxide-semiconductor (CMOS) integrated circuit (IC) chips, an application-specific integrated circuit (ASIC) controller and a digital signal processor (DSP) which may be part of the control unit. The capacitive sensor may detect and measure the skin based on the different dielectric properties than the air, thus when the pad is detached from the patient a change in the signal may be detected and further processed by the control unit. The capacitance sensor may be configured in a surface capacitance or in a projected capacitance configuration. For better information about the contact and for higher safety, a single pad may comprise 3 to 30 or 4 to 20 or 5 to 18 or 6 to 16 or 7 to 14 capacitance sensors.

Memory 12 may include, for example, information about the type and shape of the pad 4, its remaining lifetime, or the time of therapy that has already been performed with the pad. The memory may also provide information about the manufacturer of the pad or information about the designated area of use on the body of the patient. The memory may include RFID, MRAM, resistors, or pins.

Neutral electrode 7 may ensure proper radiofrequency energy distribution within the patient's body for mono-polar radiofrequency systems. The neutral electrode 7 is attached to the patient's skin prior to each therapy so that the energy may be distributed between active element 13 (e.g. electrode) and neutral electrode 7. In some bipolar or multipolar radiofrequency systems, there is no need to use a neutral electrode—because radiofrequency energy is distributed between multiple active elements 13 (e.g. electrodes). Neutral electrode 7 represents an optional block of the apparatus 1 as any type of radiofrequency system can be integrated. In one aspect, the neutral electrode 7 may be part of the pad 4.

Additionally, device 1 may include one or more sensors. The sensor may provide information about at least one physical quantity and its measurement may lead to feedback which may be displayed by human machine interface 8 or indicators 17. The one or more sensors may be used for sensing delivered electromagnetic energy, impedance of the skin, resistance of the skin, temperature of the treated skin, temperature of the untreated skin, temperature of at least one layer of the skin, water content of the device, the phase angle of delivered or reflected energy, the position of the active elements 13, the position of the interconnecting block 3, temperature of the cooling media, temperature of the primary electromagnetic generator 6 and secondary generator 9 and ultrasound emitter 10 or the contact with the skin. The sensor may be a thermal, acoustic, vibration, electric, magnetic, flow, positional, optical, imaging, pressure, force, energy flux, impedance, current, Hall or proximity sensor. The sensor may be a capacitive displacement sensor, acoustic proximity sensor, gyroscope, accelerometer, magnetometer, infrared camera or thermographic camera. The sensor may be invasive or contactless. The sensor may be located on or in the pad 4, in the main unit 2, in the interconnecting block 3 or may be a part of a thermal sensor 15. One sensor may measure more than one physical quantity. For example, the sensor may include a combination of a gyroscope, an accelerometer and/or a magnetometer. Additionally, the sensor may measure one or more physical quantities of the treated skin or untreated skin.

A resistance sensor may measure skin resistance, because skin resistance may vary for different patients, as well as the humidity—wetness and sweat may influence the resistance and therefore the behavior of the skin in the energy field. Based on the measured skin resistance, the skin impedance may also be calculated.

Information from one or more sensors may be used for generation of a pathway on a model e.g. a model of the human body shown on a display of human machine interface 8. The pathway may illustrate a surface or volume of already treated tissue, presently treated tissue, tissue to be treated, or untreated tissue. A model may show a temperature map of the treated tissue providing information about the already treated tissue or untreated tissue.

The sensor may provide information about the location of bones, inflamed tissue or joints. Such types of tissue may not be targeted by electromagnetic energy due to the possibility of painful treatment. Bones, joints or inflamed tissue may be detected by any type of sensor such as an imaging sensor (ultrasound sensor, IR sensor), impedance sensor, and the like. A detected presence of these tissue types may cause general human perceptible signals or interruption of generation of electromagnetic energy. Bones may be detected by a change of impedance of the tissue or by analysis of reflected electromagnetic energy.

In one aspect the active elements 13, may be used as the sensors described above. For example, the active element 13 (e.g. electrode) may measure impedance before, during or after providing the radiofrequency energy. In addition, the active element 13 (e.g. electrode) may measure the voltage or the current passing through the patient during the electric current stimulation. Based on those information it may be possible to determine proper contact of the pad 4 or active elements 13 (e.g. electrodes) with the patient.

The patient's skin over at least one treatment portion may be pre-cooled to a selected temperature for a selected duration, the selected temperature and duration for pre-cooling may be sufficient to cool the skin to at least a selected temperature below normal body temperature. The skin may be cooled to at least the selected temperature to a depth below the at least one depth for the treatment portions so that the at least one treatment portion is substantially surrounded by cooled skin. The cooling may continue during the application of energy, and the duration of the application of energy may be greater than the thermal relaxation time of the treatment portions. Cooling may be provided by any known mechanism including water cooling, sprayed coolant, presence of an active solid cooling element (e.g. thermoelectric cooler) or air flow cooling. A cooling element may act as an optical element. Alternatively, the cooling element may be a spacer. Cooling may be provided during, before or after the treatment with electromagnetic energy. Cooling before treatment may also provide an environment for sudden heat shock, while cooling after treatment may provide faster regeneration after heat shock. The temperature of the coolant may be in the range of −200° C. to 36° C. The temperature of the cooling element during the treatment may be in the range of −80° C. to 36° C. or −70° C. to 35° C. or −60° C. to 34° C. or −20° C. to 30° C. or 0° C. to 27° C. or 5° C. to 25° C. Further, where the pad is not in contact with the patient's skin, cryogenic spray cooling, gas flow or other non-contact cooling techniques may be utilized. A cooling gel on the skin surface might also be utilized, either in addition to or instead of, one of the cooling techniques indicated above.

Figures 3A, 3B:
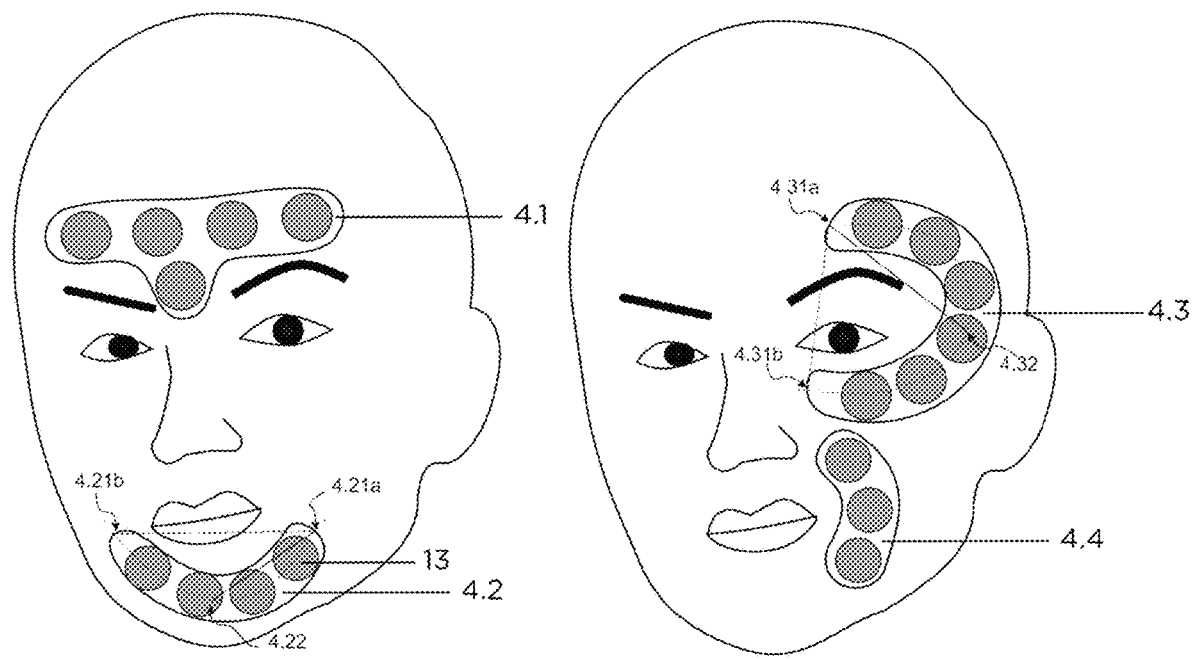
FIG. 3A represents pad shapes and layout.
FIG. 3B represents pad shapes and layout.

FIG. 3A and FIG. 3B show different shapes and layouts of pad 4 used by an apparatus for contact therapy. Pads 4 comprise at least one active element 13 (e.g. electrode) and may be available in various shapes and layouts so that they may cover a variety of different treatment areas and accommodate individual patient needs, e.g. annular, semicircular, elliptical, oblong, square, rectangular, trapezoidal, polygonal or formless (having no regular form or shape). The shapes and layouts of the pad 4 may be shaped to cover at least part of one or more of the periorbital area, the forehead (including frown lines), the jaw line, the perioral area (including Marionette lines, perioral lines—so called smoker lines, nasolabial folds, lips and chin), cheeks or submentum, etc. The shape of the pad 4 and distribution, size and number of active elements 13 (e.g. electrodes) may differ depending on the area being treated, e.g. active elements 13 inside the pad 4 may be in one line, two lines, three lines, four lines or multiple lines. The pad 4 with active elements 13 may be arranged into various shapes, e.g. in a line, where the centers of at least two active elements 13 lie in one straight line, while any additional center of an active element 13 may lie in the same or different lines inside the pad 4.

In addition, the pad 4 may be used to treat at least partially neck, bra fat, love handles, torso, back, abdomen, buttocks, thighs, calves, legs, arms, forearms, hands, fingers or body cavities (e.g. vagina, anus, mouth, inner ear etc.).

The pad 4 may have a rectangular, oblong, square, trapezoidal form, or of the form of a convex or concave polygon wherein the pad 4 may have at least two different inner angles of the convex or concave polygon structure. Additionally, the pad 4 may form at least in part the shape of a conic section (also called conic), e.g. circle, ellipse, parabola or hyperbola. The pad 4 may have at least in part one, two, three, four, five or more curvatures of a shape of an arc with the curvature k in the range of 0.002 to 10 $mm^{-1}$ or in the range of 0.004 to 5 $mm^{-1}$ or in the range of 0.005 to 3 $mm^{-1}$ or in the range of 0.006 to 2 $mm^{-1}$. The pad 4 may have at least one, two, three, four, five or more arcs with the curvature k or may have at least two different inner angles of a convex or concave polygon structure, and may be suitable for the treatment of chin, cheeks, submental area (e.g. "banana shape 1" 4.2), for treating jaw line, perioral area, Marionette lines and nasolabial folds (e.g. "banana shape 2" 4.4), for the treatment of periorbital area (e.g. "horseshoe shape" 4.3) or other regions of face and neck. The "banana shape" pad 4.2 or 4.4 may have a convex-concave shape, which means that one side is convex and the opposite side is concave, that occupies at least 5% to 50% or 10% to 60% or 15% to 70% or 20% to 90% of a total circumference of the pad 4 seen from above, wherein the shortest distance between the endpoints 4.21a and 4.21b of the "banana shape" pad 4.2 (dashed line in FIG. 3A) is longer than the shortest distance between the endpoint 4.21a or 4.21b and the middle point 4.22 of the "banana shape" (full line in pad 4.2 in FIG. 3A). The "horseshoe shape" 4.3 seen from above may have the convex-concave shape that occupies at least 15% to 50% or 20% to 60% or 25% to 70% or 30% to 90% of its total circumference, wherein the shortest distance between the endpoints 4.31a and 4.31b of the "horseshoe shape" pad 4.3 (dashed line in FIG. 3B) is equal or shorter than the shortest distance between the endpoint 4.31a or 4.31b and the middle point 4.32 of the "horseshoe shape" (full line in pad 4.3 in FIG. 3B). When seen from above, if the longest possible center curve, which may be convex or concave and whose perpendiculars at a given point have equidistant distance from perimeter edges of the pad at each of its points (dotted line in pad 4.2 in FIG. 3A), intersects the circumference of the pad 4 then this point is the endpoint of the pad, e.g. endpoint 4.21a or 4.21b. The middle point, e.g. 4.22, is then given as the middle of the center curve, wherein the total length of the center curve is given by two endpoints, e.g. 4.21a and 4.21b, thus the length of the center curve (dotted line in pad 4.2 in FIG. 3A) from point 4.21a to point 4.22 is the same as the length from point 4.21b to point 4.22. The total length of the center curve may be in the range of 0.1 to 30 cm or in the range of 0.5 to 25 cm or in the range of 1 to 20 cm.

In addition, the center curve may have at least in part circular, elliptical, parabolic, hyperbolic, exponential, convex or concave curve such that the straight line connecting endpoint of the pad 4 with the middle point of the center curve forms an angle alpha with the tangent of the middle of the center curve. The angle alpha may be in a range of 0.1° to 179° or in a range of 0.2° to 170° or in a range of 0.5° to 160° or in a range of 1° to 150°.

The pad 4 whose shape has at least two concave arcs with the curvature k or has at least two concave inner angles of the polygon structure may be suitable for the treatment of the forehead like the "T shape" 4.1 in FIG. 3A. The "T shape" 4.1 may be also characterized by the arrangement of the active elements 13 where the centers of at least two active elements 13 lie in one straight line and center of at least one additional element 13 lies in a different line.

Figure 3C:
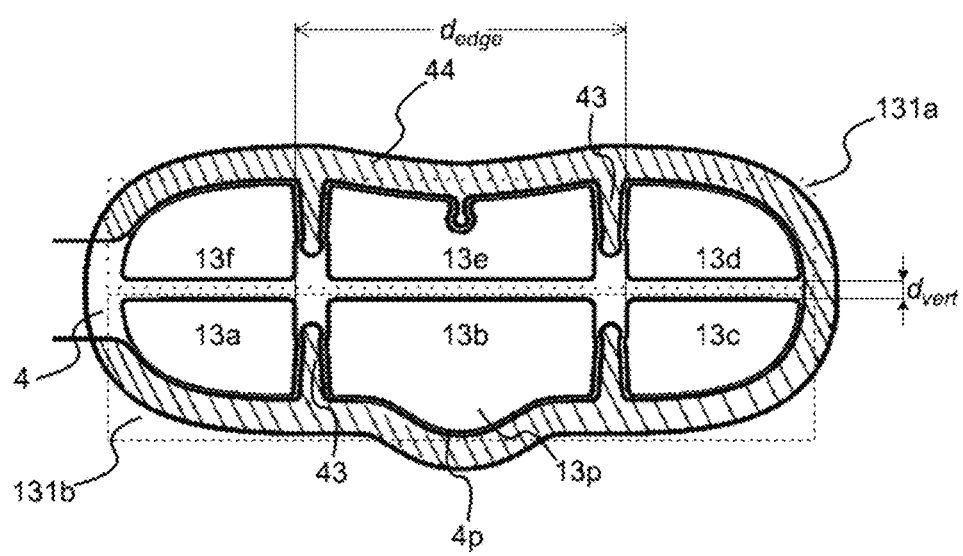
FIG. 3C represents one possible pad shape and layout for treatment of a forehead.

Another possible non-limiting configuration of the pad 4 used for the treatment of the forehead is depicted in FIG. 3C. In this non-limiting example, a forehead pad (pad 4 used for threatment of the forehead) my contain two lines of active elements 13 (e.g. electrodes)—active elements 13a-13f as shown in FIG. 3C, wherein the active elements 13a-13f in one line may be at least partially separated by slots 43 for better flexibility of the pad 4. A first line of active elements comprises active elements (e.g. electrodes) depicted in the dotted box 131a in FIG. 3C—active elements 13d, 13e and 13f. The second line of active elements (e.g. electrodes) comprises active elements depicted in the dashed box 131b in FIG. 3C—active elements 13a, 13b, 13c. Dotted and dashed boxes 131a and 131b are used only for visualization of the first and second lines of active elements (e.g. electrodes), respectively. Such pad 4 may have a shape that has a total number of convex and/or concave arcs in a range of 14 to 36 or in a range of 18 to 32 or in a range of 20 to 30 or in a range of 22 to 28 with a curvature k. Additionally, the pad 4 may have a number of concave inner angles in a range of 2 to 20 or in a range of 5 to 17 or in a range of 7 to 15 or in a range of 9 to 13, or the pad 4 may have a number of convex inner angles in a range of 2 to 20 or in a range of 5 to 17 or in a range of 10 to 16 or in a range of 11 to 15.

FIG. 3C also shows the sticker 44 on a top side of the pad 4. The top side is the opposite side from the underside (the side where the adhesive layer or the active elements may be deposited on the substrate of the pad 4) or in other words, the top side is the side of the pad 4 that is facing away from the patient during the treatment. The sticker 44 may have a bottom side and a top side, wherein the bottom side of the sticker 44 may comprise a sticking layer and the top side of the sticker 44 may comprise a non-sticking layer (eg. polyimide (PI) films, PTFE (e.g. Teflon®), epoxy, polyethylene terephthalate (PET), polyamide or PE foam).

As shown in FIG. 3C, the sticker 44 may have the same or similar shape as the pad 4 with an additional overlap over the pad 4. The overlap is hatched in FIG. 3C. The sticker 44 may be bonded to the pad 4 such that the sticking layer of the bottom side of the sticker 44 is facing toward the top side of the pad 4. The overlap of the sticker may exceed the pad 4 in the range of 0.1 to 10 cm, or in the range of 0.1 to 7 cm, or in the range of 0.2 to 5 cm, or in the range of 0.2 to 3 cm, or in the range of 0.3 to 1 cm. This overlap may also comprise an adhesive layer and may be used to form additional and more proper contact of the pad 4 with the patient. In another aspect, the sticker may have different shapes or sizes than the pad.

The forehead pad (pad 4 used for treatment of the forehead) may comprise edge active elements (e.g. electrodes) 13a, 13c, 13d and 13f and middle active elements (e.g. electrodes)—13b and 13e as shown in FIG. 3C. The forehead pad 4 may be divided into an upper side 131a with active elements (e.g. electrodes) 13d, 13e, and 13f, and bottom side 131b with active elements (e.g. electrodes) 13a, 13b, and 13c, as well as a left side with active elements (e.g. electrodes) 13a and 13f, and a right side with active elements (e.g. electrodes) 13c and 13d. Edge active elements (e.g. electrodes) 13a, 13c, 13d and 13f in the forehead pad 4 depicted in FIG. 3C may have a surface area in the range of 1 to 10 cm$^2$ or in the range of 2 to 6.5 cm$^2$ or in the range of 2.3 to 6 cm$^2$ or in the range of 2.5 to 5.5 cm$^2$, which may be the same for all edge active elements. The middle active elements (e.g. electrodes) 13b and 13e in FIG. 3C may have a same surface area as the edge active elements (e.g. electrodes) or may have a larger surface area than the edge active elements (e.g. electrodes), wherein the surface area of the middle active elements (e.g. electrodes) may be in the range of 1 to 20 cm$^2$ or in the range of 2 to 15 cm$^2$ or in the range of 3 to 12 cm$^2$ or in the range of 4 to 10 cm$^2$. In one aspect, each active element (e.g. electrode) may have a different surface area. The ratio of a surface area of one middle active element (e.g. electrode) to a surface area of one edge active element (e.g. electrode) on the forehead pad may be in a range of 0.8 to 2.5 or in a range of 1 to 2.3 or in a range of 1.1 to 2.2.

The distance $d_{edge}$ between the closest points of the bottom edge active elements (e.g. electrodes) 13a and 13c in the FIG. 3C or the upper edge active elements (e.g. electrodes) 13d and 13f in the FIG. 3C may be in the range of 2 to 8 cm or in the range of 3 to 7 cm or in the range of 4 to 6 cm or in the range of 4.5 to 5.5 cm. The distance $d_{edge}$ between the upper edge active elements (e.g. electrodes) and the distance $d_{edge}$ between the bottom edge active elements (e.g. electrodes) may be the same.

The distance $d_{vert}$ between the closest points of the upper active elements (e.g. electrodes) and the bottom active elements (e.g. electrodes) on one side (left, middle, right), e.g. the distance between active elements 13a and 13f, between active elements 13b and 13e, or between active elements 13c and 13d in FIG. 3C may be in the range of 0.5 to 20 mm or in the range of 1 to 10 mm or in the range of 1.5 to 6 mm or in the range of 2 to 5 mm. The distance $d_{vert}$ may be the same for the left, middle and right active elements.

Such distances ($d_{edge}$ and $d_{vert}$) are optimized to mitigate the edge effects (e.g. prevent creation of hot spots near edges) or leakage currents and effectively treat, e.g. the Frontalis muscle or Procerus muscle during the treatment. The edge active elements (e.g. electrodes)—13a, 13c, 13d and 13f in FIG. 3C are used for treatment of Frontalis muscle and/or Corrugator supercilii and the middle active elements (e.g. electrodes)—13b and 13e in FIG. 3C are used for treatment of Procerus muscle.

The forehead pad (pad 4 used for threatment of the forehead) in FIG. 3C also shows a possible arrangement of the bottom middle part of the pad 4 comprising the bottom middle active element (e.g. electrode) 13b. The pad 4 may comprise a convex protrusion 4p and/or concave depression in the bottom middle part. Also the active element 13b may be designed in a shape proximate to an oblong or rectangular shape with a convex protrusion 13p and/or concave depression in the middle of the bottom part of the active element 13b copying a shape of the pad 4 with the protrusion 4p and/or depression of the pad. This protrusion 4p and/or depression may serve as a focus point for a correct coupling of the pad 4 to the forehead area of the patient, wherein the protrusion 4p and/or depression should be aligned with the middle of the nose of the patient (e.g. in the middle of Procerus muscle) and at the same time the bottom edge of the pad 4 should be coupled slightly over the eyebrows of the patient.

Figure 3D:
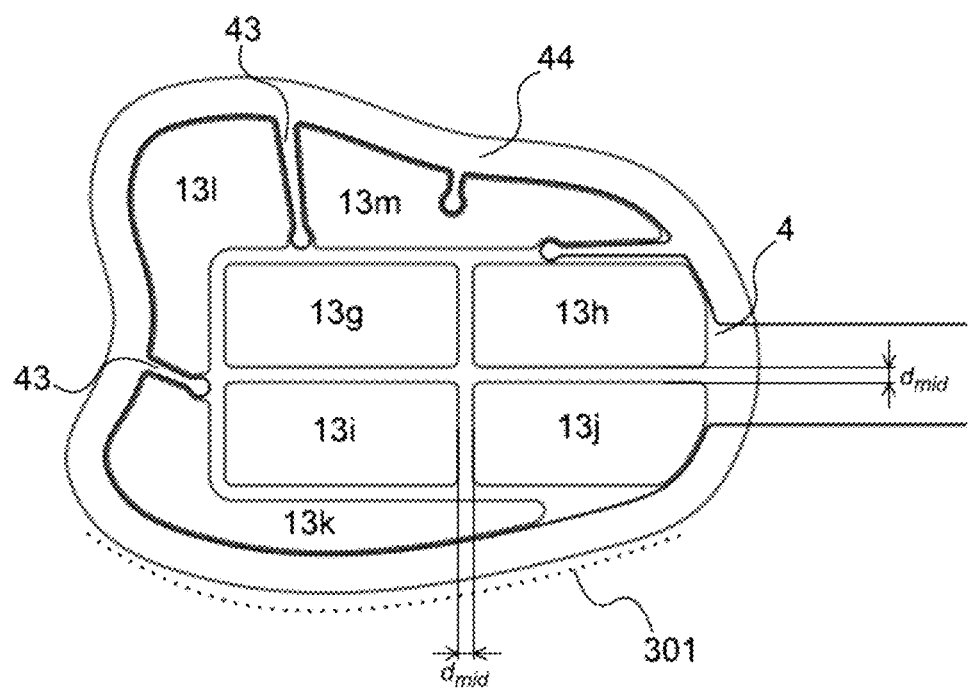
FIG. 3D represent one possible pad shape and layout for treatment of a cheek.

One possible non-limiting configuration of the pad 4 used for the treatment of the left cheek is depicted in FIG. 3D. In this non-limiting example, middle active elements (e.g. electrodes)—active elements 13g, 13h, 13i and 13j may be separated on the substrate and the distance $d_{mid}$ between the closest points of two neighboring middle active elements (e.g. electrodes) may be in the range of 0.5 to 5 mm or in the range of 0.8 to 3 mm or in the range of 1 to 2.5 mm or in the range of 1.2 to 2.3 mm. The left cheek pad (the pad 4 used for the treatment of the left cheek) depicted in FIG. 3D may be designed to be coupled to the patient such that the bottom of the pad 4 is aligned and slightly above the left part of the base of the mandible, represented by the number 301 in FIG. 3D. The middle active elements (e.g. electrodes) 13g, 13h, 13i and 13j in FIG. 3D may have a surface area in the range of 1 to 15 cm$^2$ or in the range of 2 to 8 cm$^2$ or in the range of 2.5 to 6 cm$^2$ or in the range of 3 to 5 cm$^2$. The edge active elements (e.g. electrodes) 13k, 13l and 13m may have a surface area in the range of 1 to 20 cm$^2$ or in the range of 2 to 10 cm$^2$ or in the range of 2.5 to 8 cm$^2$ or in the range of 3.5 to 7 cm$^2$. The ratio of a surface area of the edge active element (e.g. electrode)—one of 13k, 13l or 13m, to a surface area of the middle active element (e.g. electrode)—one of 13g, 13h, 13i or 13j in FIG. 3D, may be in a range of 0.5 to 3 or in a range of 0.8 to 2.5 or in a range of 1 to 2 or in a range of 1 to 1.8.

The middle active elements (e.g. electrodes) 13g, 13h, 13i and 13j in FIG. 3D are optimally configured to mitigate the edge effects (e.g. prevent creation of hot spots near edges) or leakage currents and to treat e.g. the Buccinator, Risorius, Zygomaticus and/or Masseter muscle. The middle active elements (e.g. electrodes) 13g, 13h, 13i and 13j in FIG. 3D are optimally configured to treat e.g. the Platysma, Depressor and/or Lavator labii superioris muscles. The number of the middle active elements (e.g. electrodes) may be in the range of 1 to 10, in the range of 1 to 8, in the range of 2 to 6, or in the range of 2 to 4. The number of the edge active elements (e.g. electrodes) may be in the range of 1 to 10, in the range of 1 to 7, in the range of 1 to 6, or in the range of 2 to 5.

The pad 4 used for the treatment of the right cheek may be symmetrically arranged to the left cheek pad 4 depicted in FIG. 3D.

Figure 3E:
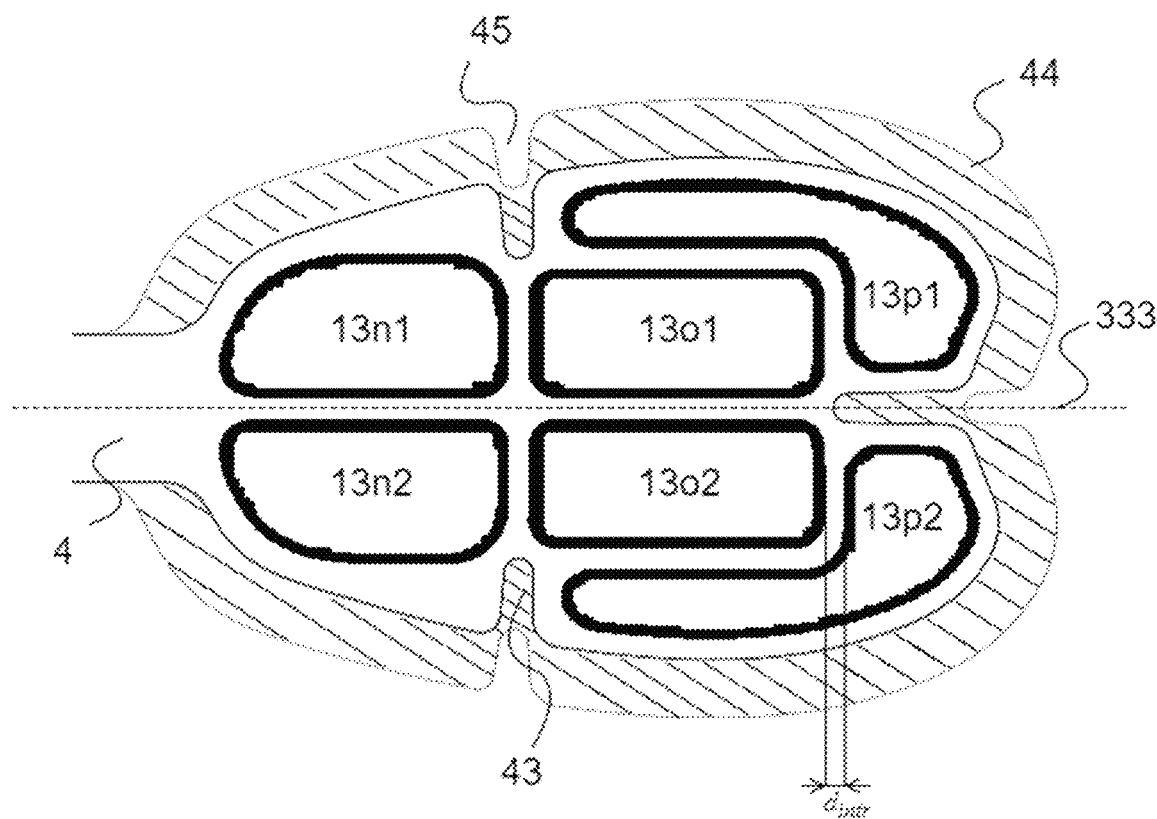
FIG. 3E represents one possible pad shape and layout for treatment of a cheek.

In one aspect, the cheek pad 4 may be symmetrical as depicted in FIG. 3E. Such symmetrical cheek pad may be used for left cheek or right cheek treatment. The symmetry is along the axis 333 (dashed line in FIG. 3E). A first line of active elements (e.g. electrodes) 13n1, 13o1 and 13p1 are above the axis 333 and the symmetrical second line of active elements (e.g. electrodes) 13n2, 13o2 and 13p2 are under the axis 333. Thus, the symmetrical cheek pad may have pair active elements (e.g. electrodes)—e.g. 13n1 and 13n2, 13o1 and 13o2, or 13p1 and 13p2, wherein the active elements (e.g. electrodes) in each pair have the same shape symmetrical to the axis 333. The area of the active elements (e.g. electrodes) may be the same or different for each active element (e.g. electrodes). In one aspect all active elements (e.g. electrodes) 13n1-13p2 may have the same surface area, wherein the surface are of one active element (e.g. electrode) is in the range of 1 to 15 cm$^2$, in the range of 2 to 8 cm$^2$, in the range of 2.5 to 6 cm$^2$, or in the range of 3 to 5 cm$^2$. In another aspect, the surface area of active elements (e.g. electrodes) 13n1-13p2 may be different for each active element (e.g. electrode) or a pair active elements (e.g. pair 13n1 and 13n2) may have the same surface area which is different than a surface area of other pair active elements (e.g. pair 13p1 and 13p2), wherein the surface area of one active element (e.g. electrode) may be in the range of 1 to 20 cm$^2$, in the range of 2 to 10 cm$^2$, or in the range of 2.5 to 8 cm$^2$, or in the range of 3.5 to 7 cm$^2$.

Inter-active elements distance $d_{intr}$ depicted in FIG. 3E is a distance between two closest points of neighboring active elements (e.g. electrodes), e.g. active element 13o1 and active element 13p1. Inter-active elements distance $d_{intr}$ may be in in the range of 0.5 to 5 mm, in the range of 0.8 to 4 mm, in the range of 1 to 3.3 mm, or in the range of 1.2 to 2.8 mm. The active elements (e.g. electrodes) 13n1-13p2 in FIG. 3E are optimally configured to mitigate the edge effects (e.g. prevent creation of hot spots near edges) or leakage currents and to treat the e.g. Buccinator, Risorius, Zygomaticus, Masseter, Platysma, Depressor and/or Lavator labii superioris muscles.

Figure 3F:
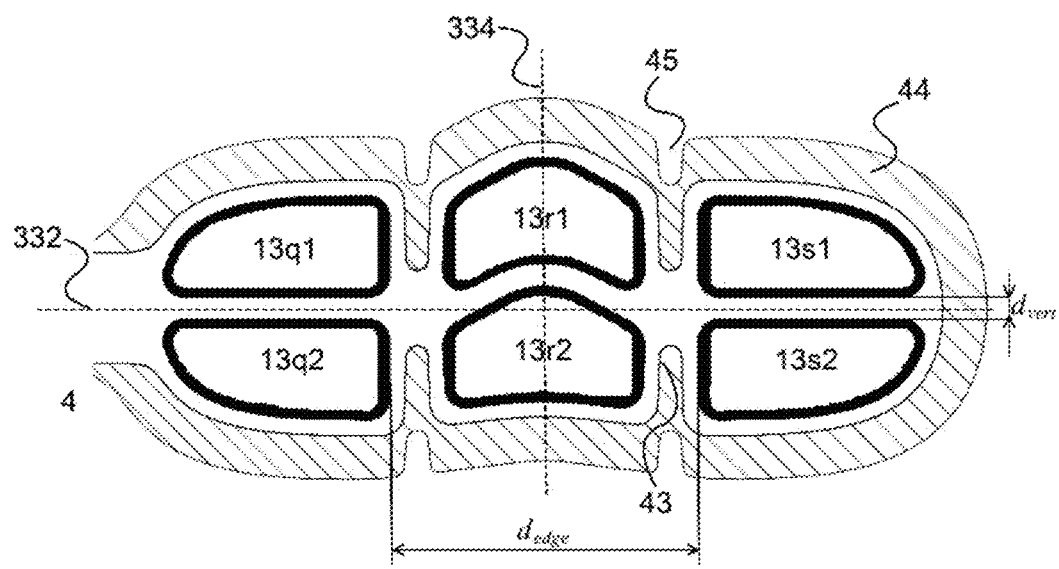
FIG. 3F represent one possible pad shape and layout for treatment of a forehead.

Another possible non-limiting configuration of the pad 4, which may be used for treatment of the forehead, is shown in FIG. 3F. The pad 4 may have a pair of left edge active elements (e.g. electrodes) 13q1 and 13q2, and a pair of right edge active elements (e.g. electrodes) 13s1 and 13s2. The left edge active elements (e.g. electrodes) 13q1 and 13q2, may be symmetrical along at least one axis, e.g. the horizontal axis 332 in FIG. 3F. The right edge active elements (e.g. electrodes) 13s1 and 13s2, may be symmetrical along at least one axis, e.g. the horizontal axis 332 in FIG. 3F. The pad 4 may have a pair of middle active elements (e.g. electrodes) 13r1 and 13r2 which may be symmetrical along the horizontal axis 332, or may be not symmetrical along the horizontal axis 332 but may be symmetrical along the vertical axis 334. In fact, the whole layout of the active elements (e.g. electrodes) on the pad 4 may be symmetrical along at least one axis, e.g. the vertical axis 334 in FIG. 3F.

The active elements (e.g. electrodes) may have the same or different surface area, or pair active elements (e.g. active elements 13q1 and 13q2) may have the same surface area, which may be different than the surface area of another pair of active elements (e.g. active elements 13r1 and 13r2). The surface area of the active element (e.g. electrode) is in the range of 1 to 10 cm2 or in the range of 2 to 6.5 cm2 or in the range of 2.3 to 6 cm2 or in the range of 2.5 to 5.5 cm2. The active elements (e.g. electrodes) may have the distances $d_{edge}$ and $d_{vert}$ between them as described above, which are optimized to mitigate the edge effects (e.g. prevent creation of hot spots near edges) or leakage currents and effectively treat e.g. the Frontalis muscle or Procerus muscle during the treatment. Some active elements (e.g. electrodes) may be also at least partially separated by the slots 43 of the pad, e.g. active elements 13r2 and 13s2 for better coupling of the pad 4 with the patient.

All non-limiting examples of the pad shown in FIGS. 3C-3F also show the sticker 44 on a top side of the pad 4. The sticker may have the same or similar shape as the pad 4 with an additional overlap over the pad 4. The overlap is hatched in FIGS. 3C-3F. The overlap of the sticker may exceed the pad 4 in the range of 0.1 to 10 cm, or in the range of 0.1 to 7 cm, or in the range of 0.2 to 5 cm, or in the range of 0.2 to 3 cm, or in the range of 0.3 to 1 cm. In one aspect, the overlap of the sticker may also have sticker slots 45 (see e.g. FIGS. 3E and 3F) close to the pad slots 43 allowing better adhesion of the overlap of the sticker 44 to the uneven areas of the body part.

A treatment pad suitable for a treatment of submental area may cover the submentum as well as part of the neck. In one aspect, such a submentum pad may comprise active elements (e.g. electrodes) delivering energy suitable to provide contractions (e.g. electric current) only to the submentum (submental and submandibular triangle) and other active elements (e.g. electrodes) delivering energy suitable for heating (e.g. radiofrequency) of the submentum and/or neck (e.g. carotid triangle, muscular triangle. Such a layout of the pad may be suitable for treatment of double chin, wherein the heating is evenly distributed under the pad and the contractions are provided only to some submentum muscles (e.g. digastric, mylohyoid and/or stylohyoid muscle), which may lay above the hyoid bone. In one aspect, the submentum pad may be symmetrical.

Pads may have different sizes with the surface areas ranging from 0.1 to 150 cm$^2$ or from 0.2 to 125 cm$^2$ or from 0.5 to 100 cm$^2$ or in the range of 1 to 50 cm$^2$ or in the range of 10 to 50 cm$^2$ or in the range of 15 to 47 cm$^2$ or in the range of 18 to 45 cm$^2$. The pad may occupy approximately 1 to 99% or 1 to 80% or 1 to 60% or 1 to 50% of the face. The number of active elements 13 (e.g. electrodes) within a single pad 4 ranges from 1 to 100 or from 1 to 80 or from 1 to 60 or from 2-20 or from 3 to 10 or from 4 to 9. A thickness at least in a part of the pad 4 may be in the range of 0.01 to 15 mm or in the range of 0.02 to 10 mm or in the range of 0.05 to 7 mm or in the range of 0.1 to 2 mm.

In one aspect, the pad 4 may comprise one active element 13 (e.g. electrode) that provides one or more treatments (e.g. radiofrequency energy and electric current), whereas a plurality of such pads may be used to treat the same area during one treatment. For example instead of using one pad 4 with six active elements 13 (e.g. electrodes) which may be used for treatment of a forehead, six pads 4 each with one active element 13 (e.g. electrode) may be used for the same treatment. In another aspect, the pad 4 may comprise one active element 13 (e.g. electrode) that provides one type of treatment/energy and plurality of pads 4 that provides the same or different treatment/energy may be used to treat the same area during one treatment. For example, instead of pad 4 with one active element 13 (e.g. electrode) that provides radiofrequency energy and electric current, it may be possible to use two pads 4, one with active element 13 (e.g. electrode) that provides radiofrequency energy and the other one with active element 13 (e.g. electrode) that provides electric current.

Alternatively, only one or more active elements 13 (e.g. electrodes) themselves may be used instead of the pad 4 with a substrate and the active element 13. In one aspect, the active element 13 (e.g. electrode) that provides one or more treatments (e.g. radiofrequency energy and electric current) may be used to treat a body part of the patient. In another aspect, a plurality of active elements 13 (e.g. electrodes) may be used to treat the same body part during one treatment. For example instead of using one pad 4 with six active elements 13 (e.g. electrodes) which may be used for treatment of a forehead, six individual active elements 13 (e.g. electrodes) may be used for the same treatment. In another aspect, the active element 13 (e.g. electrode) may provide one type of treatment/energy and a plurality of active elements 13 (e.g. electrodes) that provides the same or different treatment/energy may be used to treat the same area during one treatment. For example, instead of using pad 4 with at least one active element 13 (e.g. electrode) that provides radiofrequency energy and electric current, it may be possible to use at least two individual active elements (e.g. electrodes), at least one active element 13 (e.g. electrode) that provides radiofrequency energy and at least one active element 13 (e.g. electrode) that provides electric current.

In one aspect, the active elements 13 (e.g. electrodes or coils) may overlap each other at least partially. For example, the electrode may be at least partially situated under or over the coil in the pad 4.

Furthermore the pads 4 may have a shape that at least partially replicates the shape of galea aponeurotica, procerus, levatar labii superioris alaeque nasi, nasalis, lavator labii superioris, zygomaticus minor, zygomaticus major, levator angulis oris, risorius, platysma, depressor anguli oris, depressor labii inferioris, occipitofrontalis (frontal belly), currugator supercilii, orbicularis oculi, buccinator, masseter, orbicularis oris or mentalis muscle when the pad 4 is attached to the surface of the patient skin.

The pad 4 may be characterized by at least one aforementioned aspect or by a combination of more than one aforementioned aspect or by a combination of all aforementioned aspects.

The electromagnetic energy generator 6 or the secondary generator 9 inside the main case may generate an electromagnetic or secondary energy (e.g. electric current) which may be delivered via a conductive lead to at least one active element 13 (e.g. electrode) attached to the skin, respectively. The active element 13 may deliver energy through its entire surface or by means of a so-called fractional arrangement. Active element 13 may be an active electrode in a monopolar, unipolar, bipolar or multipolar radiofrequency system. In the monopolar radiofrequency system, energy is delivered between an active electrode (active element 13) and a neutral electrode 7 with a much larger surface area. Due to mutual distance and difference between the surface area of the active and neutral electrode, energy is concentrated under the active electrode enabling it to heat the treated area. In the monopolar radiofrequency system, the energy may be delivered with the frequency in the range of 100 kHz to 550 MHz or in the range of 200 kHz to 300 MHz or in the range of 250 kHz to 100 MHz or in the range of 300 kHz to 50 MHz or in the range of 350 kHz to 14 MHz. In the unipolar, bipolar or multipolar radiofrequency system, there is no need for neutral electrode 7. In the bipolar and multipolar radiofrequency system, energy is delivered between two and multiple active electrodes with similar surface area, respectively. The distance between these electrodes determines the depth of energy penetration. In the unipolar radiofrequency system, only a single active electrode is incorporated and energy is delivered to the tissue and environment surrounding the active electrode. The distance between the two nearest active elements 13 (e.g. the nearest neighboring sides of electrodes) in one pad 4 may be in the range of 0.1 to 100 mm or in the range of 0.3 to 70 mm or in the range of 0.5 to 60 mm or in the range of 0.7 to 30 mm or in the range of 1 to 10 mm or in the range of 1 to 5 mm. The distance between the two nearest neighboring sides of the electrodes may mean the distance between the two nearest points of neighboring electrodes.

A distance between the nearest point of the active element 13 (e.g. electrode) and the nearest edge of the pad 4 may be in the range of 0.1 to 10 mm or in the range of 0.5 to 5 mm or in the range of 1 to 4 mm or in the range of 1 to 3 mm.

FIG. 4A-D represents a side view of possible configurations of the pad 4 configured for contact therapy. Pads 4 may be made of flexible substrate material 42—polyimide (PI) films, PTFE (e.g. Teflon®), PET, epoxy or PE foam with an additional adhesive layer 40 on the underside. They may be of different shapes to allow the operator to choose according to the area to be treated. Active elements 13 (e.g. electrodes) may have a circumference of annular, semicircular, elliptical, oblong, square, rectangular, trapezoidal or polygonal shape with a surface area in the range from 0.1 to 70 cm$^2$ or from 0.5 to 50 cm$^2$ or from 1 to 25 cm$^2$ or from 1 to 10 cm$^2$ or from 2 to 9.5 cm$^2$ or from 2.5 to 9 cm$^2$. The material used for active elements (e.g. electrodes) may be copper, aluminum, lead or any other conductive medium that can be deposited or integrated in the pad 4. Furthermore the active elements 13 (e.g. electrodes) may be made of silver, gold or graphite. Electrodes in the pad 4 may be printed by means of biocompatible ink, such as silver ink, graphite ink or a combination of inks of different conductive materials.

In some aspects, active elements 13 (e.g. electrodes) may be flexible as well. A stiffness of the pad 4, the flexible substrate, or the active elements 13 (e.g. electrodes) may be in a range of shore OO10 to shore D80, in a range of shore OO30 to shore A100, in the range of shore A10 to shore A80, or in the range of shore A20 to A70. In another aspect, the pad 4 may be made of flexible substrate with rigid active elements 13 (e.g. electrodes) or some active elements 13 (e.g. electrodes) may be rigid and some may be flexible with the above mentioned shore ranges (e.g. RF electrodes may be rigid and the electrodes for electrotherapy may be flexible and vice versa).

In one aspect, active elements 13 (e.g. electrodes) suitable for one treatment (e.g. radiofrequency) may have different shapes and surface areas than the active elements 13 (e.g. electrodes) suitable for second treatment (e.g. electric current). For example, the radiofrequency electrodes may have a larger surface area than the electrotherapy electrodes.

The thickness of the active elements 13 (e.g. electrode) may be in the range of 1 μm to 500 μm, in the range of 2 μm to 400 μm, in the range of 3 μm to 300 μm, or in the range of 5 μm to 100 μm. In another aspect, the electrode thickness may be in the range of 0.2 mm to 10 mm, in the range of 0.4 mm to 8 mm, or in the range of 0.5 mm to 5 mm.

In one aspect, the active elements 13 (e.g. electrodes) may have a sandwich structure where multiple conductive materials are deposited gradually on each other, e.g. a copper-nickel-gold structure. For example the copper may be deposited on the substrate with a thickness in the range of 5 to 100 μm or in the range of 15 to 55 μm or in the range of 25 to 45 μm. The nickel may be deposited on the copper with a thickness in the range of 0.1 to 15 μm or in the range of 0.5 to 8 μm or in the range of 1 to 6 μm. And the gold may be deposited on the nickel with a thickness in the range of 25 to 200 nm or in the range of 50 to 100 nm or in the range of 60 to 90 nm. Such a sandwich structure may be made for example by an ENIG process.

In another aspect, the active elements 13 (e.g. electrodes) may be made of copper and covered with another conductive layer, e.g. silver or silver-chloride ink, carbon paste, or aluminum segments coupled to the copper by conductive glue. Yet in another aspect the electrodes may be printed e.g. by a silver ink, a silver-chloride ink, or a carbon paste with the electrode thickness in the range of 1 to 100 μm or in the range of 5 to 55 μm or in the range of 8 to 45 μm.

The active element 13 (e.g. electrode) may have a shape that has a total number of convex or concave arcs in a range of 1 to 12 or in a range of 2 to 10 or in a range of 3 to 9 or in a range of 4 to 8. Additionally, the active element (e.g. electrode) may have a number of concave inner angles in a range of 1 to 7 or in a range of 1 to 6 or in a range of 1 to 5 or in a range of 2 to 4, or the active element (e.g. electrode) may have a number of convex inner angles in a range of 1 to 10 or in a range of 1 to 9 or in a range of 2 to 8 in a range of 3 to 7. A possible arrangement of convex-concave active elements 13 (e.g. electrodes) is depicted in FIG. 3C.

The active element 13 (e.g. electrode providing radiofrequency energy and/or electric current) may be full-area electrode that has a full active surface. This means that the whole surface of the electrode facing the patient is made of conductive material deposited or integrated in the pad 4 as mentioned above.

In one aspect, the electrode (made of conductive material) facing the patient may be with e.g. one or more apertures, cutouts and/or protrusions configured for example to improve flexibility of the electrode and/or pad, and/or reduce the edge effects and/or improve homogeneity of delivered energy density and/or improve homogeneity of provided treatment. Apertures may be an opening in the body of the electrode. A cutout may be an opening in the body of the electrode along the border of the electrode. Openings in the body of the electrode may be defined by view from floor projections, which shows a view of the electrode from above. The openings, e.g. apertures, cutouts and/or areas outside of protrusions may be filed by air, dielectric material, insulation material, substrate of the pad, air or hydrogel. The electrode is therefore segmented in comparison to a regular electrode by disruption of the surface area (i.e., an electrode with no apertures or cutouts). The two or more apertures or cutouts of the one electrode may be asymmetrical. The one or more aperture and cutout may have e.g. rectangular or circular shape. The apertures and/or cutouts may have regular, irregular, symmetrical and/or asymmetrical shapes. When the electrode includes two or more apertures or cutouts, the apertures or cutouts may have the same point of symmetry and/or line of symmetry. The distance between two closest points located on the borders of two different apertures and/or cutouts of the electrode may be in a range from 1 µm to 10 mm or from 10 µm to 8 mm or from 20 µm to 5 mm or from 50 µm to 3 mm or from 100 µm to 2 mm.

Figure 9C:
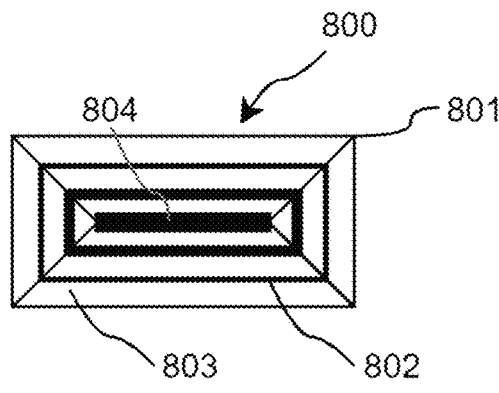
FIG. 9C is an illustration of a framed grated electrode with thinning conductive lines.

The active element (e.g. electrode) with one or more openings (e.g. apertures and/or cutouts) and/or protrusions may be framed by the conductive material and the inside of the frame may have a combination of conductive material and the openings. As shown in FIGS. 9A-9C and 9I, the frame 801 may create the utmost circumference of the electrode 800 from the side facing the patient. The frame 801 may have a form of annular, semicircular, elliptical, oblong, square, rectangular, trapezoidal or polygonal shape. The inside of the frame 801 may have a structure of a grid 802 as shown in FIGS. 9A and 9B with the apertures 803. The frame 801 and the grid lines 802 are made of conductive material and are parts of the electrode 800. The frame 801 may be of the same thickness as the thickness of the grid lines 802 or the thickness of the frame 801 may be thicker than the grid lines 802 in the range of 1% to 2000% or in the range of 10% to 1000% or in the range of 20% to 500% or in the range of 50% to 200%. Additionally the frame 801 may be thinner than the grid lines 802 in the range of 0.01 times to 20 times or in the range of 0.1 times to 10 times or in the range of 0.2 times to 5 times or in the range of 0.5 times to 2 times.

Figure 9D:
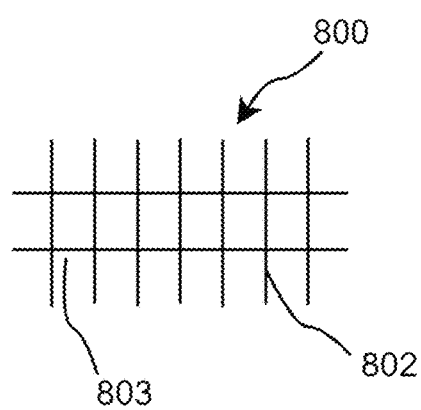
FIG. 9D is an illustration of a non-framed grated electrode.
Figure 9E:
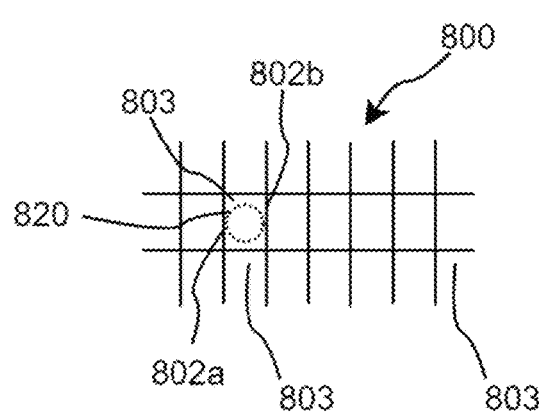
FIG. 9E is an illustration of an electrode with openings.
Figure 9F:
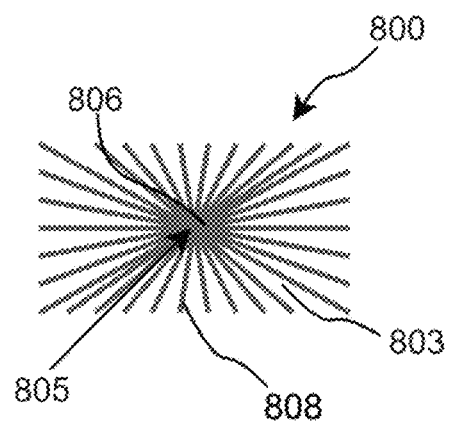
FIG. 9F is one possible illustration of an electrode.
Figure 9G:
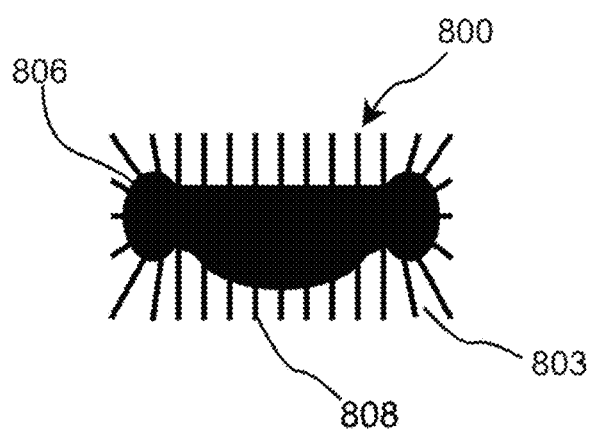
FIG. 9G is another illustration of an electrode.
Figure 9H:
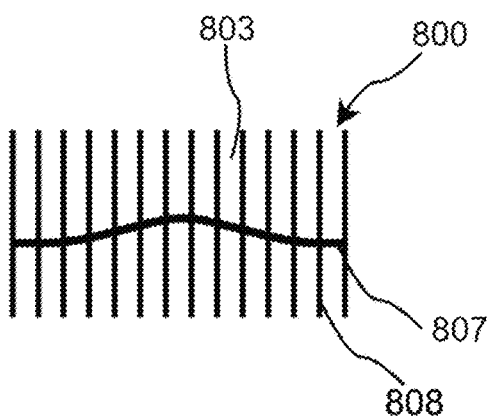
FIG. 9H is another illustration of an electrode.
Figure 9I:
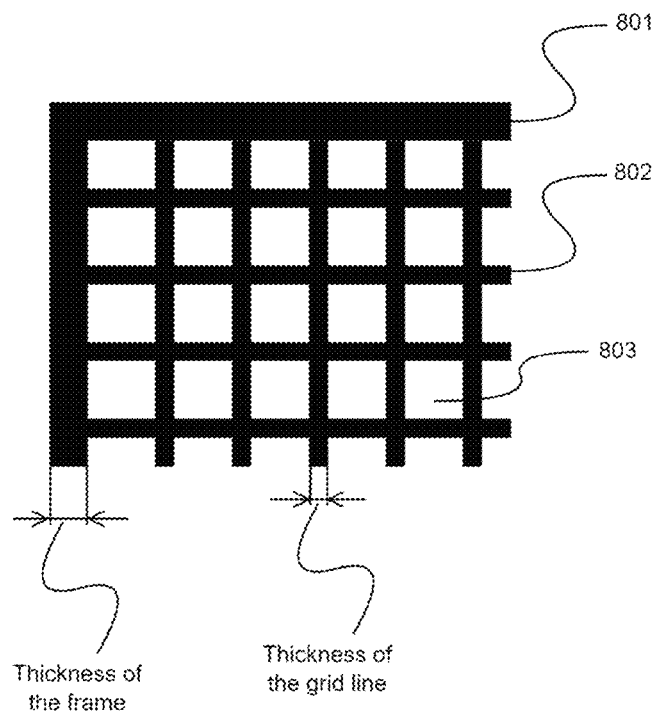
FIG. 9I illustrates a detail of a framed grated electrode

The thickness of the frame 801, as depicted in FIGS. 9A-9C and FIG. 9I, may be in a range of 0.1 to 5 mm, in a range of 0.5 to 2.3 mm, in a range of 0.6 to 1.9 mm, or in a range of 0.8 to 1.6 mm. The thickness of the grid lines 802, as depicted in FIGS. 9A-9I, may have the thickness in a range of 0.01 to 2.3 mm, in a range of 0.05 to 1.1 mm, in a range of 0.1 to 0.8 mm, or in a range of 0.2 to 0.6 mm. The thickness of the frame 801 and the grid lines 802 is illustrated in FIG. 9I, which is a zoom of the electrode 800 with the frame 801, the grid lines 802 and the apertures 803. It may be also possible to design the electrode such that the conductive material of the electrode is getting thinner from the center 804 of the electrode 800 as shown in FIG. 9C. The thinning step between adjacent grid lines 802 in the direction from the center 804 towards frame 801 may be in the range of 0.1 times to 10 times or in the range of 0.2 times to 5 times or in the range of 0.5 times to 2 times with the frame 801 having the thinnest line of conductive material.

In a first aspect, the total area of the electrode 800 (comprising the frame 801 and the grid lines 802) and all apertures 803 inside the frame 801 of said electrode 800 may be in the range of 1 to 15 cm² or in the range of 2 to 8 cm² or in the range of 2.5 to 6 cm² or in the range of 3 to 5 cm².

In a second aspect, the total area of the electrode 800 (comprising the frame 801 and the grid lines 802) and all apertures 803 inside the frame 801 of said electrode 800 may be in the range of 1 to 20 cm² or in the range of 2 to 10 cm² or in the range of 2.5 to 8 cm² or in the range of 3.5 to 7 cm².

In a third aspect, the total area of the electrode 800 (comprising the frame 801 and the grid lines 802) and all apertures 803 inside the frame 801 of said electrode 800 may be in the range of 1 to 10 cm² or in the range of 2 to 6.5 cm² or in the range of 2.3 to 6 cm² or in the range of 2.5 to 5.5 cm².

In a fourth aspect, the total area of the electrode 800 (comprising the frame 801 and the grid lines 802) and all apertures 803 inside the frame 801 of said electrode 800 may be in the range of 1 to 20 cm² or in the range of 2 to 15 cm² or in the range of 3 to 12 cm² or in the range of 4 to 10 cm².

A ratio of the area of the conductive material of the electrode 800 (i.e. the frame 801 and the gridlines 802) to the total area of all apertures inside the frame 801 of the electrode 800 may be in the range of 1% to 50%, or in the range of 2% to 45% or in the range of 5% to 40% or in the range of 8% to 35% or in the range of 10% to 33%. Additionally the ratio may be in the range of 1% to 20%, or in the range of 10% to 40% or in the range of 33% to 67% or in the range of 50% to 70% or in the range of 66% to 100%.

Alternatively, the electrode 800 may not be framed, e.g. it may have a form of a grid with no boundaries formed by openings 803 as shown in FIG. 9D. A ratio of conductive material to cutouts and/or apertures of the electrode may be in the range of 1% to 50%, or in the range of 2% to 45% or in the range of 5% to 40% or in the range of 8% to 35% or in the range of 10% to 33%. Additionally, the ratio of conductive material to openings of the electrode may be in the range of 1% to 20%, or in the range of 10% to 40% or in the range of 33% to 67% or in the range of 50% to 70% or in the range of 66% to 100%. Such a grated electrode may be very advantageous. It may be much more flexible, it may ensure contact with the patient that is more proper and it may have much better self-cooling properties than full-area electrode.

With reference to FIG. 9E, a distance between the two closest parallel grid lines 802a and 802b may be illustrated by at least one circle 820, which may be hypothetically inscribed into an aperture and/or cutout 803 and between the two closest parallel grid lines 802a and 802b and have at least one tangential point located on the first grid line 802a and at least one tangential point located on the second grid line 802b, thus having a diameter equal to the distance between the two closest parallel grid lines 802a and 802b. The at least one hypothetical circle 820 may have a diameter in a range from 0.001 to 10 mm or 0.005 mm to 9 mm, or from 0.01 mm to 8 mm or 0.05 mm to 7 mm or from 0.1 mm to 6 mm, or from 0.2 mm to 5 mm or from 0.3 mm to 5 mm or from 0.5 mm to 5 mm.

With reference to FIG. 9F, in one aspect, an electrode 800 may have multiple protrusions in the form of radial conductive lines 808 separated by cutouts 803, wherein the multiple radial conductive lines 808 are projected from one point of the electrode 805. The multiple radial conductive lines 808 are merged near the point 805 of the electrode and together create a full conductive surface 810 around the point of the electrode 805. The radial conductive lines 808 projected from the point 805 may have the same length or may have different lengths. Additionally, some of the radial conductive lines 808 projected from the point 805 may have the same length and some may have different lengths.

With reference to FIG. 9G, in another aspect, the electrode 800 may have a base part 806 of a defined shape and protrusions (radial conductive lines) 808 separated by cutouts 803. The base part 806 may have a shape of annular, semicircular, elliptical, oblong, square, rectangular, trapezoidal or polygonal. The base part 806 may be connected to the conductive leads.

With reference to FIG. 9H, in yet in another aspect, the electrode 800 may have a base conductive line 807 and multiple protrusions (radial conductive lines) 808 separated by cutouts 803. The base conductive line 807 is connected to all the radial conductive lines 808 as shown in FIG. 9H. The base conductive line may also be connected to the conductive lead. The radial conductive lines 808 emerging from the base conductive line 807 may have the same lengths and/or may have different lengths.

The distance between two closest protrusions 808 may be illustrated as at least one circle (similarly to the circle 820 in FIG. 9E), which may be hypothetically inscribed into an aperture and/or cutout 803 and between two closest protrusions 808 and have at least one tangential point located on the first protrusion and at least one tangential point located on the second protrusion, thus having a diameter equal to the distance between the two closest protrusions. The at least one circle may have a diameter in a range from 0.001 to 10 mm or 0.005 mm to 9 mm, or from 0.01 mm to 8 mm or 0.05 mm to 7 mm or from 0.1 mm to 6 mm, or from 0.2 mm to 5 mm or from 0.3 mm to 5 mm or from 0.5 mm to 5 mm.

The protrusions 808 or cutouts 803 may have a symmetrical, asymmetrical, irregular and/or regular shape. The size, shape and/or symmetry of individual radial conductive lines may be the same and/or different across the electrode. For example each protrusion 808 may have the same shape, the same dimension, the same direction and/or symmetry. The protrusions 808 may be characterized by a thickness and a length of the protrusion, wherein the length is larger than the thickness by factor in the range of 2 to 100, or in the range of 4 to 80, or in the range of 5 to 70. The thickness of a protrusion may be in the range of 1 μm to 5 mm or in the range of 20 μm to 4 mm or in the range of 50 μm to 3 mm or in the range of 100 μm to 2.5 mm or in the range of 120 μm to 2 mm or in the range of 150 μm to 1.5 mm or in the range of 200 μm to 1 mm. The length of the protrusions may be in the range of 0.05 to 50 mm or in the range of 0.1 to 30 mm or in the range of 0.5 to 20 mm. The number of protrusions that one electrode may comprise may be in a range of 1 to 1000, or of 5 to 500, or of 10 to 300, or of 15 to 250, or of 20 to 240.

The surface area of the electrode 800 with the protrusions 808 may be in the range of 0.1 to 10 cm$^2$ or in the range of 0.3 to 9.5 cm$^2$ or in the range of 0.4 to 9 cm$^2$ or in the range of 0.5 to 8.5 cm$^2$.

In addition, all the possible electrode arrangements depicted in FIG. 9F-H may be framed with a conductive frame 801, e.g. as shown in FIG. 9A, wherein the frame 801 is also a part of the electrode.

The total number of apertures and/or cutouts in one electrode regardless of the parallel cuts may be in a range of 5 to 250, or of 10 to 200, or of 15 to 170, or of 20 to 150, or of 300 to 1500, or of 400 to 1400, or of 500 to 1300, or of 600 to 1200.

In one aspect, where one or more active elements are in the form of an electrode, which is grated (FIGS. 9A-9D), the energy flux of one or more grated electrodes may be calculated as an energy flux of the grid 802 and/or the frame 801 of the active element and may be in the range of 0.001 W/cm$^2$ to 1500 W/cm$^2$ or 0.01 W/cm$^2$ to 1000 W/cm$^2$ or 0.5 W/cm$^2$ to 500 W/cm$^2$ or 0.5 W/cm$^2$ to 200 W/cm$^2$ or 0.5 W/cm$^2$ to 100 W/cm$^2$ or 1 W/cm$^2$ to 70 W/cm$^2$.

In another aspect, where one or more active elements are in the form of an electrode with openings and/or protrusions (FIGS. 9F-9H), the energy flux of one or more protruded electrodes may be calculated as an energy flux of the base part 806 or base conductive line 807 and the protrusions 808 of the active element and may be in the range of 0.001 W/cm$^2$ to 1500 W/cm$^2$ or 0.01 W/cm$^2$ to 1000 W/cm$^2$ or 0.5 W/cm$^2$ to 500 W/cm$^2$ or 0.5 W/cm$^2$ to 200 W/cm$^2$ or 0.5 W/cm$^2$ to 100 W/cm$^2$ or 1 W/cm$^2$ to 70 W/cm$^2$.

Figure 4A:
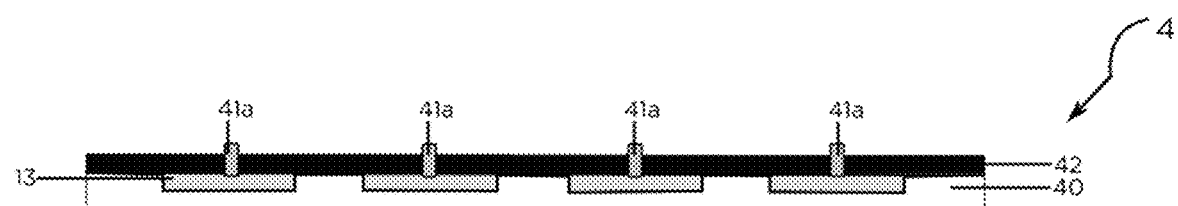
FIG. 4A, represent side views of the pad intended for contact therapy.
Figure 4B:
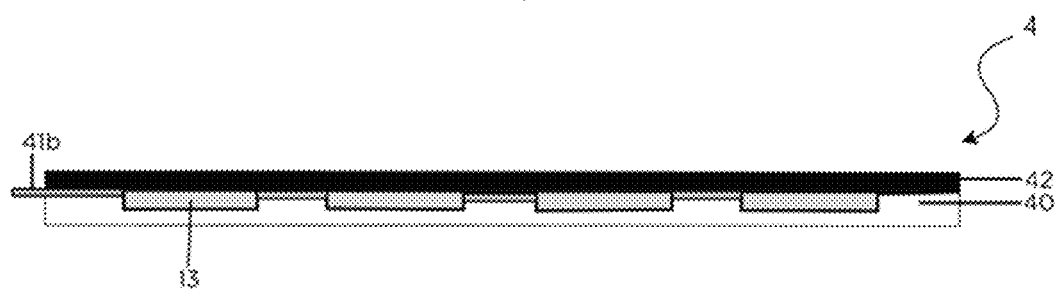
FIG. 4B, represent side views of the pad intended for contact therapy.

As shown in FIGS. 4A and 4B, the active elements 13 (e.g. electrode) may be partially embedded within the flexible substrate layer 42 or adhesive layer 40 or in the interface of the flexible substrate layer 42 and adhesive layer 40. The active elements 13 (e.g. electrode) may be supplied and controlled independently by multiple conductive leads 41a (FIG. 4A) or they may be conductively interconnected and supplied/controlled via a single conductive lead 41b (FIG. 4B). The multiple conductive leads 41a may be connected to the active elements 13 (e.g. electrode) via a free space (e.g. hole) in the flexible substrate layer 42. The free space (e.g. hole) may have dimensions such that each conductive lead 41a may fit tightly into the substrate layer 42, e.g. the conductive lead 41a may be encapsulated by a flexible substrate layer 42. Furthermore, the free space (e.g. hole) itself may be metalized and serve as a connection between respective conductive leads 41a and active elements 13 (e.g. electrodes). As shown in FIG. 4A, the active elements 13 (e.g. electrodes) may also be deposited on the underside of the flexible substrate 42 and may be covered by the adhesive layer 40 on the sides, which are not coupled to the substrate 42.

Figure 4C:
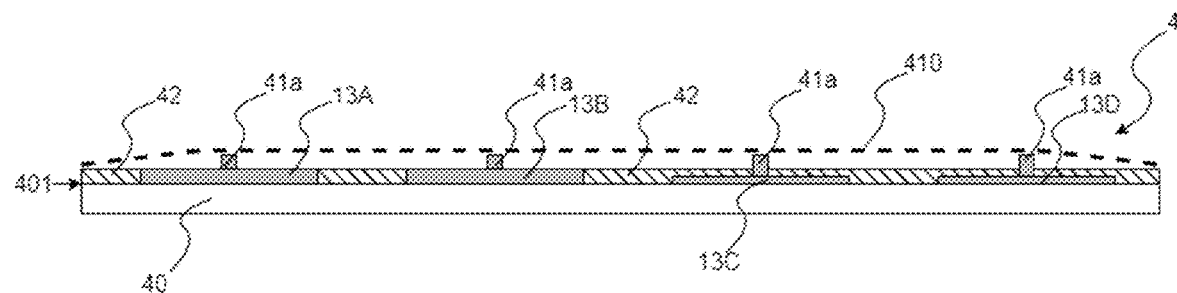
FIG. 4C, represent side views of the pad intended for contact therapy.

In another aspect, the active elements 13 (e.g. electrodes) may be embedded in the flexible substrate 42 such, that the underside of the substrate 401 and the underside of the active elements 13A-D are in one plane, as shown in FIG. 4C. For clarity, the flexible substrate 42 is hatched in FIG. 4C. The substrate 42 may have no free space for conductive leads 41a, as the conductive lead may be directly coupled to the top side of the active element (e.g. electrode) as shown in active elements 13A and 13B in FIG. 4C. Alternatively, the flexible substrate may have a free space (e.g. hole or metalized hole) for coupling the conductive leads 41a to the active elements (e.g. electrodes), which may be thinner than the substrate, as shown in active elements 13C and 13D in FIG. 4C.

Figure 4D:
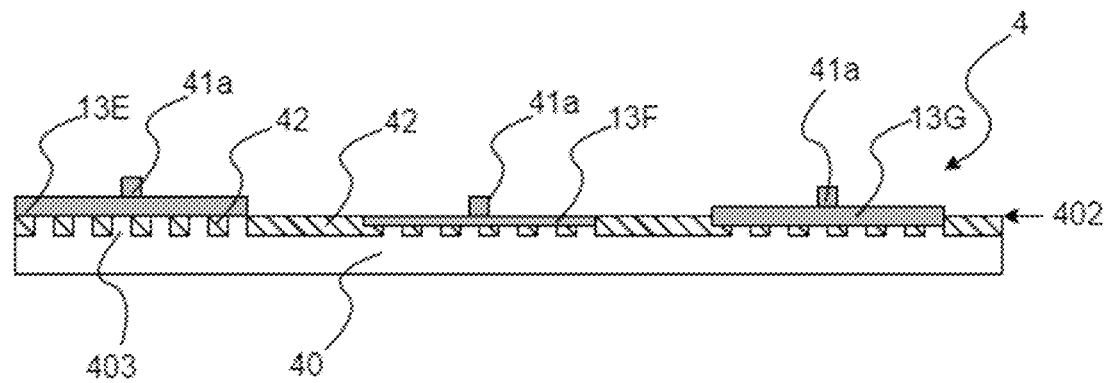
FIG. 4D represent side views of the pad intended for contact therapy.

Another possible arrangement of the active elements (e.g. electrodes) in the pad 4 is represented in FIG. 4D. In a first aspect, the active element 13E may be deposited on the top side of the substrate 402 such, that the underside of the active element 13E is deposited on the top side of the substrate 402, creating an interface of the active element 13E and substrate 42 on the top side of the substrate 402. In a second aspect, the active element 13F may be embedded in the substrate 42 from the top side of the substrate 402, such that the top side of the active element (e.g. electrode) and the top side of the substrate 402 lies in one plane. In this case, the thickness of the active element 13F is less than thickness of the substrate 42. In a third aspect the active element 13G may be deposited on the top side of the surface 402 similarly to the active element 13E but even more, the active element 13G is partially embedded in the substrate 42 from the top side of the substrate. In all these cases (active elements 13E-G), the substrate 42 is perforated allowing the coupling of adhesive layer 40 with the active elements 13E-G through the perforations 403.

Alternatively, the active element (e.g. electrode) may be fully embedded in the substrate and protrude from its top side or underside. Thus, the thickness of the active element (e.g. electrode) may be bigger than the thickness of the substrate.

In addition, combinations of pad 4 structures mentioned above may be possible, e.g. one active element (e.g. first electrode) is deposited on the underside of the pad 4 and another active element (e.g. second electrode) is embedded in the pad 4.

In case of a single conductive lead connection, the active elements 13 (e.g. electrode) may be partially embedded inside the flexible substrate 42 or adhesive layer 40 or in the interface of the flexible substrate layer 42 and adhesive layer 40, and the active elements 13 (e.g. electrode) may be connected via single conductive lead 41b which may be situated in the flexible substrate 42 or at the interface of the flexible substrate 42 and adhesive layer 40, as shown in FIG. 4B. The single conductive lead 41b may leave the pad 4 on its lateral or top side in a direction away from the patient. In both cases the conductive lead 41a or 41b does not come into contact with the treatment area.

Additionally, the active elements 13 (e.g. electrode) may be partially embedded within the flexible substrate 42 and the adhesive layer 40 may surround the active elements 13 such that a surface of active elements 13 may be at least partially in direct contact with the surface of a treatment area.

Moreover, the top side of the pad 4 may be protected by a cover layer 410, which is shown for simplicity only in FIG. 4C.

Figure 4E:
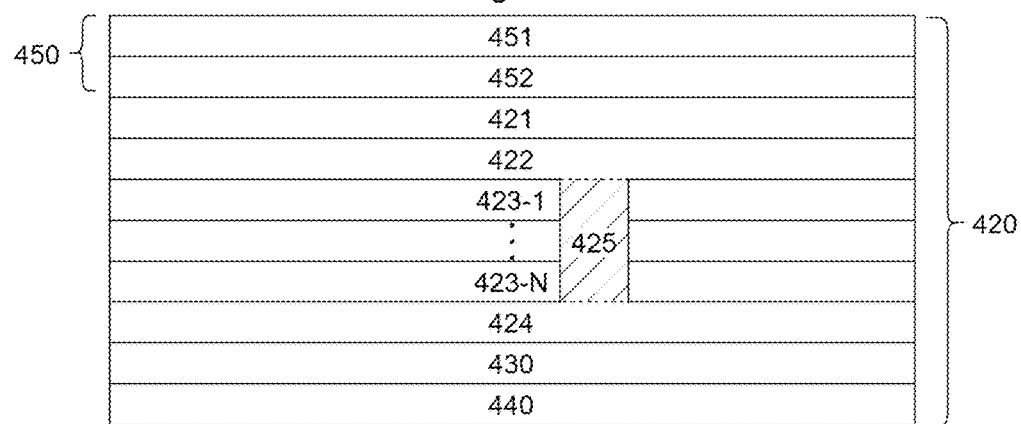
FIG. 4E represents a cross section of one possible pad structure

In one aspect, all the layers from top to the bottom may be configured as depicted in FIG. 4E, wherein the bottom means the part that is facing towards the patient during the therapy. Layer 451 is a top non-sticking part of a sticker 450. Layer 452 is a bottom sticking part (e.g. medical foam tape) of the sticker, which attaches the sticker 451 to the substrate 421 (e.g. PET based) of the pad 420 and/or attaches the sticker 451 to the patient. On the bottom of the substrate 421, there may be a conductive lead 422 that is separated from the active element (e.g. electrode) 424 by N dielectric layers 423-1 to 423-N (where N is a non-negative integer) of the same or different dielectric properties. The active element 424 (e.g. electrode) may be connected with the conductive lead 422 through the hole connection 425 in the dielectric layer(s), hatched in the FIG. 4E. The active element 424 (e.g. electrode), the conductive lead 422 and the hole connection 425 may be printed by the same biocompatible material, such as silver ink, silver-chloride ink, graphite ink or a combination of inks of different conductive materials or may be made by any other know technology of deposition of conductive materials (e.g. lithography). The adhesive layer (e.g. hydrogel) 430 may be deposited on the bottom of the active element 424 (e.g. electrode) and may be covered by a releaser 440 which is removed prior to the attaching of the pad to the patient.

In other aspects, the layers may be different and it may be possible to remove or add more layers to the structure of the pad 420 that is shown in FIG. 4E. For example, as described above, the adhesive layer 430 (and releaser 440) may not be a part of the pad 420, but instead the adhesive layer 430 may be applied directly on the patient skin prior to the coupling of the pad 420 on the patient. In another aspect, the sticker 450 may not be presented on the pad 420. Yet in another aspect the substrate 421 and/or dielectric layer(s) 423-1-423-N may not be part of the pad 420. Moreover, in one aspect, only the active element 424 with conducive lead 422 may be the part of the pad 420. The aspects may be combined together.

Figure 5A:
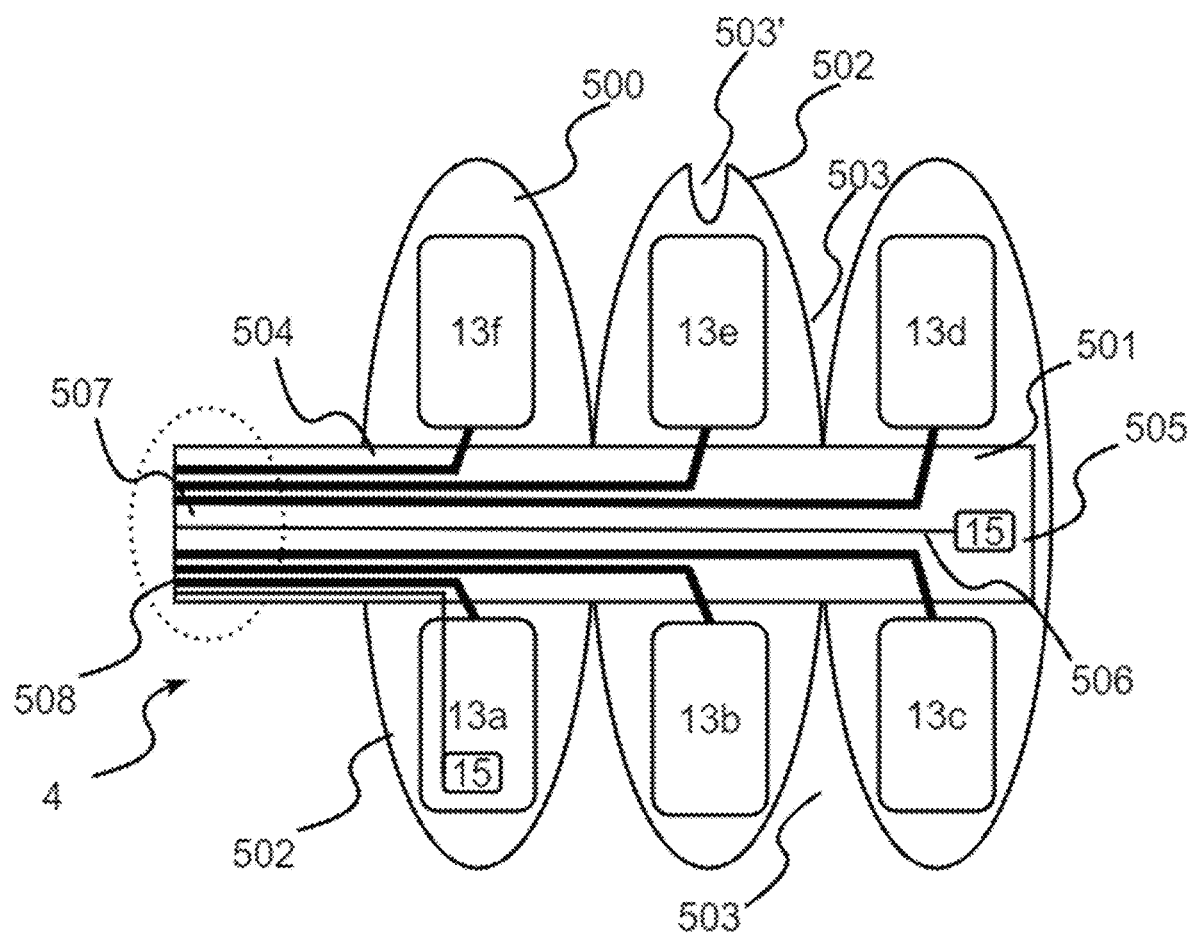
FIG. 5A represents a top view of one variant of the pad.

A pad 4 may include flexible substrate 500, which may comprise a central part 501 and one or more segments 502, which may move at least partially independently from each other as shown in FIG. 5A. The flexible substrate may have a thickness in a range of 1 to 500 μm or in a range of 1 to 350 μm or in a range of 1 to 200 μm or in a range of 5 to 100 μm or in a range of 10 to 75 μm or in a range of 15 to 65 μm. The central part or the segments may include a sensor 15. The number of segments on the pad 4 may be in the range of 1 to 100, or in the range of 1 to 80 or in the range of 1 to 60 or in the range of 2 to 20 or in the range of 3 to 10 or in the range of 4 to 9, wherein each segment may comprise at least one active element 13 (e.g. electrode). The neighboring segments may be at least partially separated by slots 503.

Conventional therapy pads have routinely been made on a single non-segmented substrate which in some cases includes a flexible metal material or a polymeric material with a layer of metallic material deposited thereon.

As seen in FIG. 5A, the proposed segmented pad 4 may be more flexible and may provide a greater amount of contact with the patient than conventional pads routinely used. The substrate 500 of the pad 4 is divided into central part 501 and a plurality of connected segments 502. The plurality of segments 502 may move at least partially independently from one another. The individual segments 502 may be at least partially physically detached from one another by, for example, one or more slots 503, or other open area between neighboring segments 502. The plurality of segments 502 may be physically coupled together by a central part 501 including one or more conductive leads 506. In one aspect, the central part 501 may also include one or more active elements 13 (e.g. electrodes). In another aspect, each active element 13 (e.g. electrode) may be partially deposited in the central part 501 and partially in the corresponding segment 502. In another aspect, some active elements (e.g. electrodes) may be deposited on the central part and some active elements (e.g. electrodes) may be deposited at least partially on the segments.

As shown in FIG. 5A, the slots 503 may extend from the central part 501 of the substrate 500 of the pad 4 proximate to a conductive lead 508 and between neighboring segments 502 to an edge of the substrate 500. Providing for the plurality of segments 502 of the pad 4 to move at least partially independently from one another may facilitate conformance of the pad 4 to curves or contours of a patient's body. A segmented pad 4 as illustrated in FIG. 5A may provide for a greater area, or a greater percentage of the total area, of the pad 4 portion to be in contact with the patient's body than if the pad 4 were formed as a single, non-segmented substrate. In addition, the segments 502 may comprise a perforated gap 503' shown in FIG. 5A, which also provides greater conformance of the pad 4 to curves or contours of a patient's body.

Figure 5B:
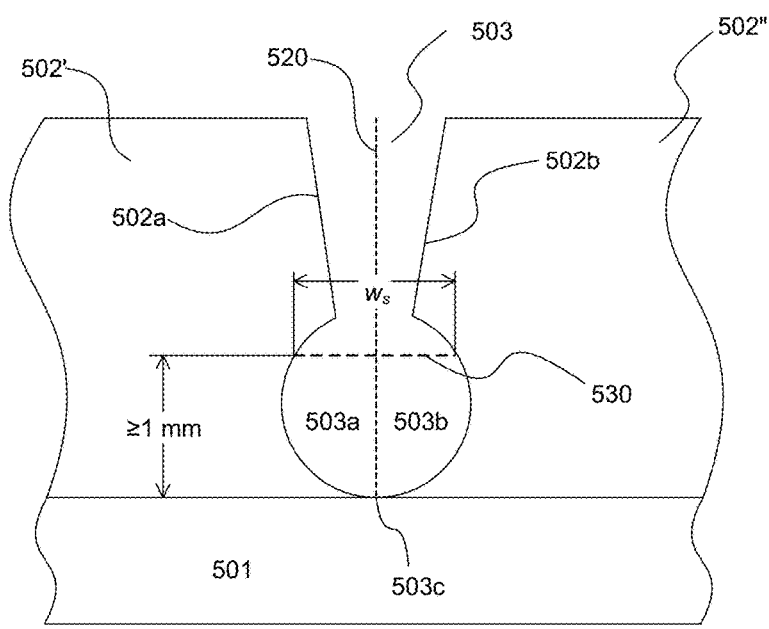
FIG. 5B represents a detail view of one possible arrangement of the slot in the substrate.

The shapes and positions of the segments 502 and/or the slots 503 may be provided in different configurations from those illustrated in FIG. 5A. For example, the segments 502 may include rounded or squared ends or have different dimensional ratios than illustrated. The slots 503 may be curved, squared, triangular, oblong, polygonal or may include re-entrant portions extending between one of the segments 502 and the central part 501. The slots 503 me also be a combination of the shapes mentioned above, e.g. a combination of a triangular slot with the curved end as illustrated in FIG. 5B representing a detail of one possible slot arrangement between two neighboring segments 502' and 502". The slots may be very thin or may be wide, wherein the width of the slot is may be illustrated in one example as follows: First, an imaginary curved or straight line 520 passes through the center of the slot such that it divides the slot into two symmetrical parts 503a and 503b, respectively. The width is then given by a second imaginary line 530 which is perpendicular to the first imaginary line 520 and which would connect the edges of the neighboring segments facing towards the slot 502a and 502b, and where the second imaginary line 530 is at a distance of at least 1 mm away from the beginning of the slot 503c. The beginning of the slot 503c is a point in the slot 503 closest to the central part 501 of the substrate 500 of the pad 4 as seen in FIG. 5B. The first imaginary line 520 is represented by a dashed line in the FIG. 5B and the second imaginary line 530 is represented as a dotted line in FIG. 5B. The width of the slot $w_S$ may be in the range of 100 µm to 10 mm or in the range of 500 µm to 8 mm or in the range of 600 µm to 7 mm or in the range of 800 µm to 5 mm.

Each segment 502 of the substrate 500 may comprise an active element 13 (e.g. electrode) on a portion of, or the entirety of, the segment 502.

The central part 501 may have a proximal end 504 and a distal end 505, wherein the proximal end 504 of the central part 501 may pass or may be connected to the connecting part 507. The central part 501 is connected to the connecting part 507 in the area of a dotted circle in FIG. 5A. Connecting part 507 may comprise a conductive lead 508 for each active element 13 (e.g. electrode) 13a-13f in FIG. 5A, or sensor(s) 15 included in a pad 4, wherein all conductive leads 508 of the connecting part 507 are entering the pad 4 in the proximal end 504 of the central part 501 of the pad 4. Conductive leads 508 are mainly led by the central part 501 until they reach the respective segment and its active element(s) or sensor(s), thus there may be no conductive lead at the distal end 505 of the central part 501 as shown in FIG. 5A. The conductive leads 506 may be led on the top side of the substrate 500 (e.g. the side facing away from the patient) and may be covered by a cover layer (e.g. by synthetic polymer like polyimide). In one aspect, the underside of the pad 4 (the side facing towards the body area of the patient) may also be at least partially covered by the cover layer, mainly in the area where the pad 4 is coupled to the connecting part 507—dotted circle in FIG. 5A, avoiding the active elements 13; to improve mechanical reinforcements of this part of the pad 4, to among other benefits. The cover layer (e.g. polyimide film or foam) may have a thickness in a range of 5 to 50 µm or in a range of 7 to 35 µm or in a range of 10 to 30 µm. In another aspect, the conductive leads 506 may be led on the bottom side of the substrate 500 (e.g. side facing towards the patient) and may be covered by a dielectric layer to prevent the contact of the conductive leads 506 with the patient (e.g. the cover layer of polyimide film or foam).

The connecting part 507 may be flexible or partially elastic. The connecting part may be made of flexible PCB with the cover layer as an isolation layer on the top side and/or the underside of the connecting part 507.

In one aspect, the connecting part 507 may be printed on the substrate, which is made of the same material as the substrate 500 of the pad, and it may be printed (e.g. by metal ink) on the underside of the substrate 500 and covered by the cover layer, so it does not come into a contact with the patient.

The connecting part may have a connector at its ends, which may be rigid. The connector may be one of a USB type A, USB type B, USB type C, USB Micro B, DC power cord, AC power cord, computer power cable, firewire, RJ11, fiber connector, USB 3.0, mini display, pin connector, SMA, DVI, BNC, IDE, PS/2, RCA, display port, PSU, SATA, mSATA, DB9, RJ45, RS232 or any other connector know in the art. The pin connector may have number of pins in a range of 5 to 60 or in a range of 10 to 44 or in a range of 15 to 36 or in a range of 20 to 34. Alternatively, the connector may be made on the flexible PCB with an attached stiffener underneath used to stiffen the connector against out of plane deformation. The stiffener may be made of a non-conductive material including but not limited to plastic or fiberglass. The stiffener may have a thickness in a range of 0.1 to 5 mm or in a range of 0.5 to 2 mm or in a range of 1 to 1.5 mm. The flexible PCB connector may comprise a number of contacts in the range of 5 to 60 or in a range of 10 to 44 or in a range of 15 to 36 or in a range of 20 to 34.

In one aspect, the pad 4, the connecting part 507 and the connector may all be part of the applicator.

The interconnecting block 3 or the main unit 2 may comprise one or more sockets configured to connect the connecting part via the connector on the opposite side to the side where the pad 4 is situated, wherein the one or more sockets are configured to connect an arbitrary pad and/or applicator. Alternatively, the interconnecting block or the main unit may comprise multiple sockets, each socket configured to connect one specific pad and/or applicator for a specific treatment area. The socket may be configured such that it will automatically determine a currently connected pad and/or applicator. The information about the connected pad and/or applicator may be read out from the memory of the pad. Alternatively, the memory may be part of the connector. After the connection, the connector may be linked with the control unit 11 (e.g. CPU). The control unit 11 (e.g. CPU) may provide one or more predetermined treatment protocols to the user via the human machine interface 8 after the detection of the pad in the socket. For example if only a forehead pad is connected, the system may automatically detect this specific pad and propose only a treatment of a forehead of the patient, not allowing the user to set a treatment of other body parts of the patient. Furthermore, the connector may comprise cutouts, grooves, slots, holes and/or notches for locking the connector in the socket. The socket may also comprise a safeguard preventing unintentional connection of the connector in the socket.

In one aspect, the connector may comprise a symbol indicating on which body part the pad and/or the applicator is designated to treat.

In addition, a supplementary connection may be used between the main unit 2 and the connecting part; or between the interconnecting block 3 and the connecting part in order to extend the connection between the main unit 3 and the pad 4 or interconnecting block 3 and the pad 4.

Average pad thickness may be in the range of 10 µm to 2000 µm or in the range of 50 µm to 1000 µm or in the range of 80 µm to 300 µm or in the range of 100 µm to 200 µm.

The apparatus configured in a fractional arrangement may have the active element 13 (e.g. electrode) comprising a matrix formed by active points of defined size. These points are separated by inactive (and therefore untreated) areas that allow faster tissue healing. The surface containing active points may make up from 1 to 99% or from 2 to 90% or from 3 to 80% or from 4 to 75% of the whole active element area (active and inactive area). The active points may have blunt ends at the tissue contact side that do not penetrate the tissue, wherein the surface contacting tissue may have a surface area in the range of 500 $\mu m^2$ to 250 000 $\mu m^2$ or in the range of 1000 $\mu m^2$ to 200 000 $\mu m^2$ or in the range of 200 $\mu m^2$ to 180 000 $\mu m^2$ or in the range of 5000 $\mu m^2$ to 160 000 $\mu m^2$. The blunt end may have a radius of curvature of at least 0.05 mm. A diameter of the surface contacting tissue of one active point may be in the range of 25 $\mu m$ to 1500 $\mu m$ or in the range of 50 $\mu m$ to 1000 $\mu m$ or in the range of 80 $\mu m$ to 800 $\mu m$ or in the range of 100 $\mu m$ to 600 $\mu m$.

Additionally, the device may employ a safety system comprising thermal sensors and a circuit capable of adjusting the therapy parameters based on the measured values. One or more thermal sensors, depending on the number and distribution of active elements 13 (e.g. electrodes), may be integrated onto pad 4 to collect data from different points so as to ensure homogeneity of heating. The data may be collected directly from the treatment area or from the active elements 13 (e.g. electrodes). If uneven heating or overheating is detected, the device may notify the operator and at the same time adjust the therapy parameters to avoid burns to the patient. Treatment parameters of one or more active elements (e.g. electrodes) might be adjusted. The main therapy parameters are power, duty cycle and time period regulating switching between multiple active elements 13 (e.g. electrodes). Therapy may be automatically stopped if the temperature rises above the safe threshold.

Furthermore, impedance measurement may be incorporated in order to monitor proper active element 13 (e.g. electrodes) to skin contact. If the impedance value is outside the allowed limits, the therapy may be automatically suspended and the operator may be informed about potential contact issues. In that case, the active element (e.g. electrode) may act as an impedance sensor itself. The impedance may be measured by one or more active elements (e.g. electrodes) of the pad before, during or after the treatment.

In one aspect, the measurement of the voltage pulses and/or the current pulses and/or phase shift may be used to monitor the course of the electric current therapy. As one non-limiting example, the electric current pulses may have a rectangular shape and the corresponding measured voltage pulses may have a shape depending on the amount of the current passing through the patient. Thus, it may be possible to determine the correct contact of the active element 13 (e.g. electrode) with the patient based on the measurement of the voltage pulses.

Control unit 11 (e.g. CPU) may be incorporated onto the pad 4 itself or it may form a separate part conductively connected to the pad 4. In addition to the control mechanism, control unit 11 (e.g. CPU) may also contain main indicators (e.g. ongoing therapy, actual temperature and active element to skin contact).

Figure 6:
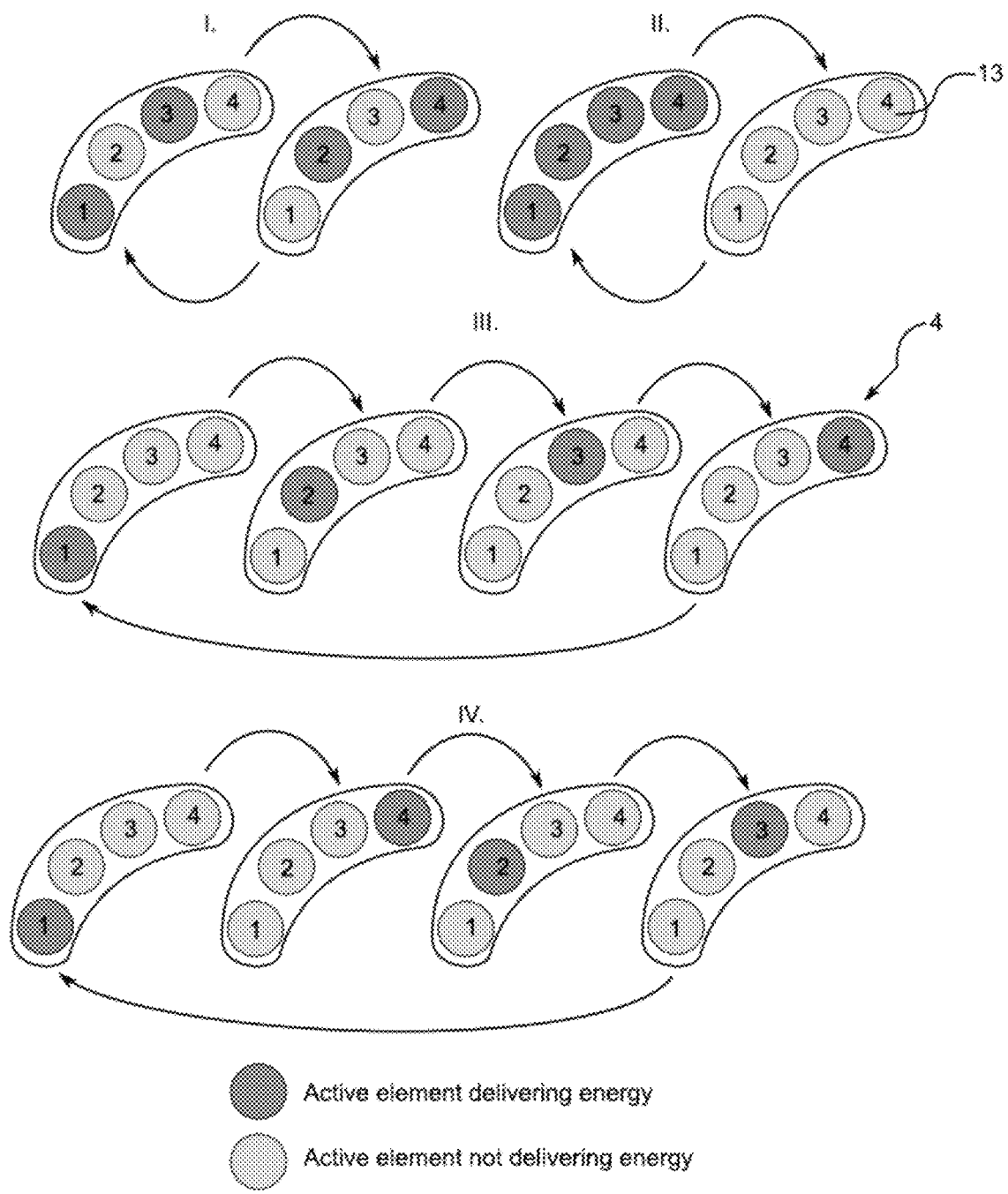
FIG. 6 shows one variant of energy delivery by switching multiple active elements.

FIG. 6 shows some delivery approaches of apparatus for contact therapy.

It is possible to switch between multiple active elements 13 (e.g. electrodes) within the single pad 4 in such a way so that the multiple active elements 13 deliver energy simultaneously, successively or in an overlapping method or any combination thereof. For example, in the case of two active elements: in the simultaneous method, both active elements (e.g. electrodes) are used simultaneously during the time interval e.g., 1-20 s. In the successive method, the first active element (e.g. first electrode) is used during the first time interval e.g., from 1 s to 10 s. The first active element is then stopped and the second active element (e.g. second electrode) is immediately used in a subsequent time interval e.g., from 10 s to 20 s. This successive step may be repeated. In the overlapping method, the first active element (e.g. first electrode) is used during a time interval for e.g., 1-10 s, and the second active element (e.g. second electrode) is used in a second overlapping time interval for e.g., 1-10 s, wherein during the second time interval the first active element and the second active element are overlapping e.g., with total overlapping method time of 0.1-9.9 s. Active elements 13 (e.g. electrodes) may deliver energy sequentially in predefined switching order or randomly as set by operator via human machine interface 8. Schema I in FIG. 6 represents switching between pairs/groups formed of non-adjacent active elements 13 (e.g. electrodes) located within a pad 4. Every pair/group of active elements 13 (e.g. electrodes) is delivering energy for a predefined period of time (dark gray elements in FIG. 6—in schema I elements 1 and 3) while the remaining pairs/groups of active elements 13 (e.g. electrodes) remain inactive in terms of energy delivery (light gray elements in FIG. 6—in schema I elements 2 and 4). After a predefined period of time, energy is delivered by another pair/group of active elements 13 (e.g. electrodes) and the initial active elements (e.g. electrodes) become inactive. This is indicated by arrows in FIG. 6. Switching between pairs/groups of active elements 13 (e.g. electrodes) may continue until a target temperature is reached throughout the entire treatment area or a predefined energy is delivered by all active elements 13 (e.g. electrodes). Schema II in FIG. 6 represents switching of all active elements 13 (e.g. electrodes) within the pad 4 between state ON when active elements (e.g. electrodes) are delivering energy and OFF when they are not delivering energy. The duration of ON and OFF states may vary depending on predefined settings and/or information provided by sensors, e.g. thermal sensors. Schema III in FIG. 6 shows sequential switching of individual active elements 13 (e.g. electrodes) within a pad 4. Each active element 13 (e.g. electrode) is delivering energy for predefined periods of time until a target temperature is reached throughout the entire treatment area or a predefined energy is delivered by all active elements 13 (e.g. electrodes). This sequential switching may be executed in a clockwise or anticlockwise order. Schema IV in FIG. 6 represents a zig-zag switching order during which preferably non-adjacent active elements 13 (e.g. electrodes) deliver energy sequentially until all active elements 13 (e.g. electrodes) within a pad 4 have been switched ON. Each active element 13 (e.g. electrode) delivers energy for a predefined period of time until a target temperature is reached throughout the entire treatment area or a predefined energy is delivered by all active elements (e.g. electrodes).

The control unit (e.g. CPU) may be configured to control the stimulation device and provide treatment by at least one treatment protocol improving of visual appearance. Treatment protocol is set of parameters of the primary electromagnetic energy and the secondary energy ensuring the desired treatment effect. Each pad may be controlled by the control unit (e.g. CPU) to provide same or alternatively different protocol. Pair areas or areas where symmetrical effect is desired may be treated by the same treatment protocol. Each protocol may include one or several sections or steps.

As a non-limiting example: in case of applying the radiofrequency energy by the active elements (e.g. electrodes) one by one as shown in Schema III and IV in FIG. 6, the time when one active element (e.g. electrode) delivers the radiofrequency energy to the tissue of the patient may be in the range of 1 ms to 10 s or in the range of 10 ms to 5 s or in the range of 50 ms to 2 s or in the range of 100 ms to 1500 ms. Two consecutive elements may be switched ON and OFF in successive or overlapping method. Additionally, the delivery of the radiofrequency energy by two consecutive active elements (e.g. electrodes) may be separated by the time of no or low radiofrequency stimulation, such that non of the two consecutive active elements (e.g. electrodes) provides a radiofrequency energy causing heating of the treatment tissue. The time of no or low radiofrequency stimulation may be in the range of 1 μs to 1000 ms, or in the range of 500 μs to 500 ms or in the range of 1 ms to 300 ms or in the range of 10 ms to 250 ms.

In case of the treatment when more than one pad is used, the sequential switching of the active elements (e.g. electrodes) providing radiofrequency treatment may be provided within each pad independently of the other pads or active elements (e.g. electrodes) may deliver energy sequentially through all pads.

As an example for three dependent pads, each with two active elements (e.g. electrodes):

first step—the radiofrequency energy may be provided by active element one in the first pad, wherein other active elements are turned off, second step—the active element two of the first pad is turned on and the rest of the active elements are turned off, third step—the active element one of the second pad is turned on and the rest of the active elements are turned off, fourth step—the active element two of the second pad is turned on and the rest of the active elements are turned off, fifth step—the active element one of the third pad is turned on and the rest of the active elements are turned off, sixth step—the active element two of the third pad is turned on and the rest of the active elements are turned off.

Another non-limiting example may be:

first step—the radiofrequency energy may be provided by active element one in the first pad, wherein other active elements are turned off, second step—the active element one of the second pad is turned on and the rest of the active elements are turned off, third step—the active element one of the third pad is turned on and the rest of the active elements are turned off, fourth step—the active element two of the first pad is turned on and the rest of the active elements are turned off, fifth step—the active element two of the second pad is turned on and the rest of the active elements are turned off, sixth step—the active element two of the third pad is turned on and the rest of the active elements are turned off.

In case that the pads are treating pair areas (e.g. cheeks, thighs or buttocks), where symmetrical effect is desired, the pair pads may be driven by the same protocol at the same time.

An example of treatment protocol for one pad delivering the radiofrequency energy for heating of the patient and the electric current causing the muscle contractions is as follow. The protocol may include a first section where electrodes in one pad may be treated such that the electrodes provide an electric current pulses modulated in an envelope of increasing amplitude modulation (increasing envelope) followed by constant amplitude (rectangle envelope) followed by decreasing amplitude modulation (decreasing envelope), all these three envelopes may create together a trapezoidal amplitude modulation (trapezoidal envelope). The trapezoidal envelope may last 1 to 10 seconds or 1.5 to 7 seconds or 2 to 5 seconds. The increasing, rectangle, or decreasing envelope may last for 0.1 to 5 seconds or 0.1 to 4 seconds or 0.1 to 3 seconds. The increasing and decreasing envelope may last for the same time, thus creating a symmetrical trapezoid envelope. Alternatively, the electric current may be modulated to a sinusoidal envelope or rectangular envelope or triangular envelope. The respective envelopes causing muscle contractions may be separated by time of no or low current stimulation, such that no muscle contraction is achieved or by a radiofrequency energy causing the heating of the tissue. During this time of no muscle contraction, the pressure massage by suction openings may be provided, which may cause the relaxation of the muscles. The first section may be preprogrammed such that electrodes on various places of the pad may be switched in time to provide alternating current pulses wherein some other electrodes in the pad may not provide any alternating current pulses but only RF pulses causing heating of the tissue. All electrodes in the pad may ensure providing (be switched by the switching circuitry 14 that is controled by the control unit 11 to provide) RF pulses for heating the tissue during the section of protocol or protocol, while only a limited amount of the electrodes may provide (be switched by the switching circuitry 14 to provide) alternating currents for muscle contracting during the section of protocol or protocol. The device may be configured such that the first section lasts for 1-5 minutes.

A second section may follow the first section. The second section may be preprogrammed such that different electrodes than the ones used in the first section on various places of the pad may be switched in time to provide alternating current pulses wherein some other electrodes (same or different electrodes than the ones used in the first section) in the pad may not provide any alternating current pulses but only RF pulses causing heating of the tissue.

A third section may follow the second section. The third section may be preprogrammed such that different electrodes than the ones used in the second section on various places of the pad may be switched in time to provide alternating current pulses wherein some other electrodes (same or different electrodes than the ones used in the second section) in the pad may not provide any alternating current pulses but only RF pulses causing heating of the tissue.

An example of a treatment protocol for three dependent pads, e.g. one pad for treatment of the forehead (forehead pad) and two pads for treatment of the left and right cheeks (left and right cheek pad), delivering radiofrequency energy for heating of the patient and electric current causing muscle contractions is as follows: The first pad, e.g. for treatment of the forehead, may have six active elements, e.g. electrodes E1-E6; the second pad, e.g. for treatment of the left cheek, may comprise seven active elements, e.g. electrodes E7-E13; and the third pad, e.g. for treatment of the right cheek, may comprise seven active elements, e.g. electrodes E14-E20. Some electrodes may be configured to provide radiofrequency energy and some electrodes may be configured to provide both radiofrequency energy and electric current.

The radiofrequency energy may be a monopolar radiofrequency energy with a frequency in the range of 100 kHz to 550 MHz or in the range of 250 kHz to 500 MHz or in the range of 350 kHz to 100 MHz or in the range of 350 kHz to 14 MHz. The radiofrequency energy may be delivered with a rectangular envelope which may last for 200 to 3000 ms or for 250 to 2000 ms or for 300 to 1800 ms or for 350 to 1500 ms. Alternatively, the radiofrequency envelope (hereinafter RF envelope) may be modulated to a sinusoidal envelope or triangular envelope or trapezoidal envelope.

The electric current may be a bipolar (biphasic) rectangular AC TENS current with a frequency in the range of 10 Hz to 10 kHz or in the range of 25 Hz to 1 kHz or in the range of 50 to 500 Hz or in the range of 100 to 300 Hz modulated to a trapezoidal envelope, which may last 1 to 10 seconds or 1.5 to 7 seconds or 2 to 5 seconds. An increasing, rectangular, or decreasing envelope of the trapezoidal envelope may last for 0.1 to 5 seconds or 0.1 to 4 seconds or 0.1 to 3 seconds. The increasing and decreasing envelopes may have the same duration, thus creating a symmetrical trapezoidal envelope. Alternatively, the electric current envelope (hereinafter EC envelope) may be modulated to a sinusoidal envelope or rectangular envelope or triangular envelope.

The protocol may have a cycle that includes sections. The number of protocol sections in one cycle may be the same number as the total number of used electrodes within all pads used for the treatment or may be different. The number of sections per pad may be in the range of 1 to 100, or of 1 to 80, or of 1 to 60, or of 2 to 20, or of 3 to 10, or of 4 to 9. The number of sections per cycle may be in the range of 1 to 100, or of 1 to 80, or of 1 to 60, or of 2 to 40, or of 3 to 35, or of 4 to 30. Each protocol section may follow the previous protocol section, e.g. the second section follows the first section. Each protocol section may last for 200 to 3000 ms or for 250 to 2000 ms or for 300 to 1800 ms or for 350 to 1500 ms. The cycle may repeat from 30 to 300, or from 50 to 250, or from 80 to 220, or from 100 to 200, times per treatment. Alternatively, the cycle may repeat from 150 to 600, or from 190 to 550, or from 200 to 520, or from 210 to 500 times per treatment. In one aspect the treatment protocol may repeat the same cycle. In another aspect the treatment protocol may repeat different cycles, wherein the cycles may be different in the number of sections, and/or duration of sections, and/or sequence of activating and/or deactivating the electrodes, and/or parameters set for RF and/or EC envelopes (e.g. shape of envelope, amplitude, frequency, duration and so on), and/or parameters set for radiofrequency and/or parameters of electric current.

An example of a cycle including 20 sections may be as follows:

In the first section, the electrode E2 delivers the RF envelope.

In the second section, the electrode E7 delivers the RF envelope.

In the third section, the electrode E14 delivers the RF envelope.

In the fourth section, the electrode E5 delivers the RF envelope.

In the fifth section, the electrode E8 delivers the RF envelope.

Throughout the first to fifth sections, the electrode pairs E1-E4, E3-E6, E9-E10, E11-E12, E16-E17 and electrode pair E18-E19 deliver the EC envelope causing muscle contractions under the first, second and third pads, e.g. under the forehead pad, the left cheek pad and the right cheek pad.

In the sixth section, the electrode E15 delivers the RF envelope.

In the seventh section, the electrode E13 delivers the RF envelope.

In the eighth section, the electrode E20 delivers the RF envelope.

In the ninth section, the electrode E1 delivers the RF envelope.

In the tenth section, the electrode E3 delivers the RF envelope.

Throughout the sixth to tenth sections, the electrode pairs E9-E10, E11-E12, E16-E17 and electrode pair E18-E19 deliver the EC envelope causing muscle contractions under the second and third pads, e.g. under the left and right cheek pads.

In the eleventh section, the electrode E6 delivers the RF envelope.

In the twelfth section, the electrode E4 delivers the RF envelope.

In the thirteenth section, the electrode E9 delivers the RF envelope.

In the fourteenth section, the electrode E16 delivers the RF envelope.

In the fifteenth section, the electrode E12 delivers the RF envelope.

Throughout the eleventh to fifteenth sections, no electrode pairs deliver the EC envelope, causing the muscles to relax.

In the sixteenth section, the electrode E19 delivers the RF envelope.

In the seventeenth section, the electrode E10 delivers the RF envelope.

In the eighteenth section, the electrode E17 delivers the RF envelope.

In the nineteenth section, the electrode E11 delivers the RF envelope.

In the twentieth section, the electrode E18 delivers the RF envelope.

Throughout the sixteenth to twentieth sections, the electrode pairs E1-E4 and E3-E6 deliver the EC envelope causing muscle contractions under the first pad, e.g. under the forehead pad.

Another example of a treatment protocol for three dependent pads 4 controlled by the control unit 11, e.g. one pad for treatment of the forehead (forehead pad) and two pads for treatment of the left and right cheeks (left and right cheek pad), delivering radiofrequency energy for heating of the patient and electric current causing muscle contractions is as follows: The first pad, e.g. for treatment of the forehead, may have six active elements, e.g. electrodes E1-E6; the second pad, e.g. for treatment of the left cheek, may comprise six active elements, e.g. electrodes E7-E12; and the third pad, e.g. for treatment of the right cheek, may comprise six active elements, e.g. electrodes E13-E18. Some active elements may be configured to provide either electromagnetic energy (e.g. radiofrequency energy) or secondary energy (e.g. electric current), and some active elements may be configured to provide both electromagnetic energy and secondary energy. Alternatively, each active element may be part of one pad 4 (thus using eighteen pads instead of three) or it may be possible to use just the active elements (e.g. electrodes without the substrate of the pad) attached to treated areas. Each protocol section may last for 200 to 3000 ms or for 250 to 2000 ms or for 300 to 1800 ms or for 350 to 1500 ms. The cycle may repeat from 30 to 300, or from 50 to 250, or from 80 to 220, or from 100 to 200, times per treatment/treatment protocol. Alternatively, the cycle may repeat from 150 to 600, or from 190 to 550, or from 200 to 520, or from 210 to 500 times per treatment. In one aspect the treatment protocol may repeat the same cycle. In another aspect the treatment protocol may repeat different cycles, wherein the cycles may be different in the number of sections, and/or duration of sections, and/or sequence of activating and/or deactivating the active elements, and/or parameters set for electromagnetic energy and/or secondary energy (e.g. shape of envelope, amplitude, frequency, duration and so on).

A cycle of the exemplary treatment protocol executed by the control unit 11 may comprise one or more sections from the following list:

In one section, the electrode E10 delivers the RF envelope.

In another section, the electrode E18 delivers the RF envelope.

In another section, the electrode E11 delivers the RF envelope.

In another section, the electrode E15 delivers the RF envelope.

In another section, the electrode E12 delivers the RF envelope.

In another section, the electrode E1 delivers the RF envelope.

In another section, the electrode E14 delivers the RF envelope.

In another section, the electrode E7 delivers the RF envelope.

In another section, the electrode E13 delivers the RF envelope.

In another section, the electrode E8 delivers the RF envelope.

In another section, the electrode E4 delivers the RF envelope.

In another section, the electrode E3 delivers the RF envelope.

In another section, none electrode delivers the RF envelope.

In another section, the electrode E6 delivers the RF envelope.

In another section, the electrode E5 delivers the RF envelope.

In another section, the electrode E16 delivers the RF envelope.

In another section, the electrode E9 delivers the RF envelope.

In another section, the electrode E17 delivers the RF envelope.

In another section, the electrode E2 delivers the RF envelope.

The sections may be arranged one after another in specific order, wherein each section may be included in the cycle one or more times. In one aspect some sections may not be included in the cycle (e.g. a section when none electrode delivers the RF envelope). Each protocol section may last for 200 to 3000 ms or for 250 to 2000 ms or for 300 to 1800 ms or for 350 to 1500 ms and some sections of the cycle may last for time t1, some sections may last for time t2, wherein the t2 is higher than t1. In addition, some sections may last for time t3, which is higher than t1 and t2. For example, the sections may be arranged such that the electrode following the previous electrode is from different pad that the previous electrode.

The cycle may further comprise delivering of electric current (e.g. one or more EC envelopes) by the electrode pairs of the first pad (e.g. E3-E5 and E4-E6) for a time duration of one or more sections in a row, e.g. one to seven sections, two to six sections, three to five sections, or four to five sections in a row, causing muscle contractions under the first pads, e.g. under the forehead pad. Therefore, the electric current may be delivered by the electrode pairs of the first pad (e.g. E3-E5 and E4-E6) for a time duration of 200 ms to 21 s, 250 ms to 12 s, 900 ms to 9 s, 1.4 s to 7.5 s.

The cycle may further comprise delivering of electric current (e.g. one or more EC envelopes) by the electrode pairs of the first, second and third pad (e.g. E3-E5, E4-E6, E9-E11, E10-E12, E15-E17 and E16-E18) for a time duration of one or more sections in a row, e.g. one to seven sections, two to six sections, three to five sections, or four to five sections in a row, causing muscle contractions under the first, second and third pads, e.g. under the forehead pad and left and right cheek pads. Therefore, the electric current may be delivered by the electrode pairs of the first, second and third pad (e.g. E3-E5, E4-E6, E9-E11, E10-E12, E15-E17 and E16-E18) for a time duration of 200 ms to 21 s, 250 ms to 12 s, 900 ms to 9 s, 1.4 s to 7.5 s.

The cycle may further comprise delivering of electric current (e.g. one or more EC envelopes) by the electrode pairs of the second and third pads (e.g. E9-E11, E10-E12, E15-E17 and E16-E18) for a time duration of one or more sections in a row, e.g. one to seven sections, two to six sections, three to five sections, or four to five sections in a row, causing muscle contractions under the second and third pads, e.g. under the left and right cheek pads. Therefore, the electric current may be delivered by the electrode pairs of the second and third pad (e.g E9-E11, E10-E12, E15-E17 and E16-E18) for a time duration of 200 ms to 21 s, 250 ms to 12 s, 900 ms to 9 s, 1.4 s to 7.5 s.

Throughout some sections of the cycle no electrode pairs deliver the EC envelope, causing the muscles to relax.

The treatment protocol may be preprogrammed such that each electrode used during the treatment may deliver the RF envelope once per cycle and some electrode pairs (e.g. E1-E4) may deliver EC envelope twice per cycle. Alternatively, each electrode may deliver the RF envelope 2 to 10, or 2 to 8, or 2 to 5 times per cycle; and some electrode pairs may deliver the EC envelope 1 to 10, or 1 to 8, or 1 to 5 times per cycle.

In one aspect, the treatment protocol may be preprogrammed such that only one electrode delivers the RF envelope per section. In another aspect, 2 to 20, or 2 to 15, or 2 to 10, or 2 to 5, or 2 to 3 electrodes deliver RF envelopes in each section simultaneously, wherein the RF envelopes may be the same or may be different and wherein the electrodes delivering RF envelopes may be from different pads. In another aspect, no RF envelopes may be delivered during at least one section.

The treatment protocol may be preprogrammed such that during a single treatment the RF envelopes are delivered 25 to 300, or 50 to 250, or 80 to 200, or 100 to 180 times by each electrode with an RF pause time between each delivery of the RF envelope. The RF pause time—the time during which the electrode is not providing a radiofrequency energy to the patient between two consecutive deliveries of RF envelopes—may be in the range of 0.5 to 20 s, or of 1 to 15 s, or of 1.5 to 12 s, or of 2 to 10 s.

In one aspect, the radiofrequency energy may be controlled by a control unit (e.g. CPU) in order to provide a constant heating radiofrequency power (CHRP) on each electrode, which means that each electrode provides homogenous heating of the patient. A CHRP setting may be preprogrammed in the treatment protocol for each specific electrode in each specific pad based on the dimensions of the electrode and/or its position in the pad and/or its position on the body area of the patient. In another aspect, the radio frequency power may be controlled by the control unit based on feedback from at least one thermal sensor measuring the temperature of the treated body area and/or the temperature of the electrode providing the radiofrequency energy such, that when the desired temperature is reached, the electrodes are controlled to keep the temperature at this desired level. A typical treatment temperature of the body area under the electrode is in the range of 37.5° C. to 55° C. or in the range of 38° C. to 53° C. or in the range of 39° C. to 52° C. or in the range of 40° C. to 50° C. or in the range of 41° C. to 45° C.

The treatment protocol may be preprogrammed such that during a single treatment the EC envelopes are delivered 25 to 1000, or 50 to 900, or 100 to 750, or 120 to 600, or 150 to 500 times by at least one pair of electrodes with an EC pause time between each delivery of the EC envelope. The EC pause time—the time when the electrode pair is not providing electric current to the patient between two consecutive deliveries of EC envelopes—may be in the range of 0.5 to 20 s, or of 1 to 15 s, or of 1.5 to 12 s, or of 2 to 10 s. Alternatively, the electrode pair may deliver EC envelopes one after another without the EC pause time.

The treatment protocol may be preprogrammed such that during at least one section the active element 13 (e.g. electrode) provides 1 to 900 electric pulses, 2 to 700 electric pulses, 10 to 500 electric pulses, 25 to 400 electric pulses, 50 to 375 electric pulses, or 100 to 200 electric pulses.

In another aspect, radiofrequency energy may be delivered constantly through all electrodes during the whole treatment and only the EC envelopes may be delivered sequentially.

Another non limiting example of a cycle of the treatment protocol executed by the control unit 11 for three pads 4 providing a muscle contractions may be as follows:

The cycle may comprise delivering of electric current (e.g. one or more EC envelopes) by the electrode pairs of the first pad (e.g. E3-E5 and E4-E6) for a time duration of one or more sections in a row, e.g. one to seven sections, two to six sections, three to five sections, or four to five sections in a row, causing muscle contractions under the first pads, e.g. under the forehead pad. Therefore, the electric current may be delivered by the electrode pairs of the first pad (e.g. E3-E5 and E4-E6) for a time duration of 200 ms to 21 s, 250 ms to 12 s, 900 ms to 9 s, 1.4 s to 7.5 s.

The cycle may further comprise delivering of electric current (e.g. one or more EC envelopes) by the electrode pairs of the first, second and third pad (e.g. E3-E5, E4-E6, E9-E11, E10-E12, E15-E17 and E16-E18) for a time duration of one or more sections in a row, e.g. one to seven sections, two to six sections, three to five sections, or four to five sections in a row, causing muscle contractions under the first, second and third pads, e.g. under the forehead pad and left and right cheek pads. Therefore, the electric current may be delivered by the electrode pairs of the first, second and third pad (e.g. E3-E5, E4-E6, E9-E11, E10-E12, E15-E17 and E16-E18) for a time duration of 200 ms to 21 s, 250 ms to 12 s, 900 ms to 9 s, 1.4 s to 7.5 s.

The cycle may further comprise delivering of electric current (e.g. one or more EC envelopes) by the electrode pairs of the second and third pads (e.g. E9-E11, E10-E12, E15-E17 and E16-E18) for a time duration of one or more sections in a row, e.g. one to seven sections, two to six sections, three to five sections, or four to five sections in a row, causing muscle contractions under the second and third pads, e.g. under the left and right cheek pads. Therefore, the electric current may be delivered by the electrode pairs of the second and third pad (e.g E9-E11, E10-E12, E15-E17 and E16-E18) for a time duration of 200 ms to 21 s, 250 ms to 12 s, 900 ms to 9 s, 1.4 s to 7.5 s.

Throughout some sections of the cycle, no electrode pairs deliver the EC envelope, causing the muscles to relax.

In one aspect the treatment protocol may be preprogramed such that each active element 13 (e.g. electrode, coil, heating element, fluid conduit) used during the treatment may provide heating once per cycle and some active elements 13 (e.g. electrode, coil) may provide muscle contractions one or more times per cycle. Alternatively, each active element 13 may provide heating 2 to 10, 2 to 8, or 2 to 5 times per cycle, and some active elements 13 may provide muscle contractions 1 to 10, 1 to 8, or 1 to 5 times per cycle.

In one aspect, the treatment protocol may be preprogrammed such that only one active element 13 provides heating per section (e.g. by radiofrequency energy). In another aspect, 2 to 20, or 2 to 15, or 2 to 10, or 2 to 5, or 2 to 3 active elements 13 provide heating in each section simultaneously, wherein the heating temperature may be the same or may be different. In another aspect, heating may not be provided during at least one section. Each protocol section may last for 200 to 3000 ms or for 250 to 2000 ms or for 300 to 1800 ms or for 350 to 1500 ms and some sections of the cycle may last for time t1, some sections may last for time t2, wherein the t2 is higher than t1. In addition, some sections may last for time t3, which is higher than t1 and t2.

In one aspect, the treatment protocol may be preprogrammed such that during a single treatment the heating (e.g. by radiofrequency energy) is provided 25 to 300, or 50 to 250, or 80 to 200, or 100 to 180 times by one or more active elements 13 with a pause time between each heating. The heating pause time—the time during which non active element 13 is providing a heating of the patient between two consecutive heating—may be in the range of 20 ms to 10 s, or of 50 ms to 5 s, or of 100 ms to 2 s, or of 250 ms to 1 s.

In one aspect, the active elements 13 may be controlled by a control unit (e.g. CPU) to keep the temperature at a desired level. A typical treatment temperature of the body area under the active elements 13 is in the range of 37.5° C. to 55° C. or in the range of 38° C. to 53° C. or in the range of 39° C. to 52° C. or in the range of 40° C. to 50° C. or in the range of 41° C. to 45° C.

The treatment protocol may be preprogrammed such that during a single treatment the muscle contractions are provided 25 to 1000, or 50 to 900, or 100 to 750, or 120 to 600, or 150 to 500 times by at least one active element 13 (e.g. by providing the electric current) or at least one pair of active elements 13 with contraction pause time between each muscle contractions. One contraction may last for a duration in range of 0.1 to 15 seconds or in the range of 0.5 to 12 seconds or of 1 to 10 seconds or in the range of 2 to 8 seconds. The contraction pause time—the time when the at least one active element 13 or at least one pair of active elements 13 is not providing a muscle contraction between two consecutive contractions may be in the range of 0.5 to 20 s, or of 1 to 15 s, or of 1.5 to 12 s, or of 2 to 10 s. Alternatively the at least one active element 13 or at least one pair of active elements 13 may provide contractions one after another without the contraction pause time.

The treatment protocol may be preprogrammed such that during at least one section the active element 13 (e.g. electrode or coil) provides 1 to 900 secondary energy pulses or 2 to 700 secondary energy pulses or 10 to 500 secondary energy pulses or 25 to 400 secondary energy pulses or 50 to 375 secondary energy pulses or 100 to 200 secondary energy pulses. Furthermore, the treatment protocol may be preprogrammed such that during the treatment the active element 13 (e.g. electrode or coil) provides secondary energy envelopes 25 to 1000, or 50 to 900, or 100 to 750, or 120 to 600, or 150 to 500 times.

In another aspect, heating may be provided constantly through all active elements 13 the whole treatment and only the contractions may be provided sequentially, for example, with contraction pause time between each muscle contraction.

Yet in another aspect, the treatment or the cycle may comprise at least one section when no energy/signal is provided to the tissue.

In one aspect, the pad may comprise one or more active elements 13 (e.g. electrode or coil) that provides more than one energy, or the pad may comprise more different active elements 13 (e.g. electrode and coil) that provides more than one energy. For example radiofrequency energy, electric current and magnetic field, or radiofrequency energy, electric current and ultrasound. Alternatively, the pad may be configured to produce more than two therapies, for example, heating of the skin (e.g. by radiofrequency energy), contraction of muscles (e.g. by electric current) and massage/relaxation of the tissue (e.g. by pressure pulses).

A single treatment may last for 1 to 60 min, or for 5 to 45 min, or for 10 to 30 min, or for 15 to 25 min, or for 18 to 23 min based on the number of pads used during the treatment. The number of pads used in single treatment may be 1, 2, 3, 4, 5, 6, 7, 8, 9, 10 or up to 100. The protocol may be preprogrammed such, that the electrodes providing the electric current causing the muscle contractions are switched to provide radiofrequency heating after they produce one, two, three, four or five contractions on maximum.

The respective sections are assembled by the control unit (CPU) in the treatment protocol to provide at least 60-900 contractions or 90-800 contractions, or 150-700 contractions by a single pad per treatment.

In addition, the respective electrode pairs providing electric current to the patient are controlled by the control unit (CPU) to provide at least 50-1000 contractions or 60-900 contractions or 90-800 contractions, or 100-450 contractions per treatment.

Figure 10:
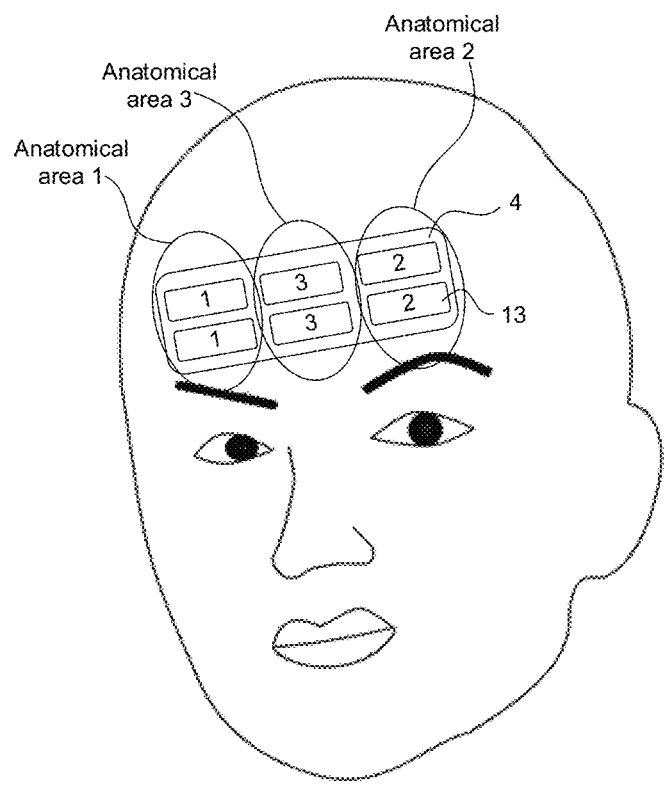
FIG. 10 is an illustration of a forehead pad treatment.

The forehead pad may include a layout of electrodes such that the anatomical area 1 and anatomical area 2 are stimulated by alternating currents which may cause muscle contractions while anatomical area 3 is not stimulated by alternating currents causing muscle contraction as shown in FIG. 10. The control unit (CPU) is configured to provide a treatment protocol energizing by alternating electric currents only those electrodes located in proximity or above the anatomical area 1 and 2; and energizing electrode/electrodes in proximity of or above anatomical area 3 by radiofrequency energy only as shown in FIG. 10. The anatomical area 1 and 2 may comprise the Frontalis muscles and the anatomical area 3 may comprise the center of the Procerus muscle. The forehead pad may also treat the Corrugator supercilii muscle or Orbicularis oculi with radiofrequency energy.

The pad used for a treatment of the cheek (either side of the face below the eye) may include a layout of electrodes such that the anatomical area comprising the Buccinator muscle, the Masseter muscle, the Zygomaticus muscles or the Risorius muscle are stimulated by electrical currents, which may cause muscle contractions, wherein the other anatomical area may be only heated by the radiofrequency energy. A cheek pad may also be used for contraction of the Lavator labii superioris.

On the contrary the pad may be configured such that the layout of electrodes close to the eyes (e.g. body part comprising Orbicularis oculi muscles) or teeth (e.g. body part comprising Orbicularis oris muscles) may not provide energy causing muscle contractions.

The pad used for a treatment of the submentum or submental area may include a layout of electrodes such that the anatomical area comprising the Mylohyoid muscle or the Digastric muscle is stimulated with electrical current, which may cause muscle contractions, wherein the other anatomical area may only be heated by the radiofrequency energy. In one aspect, a submentum pad (pad used for treatment of the submentum) may not provide electric current to an Adam's apple, but may provide heating with radiofrequency energy to the Adam's apple.

The treatment device may be configured such, that in each section or step the impedance sensor provides the information about the contact of the pad or active element (e.g. electrode) with the patient to the control unit (e.g. CPU). The impedance may be measured by the active element (e.g. electrode) itself. The control unit (e.g. CPU) may determine based on the pre-set conditions if the contact of the pad or active element (e.g. electrode) with the patient is sufficient or not. In case of sufficient contact, the control unit (e.g. CPU) may allow the treatment protocol to continue. In case that the contact is inappropriate, the valuated pad or active element (e.g. electrode) is turned off and the treatment protocol continues to consecutive pad or active element (e.g. electrode) or the treatment is terminated. The determination of proper contact of the pad or active element (e.g. electrode) may be displayed on the human machine interface 8.

The impedance measurement may be made at the beginning of the section/step, during the section/step or at the end of the section/step. The impedance measurement and/or the proper contact evaluation may be determined only on the active electrodes for the given section/step or may be made on all electrodes of all pads used during the section/step.

In one aspect, the impedance may be monitored through all active elements (e.g. electrodes) while the therapy is being provided to the patient. The device monitors the impedance between the active element (e.g. electrode) and the skin of the patient while the treatment energy (e.g. radiofrequency or electric current) is being delivered to the patient, analyzes the monitored impedance at two or more different time instances in order to determine a change in the size of the electrode-skin contact area, and if the change in the monitored impedance reaches a pre-determined threshold, alters the stimulation being delivered to the patient or terminates the treatment. The change in the impedance value at a given time may be quantified by an impedance ratio between the impedance value at that time and a baseline impedance, which is a first impedance value from the history of impedance measurement of a given active element (e.g. electrode).

Figure 7:
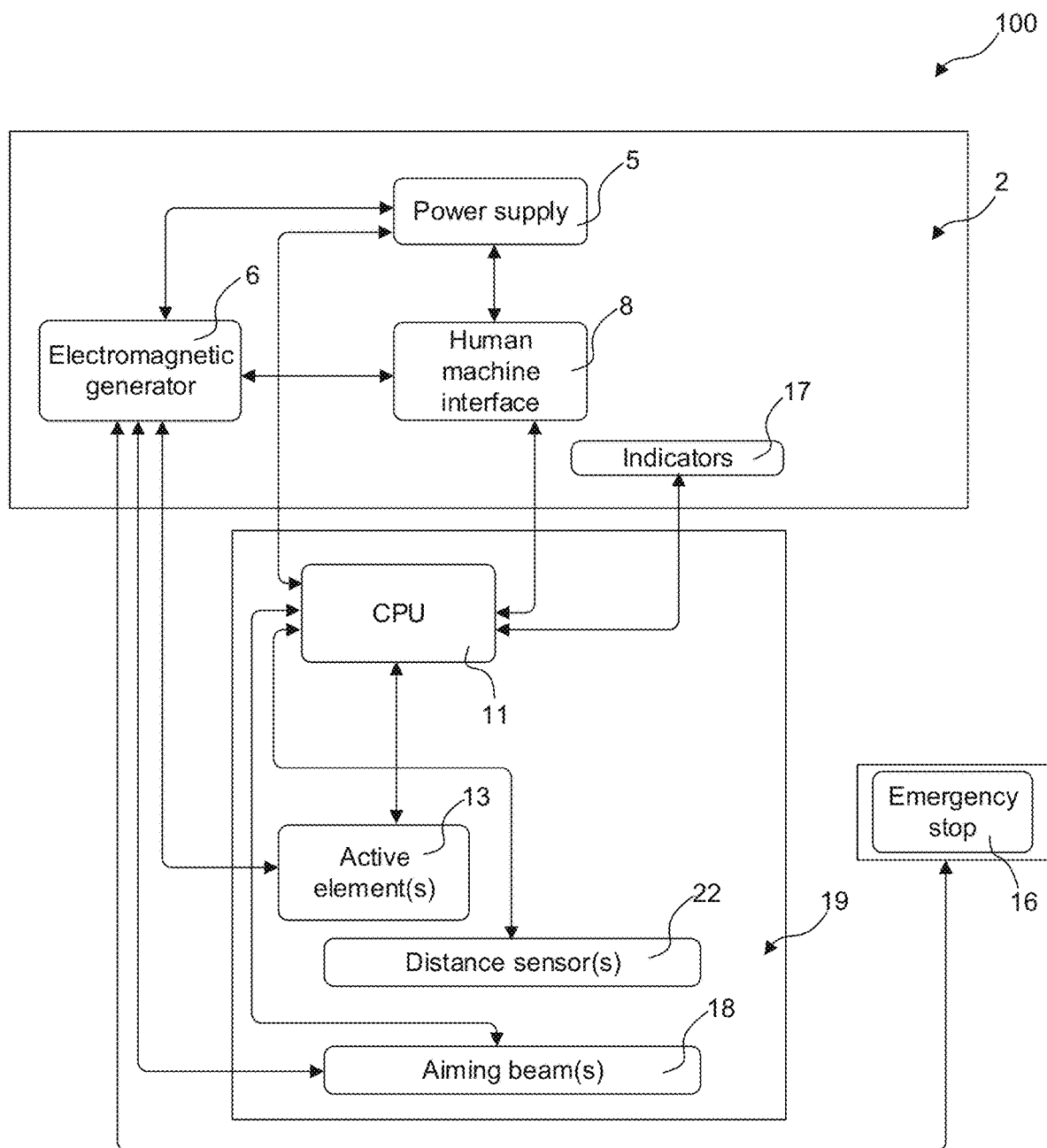
FIG. 7 shows a block diagram of an apparatus for contactless therapy.

The device may further comprise a billing system. The billing system may be based on a reader and an information medium (e.g. card) that has recorded number of therapies. The information medium (e.g. card) may be put into the reader, or may work on a contactless principle, and then the amount of recorded number of therapies is subtracted based on the amount of used pads during the therapy. New information medium (e.g. card) may contain recorded number of therapies in a range of 1 to 100 or in a range of 2 to 80 or in a range of 5 to 50 or in a range of 10 to 40. When the information medium (e.g. card) has no more recorded number of therapies, the user may order a new information medium (e.g. card). If the pads or applicators are disposable, then the information medium may be a part of the new pads or applicators order and the amount of the recorded number of therapies may be equal to the amount of the ordered pads or applicators. For example, if the user of the device orders 30 disposable pads, the amount of recorded therapies on the information medium (e.g. card, which is also a part of the order) is also 30. The reader may be part of the main unit 2, or the interconnecting block 3 or the applicator FIG. 7 and FIG. 8 are discussed together. FIG. 7 shows a block diagram of an apparatus for contactless therapy 100. FIG. 8 is an illustration of an apparatus for contactless therapy 100. Apparatus for contactless therapy 100 may comprise two main blocks: main unit 2 and a delivery head 19 interconnected via fixed or adjustable arm 21.

Main unit 2 may include a primary electromagnetic generator 6 which may generate one or more forms of electromagnetic radiation wherein the electromagnetic radiation may be e.g., in the form of incoherent light or in the form of coherent light (e.g. laser light) of predetermined wavelength. The electromagnetic field may be primarily generated by a laser, laser diode module, LED, flash lamp or incandescent light bulb. The electromagnetic radiation may be such that it may be at least partially absorbed under the surface of the skin of the patient. The wavelength of the applied radiation may be in the range of 100 to 15000 nm or in the range of 200 to 12000 nm or in the range of 300 to 11000 nm or in the range of 400 to 10600 nm or it may be in the form of second, third, fourth, fifth, sixth, seventh or eighth harmonic wavelengths of the above mentioned wavelength ranges. Main unit 2 may further comprise a human machine interface 8 represented by display, buttons, keyboard, touchpad, touch panel or other control members enabling an operator to check and adjust therapy and other device parameters. The power supply 5 located in the main unit may include a transformer, disposable battery, rechargeable battery, power plug or standard power cord. The output power of the power supply 5 may be in the range of 10 W to 600 W, or in the range of 50 W to 500 W, or in the range of 80 W to 450 W. Indicators 17 may provide additional information about the current status of the device independently on human machine interface 8. Indicators 17 may be realized through the display, LEDs, acoustic signals, vibrations or other forms capable of adequate notice.

Delivery head 19 may be interconnected with the main unit via arm 21 which may form the main optical and electrical pathway. Arm 21 may comprise transmission media, for example wires or waveguide, e.g. mirrors or fiber optic cables, for electromagnetic radiation in the form of light or additional electric signals needed for powering the delivery head 19. The control unit (e.g. CPU) 11 controls the primary electromagnetic generator 6 which may generate a continuous electromagnetic energy (CM) or a pulses, having a fluence in the range of 0.1 pJ/cm$^2$ to 1000 J/cm$^2$ or in the range of 0.5 pJ/cm$^2$ to 800 J/cm$^2$ or in the range of 0.8 pJ/cm$^2$ to 700 J/cm$^2$ or in the range of 1 pJ/cm$^2$ to 600 J/cm$^2$ on the output of the electromagnetic generator. The CM mode may be operated for a time interval in the range of 0.1 s to 24 hours or in the range of 0.2 s to 12 hours or in the range of 0.5 s to 6 hours or in the range of 1 s to 3 hours. The pulse duration of the electromagnetic radiation operated in the pulse regime may be in the range of 0.1 fs to 2000 ms or in the range of 0.5 fs to 1500 ms or in the range of 1 fs to 1200 ms or in the range of 1 fs to 1000 ms. Alternatively the pulse duration may be in the range of 0.1 fs to 1000 ns or in the range of 0.5 fs to 800 ns or in the range of 1 fs to 500 ns or in the range of 1 fs to 300 ns. Alternatively, the pulse duration may be in the range of 0.3 to 5000 ps or in the range of 1 to 4000 ps or in the range of 5 to 3500 ps or in the range of 10 to 3000 ps. Or alternatively the pulse duration may be in the range of 0.05 to 2000 ms or in the range of 0.1 to 1500 ms or in the range of 0.5 to 1250 ms or in the range of 1 to 1000 ms. The primary electromagnetic generator 6 in the pulse regime may be operated by control unit (e.g. CPU) 11 in a single shot mode or in a repetition mode or in a burst mode. The frequency of the repetition mode or the burst mode may be in the range of 0.05 to 10 000 Hz or in the range of 0.1 to 5000 Hz or in the range of 0.3 to 2000 Hz or in the range of 0.5 to 1000 Hz. Alternatively the frequency of the repetition mode or the burst mode may be in the range of 0.1 kHz to 200 MHz or in the range of 0.5 kHz to 150 MHz or in the range of 0.8 kHz to 100 MHz or in the range of 1 kHz to 80 MHz. The single shot mode may be configured to generate a single electromagnetic energy of specific parameters (e.g. intensity, duration, etc.) for irradiation of a single treatment area. The repetition mode may be configured to generate an electromagnetic energy, which may have one or more specific parameters (e.g. intensity, duration, etc.), with a repetition rate of the above-mentioned frequency for irradiation of a single treatment area. The burst mode may be configured to generate multiple consecutive electromagnetic energys, which may have variable parameters (e.g. intensity, duration, delay etc.), during one sequence, wherein the sequences are repeated with the above-mentioned frequency and wherein the sequence may include the same or different sets of consecutive electromagnetic energys.

Alternatively, the device may contain more than one primary electromagnetic generator 6 for generation of the same or a different electromagnetic energy, e.g. one primary electromagnetic generator is for generation of an ablative electromagnetic energy and the other is for generation of a non-ablative electromagnetic energy. In this case, it is possible for an operator to select which primary electromagnetic generators may be used for a given treatment or the clinician can choose a required treatment through the human machine interface 8 and the control unit (e.g. CPU) 11 will select which primary electromagnetic generators will be used. It is possible to operate one or more primary electromagnetic generators of the device 100 simultaneously, successively or in an overlapping method. For example in the case of two primary electromagnetic generators: in the simultaneous method, both primary electromagnetic generators are used simultaneously during a time interval e.g., 1-20 ps. In the successive method, the first primary electromagnetic generator is used during the first time interval e.g., from 1 to 10 ps. The first primary electromagnetic generator is then stopped and the second primary electromagnetic generator is immediately used in a subsequent time interval e.g., from 10 to 20 ps. Such a sequence of two or more successive steps may be repeated. In the overlapping method, the first primary electromagnetic generator is used during a time interval, e.g., 1-10 ps, and the second primary electromagnetic generator is used in a second overlapping time interval for e.g., 2-11 ps, wherein during the second time interval the first primary electromagnetic generator and the second primary electromagnetic generator are overlapping e.g., with total overlapping method time for 2-10 ps. In the case of more than two primary electromagnetic generators, the activating and deactivating of the primary electromagnetic generators in a successive or overlap method may be driven by control unit (e.g. CPU) 11 in the order which is suitable for a given treatment, e.g. first activating the pre-heating primary electromagnetic generator, then the ablation primary electromagnetic generator and then the non-ablative primary electromagnetic generator.

The active elements 13 in the delivery head 19 may be in the form of optical elements, which may be represented by one or more optical windows, lenses, mirrors, fibers or diffraction elements. The optical element representing active element 13 may be connected to or may contain primary electromagnetic generator 6 inside the delivery head 19. The optical element may produce one beam of electromagnetic energy, which may provide an energy spot having an energy spot size defined as a surface of tissue irradiated by one beam of light. One optical element may provide one or more energy spots e.g. by splitting one beam into a plurality of beams. The energy spot size may be in the range of 0.001 $cm^2$ to 1000 $cm^2$, or in the range of 0.005 $cm^2$ to 700 $cm^2$, or in the range of 0.01 $cm^2$ to 300 $cm^2$, or in the range of 0.03 $cm^2$ to 80 $cm^2$. Energy spots of different or the same wavelength may be overlaid or may be separated. Two or more beams of light may be applied to the same spot at the same time or with a time gap ranging from 0.1 µs to 30 seconds. Energy spots may be separated by at least 1% of their diameter, and in addition, energy spots may closely follow each other or may be separated by a gap ranging from 0.01 mm to 20 mm or from 0.05 mm to 15 mm or from 0.1 mm to 10 mm.

The control unit (e.g. CPU) may be further responsible for switching between active elements 13 or for moving the active elements 13 within the delivery head 19 so that the electromagnetic radiation may be delivered homogeneously into the whole treatment area marked with aiming beam 18. The rate of switching between active elements 13 may be dependent on the amount of delivered energy, pulse length, etc. and the speed of control unit (e.g. CPU) or other mechanism responsible for switching or moving the active elements 13 (e.g. scanner). Additionally, a device may be configured to switch between multiple active elements 13 in such a way that they deliver energy simultaneously, successively or in an overlapping method. For example, in the case of two active elements: in the simultaneous method, both active elements are used simultaneously during the time interval e.g., 1-20 ps. In the successive method, the first active element is used during the first time interval e.g., from 1 to 10 ps. The first active element is then stopped and the second active element is immediately used in a subsequent time interval e.g., from 10 to 20 ps. This successive step may be repeated. In the overlapping method, the first active element is used during a time interval for e.g., 1-10 ps, and the second active element is used in a second overlapping time interval for e.g., 2-11 ps, wherein during the second time interval the first active element and the second active element are overlapping e.g., with total overlapping method time for 2-10 ps.

The aiming beam 18 has no clinical effect on the treated tissue and may serve as a tool to mark the area to be treated so that the operator knows which exact area will be irradiated and the control unit 11 (e.g. CPU) may set and adjust treatment parameters accordingly. An aiming beam may be generated by a separate electromagnetic generator or by the primary electromagnetic generator 6. Aiming beam 18 may deliver energy at a wavelength in a range of 300-800 nm and may supply energy at a maximum power of 10 mW.

In addition, the pad may contain a control unit 11 (e.g. CPU) driven distance sensor 22 for measuring a distance from active element 13 to the treated point within the treated area marked by aiming beam 18. The measured value may be used by CPU 11 as a parameter for adjusting one or more treatment parameters which may depend on the distance between the active element and a treating point, e.g. fluence. Information from distance sensor 22 may be provided to control unit 11 (e.g. CPU) before every switch/movement of an active element 13 so that the delivered energy will remain the same across the treated area independent of its shape or unevenness.

The patient's skin may be pre-cooled to a selected temperature for a selected duration over at least one treatment portion, the selected temperature and duration for pre-cooling preferably being sufficient to cool the skin to at least a selected temperature below normal body temperature. The skin may be cooled to at least the selected temperature to a depth below the at least one depth for the treatment portions so that the at least one treatment portion is substantially surrounded by cooled skin. The cooling may continue during the application of radiation, wherein the duration of the application of radiation may be greater than the thermal relaxation time of the treatment portions. Cooling may be provided by any known mechanism including water cooling, sprayed coolant, presence of an active solid cooling element (e.g. thermoelectric cooler) or air flow cooling. A cooling element may act as an optical element. Alternatively, a spacer may serve as a cooling element. Cooling may be provided during, before or after the treatment with electromagnetic energy. Cooling before treatment may also provide an environment for sudden heat shock, while cooling after treatment may provide faster regeneration after heat shock. The temperature of the coolant may be in the range of −200° C. to 36° C. The temperature of the cooling element during the treatment may be in the range of −80° C. to 36° C. or −70° C. to 35° C. or −60° C. to 34° C. or −20° C. to 30° C. or 0° C. to 27° C. or 5° C. to 25° C. Further, where the pad is not in contact with the patient's skin, cryogenic spray cooling, gas flow or other non-contact cooling techniques may be utilized. A cooling gel on the skin surface might also be utilized, either in addition to or instead of, one of the cooling techniques indicated above.

Additionally, device 100 may include one or more sensors. The sensor may provide information about at least one physical quantity and its measurement may lead to feedback which may be displayed by human machine interface 8 or indicators 17. The one or more sensors may be used for sensing a variety of physical quantities, including but not limited to the energy of the delivered electromagnetic radiation or backscattered electromagnetic radiation from the skin, impedance of the skin, resistance of the skin, temperature of the treated skin, temperature of the untreated skin, temperature of at least one layer of the skin, water content of the device, the phase angle of delivered or reflected energy, the position of the active elements 13, the position of the delivery element 19, temperature of the cooling media or temperature of the primary electromagnetic generator 6. The sensor may be a temperature, acoustic, vibration, electric, magnetic, flow, positional, optical, imaging, pressure, force, energy flux, impedance, current, Hall or proximity sensor. The sensor may be a capacitive displacement sensor, acoustic proximity sensor, gyroscope, accelerometer, magnetometer, infrared camera or thermographic camera. The sensor may be invasive or contactless. The sensor may be located on the delivery element 19 or in the main unit 2 or may be a part of a distance sensor 22. One sensor may measure more than one physical quantity. For example, a sensor may include a combination of a gyroscope, an accelerometer or a magnetometer. Additionally, the sensor may measure one or more physical quantities of the treated skin or untreated skin.

The thermal sensor measures and monitors the temperature of the treated skin. The temperature can be analyzed by a control unit 11 (e.g. CPU). The thermal sensor may be a contactless sensor (e.g. infrared temperature sensor). The contorol unit 11 (e.g. CPU) may also use algorithms to calculate a temperature below the surface of the skin based on the surface temperature of the skin and one or more additional parameters. A temperature feedback system may control the temperature and based on set or pre-set limits alert the operator in human perceptible form e.g. on the human machine interface 8 or via indicators 17. In a limit temperature condition, the device may be configured to adjust treatment parameters of each active element, e.g. output power, activate cooling or stop the treatment. Human perceptible form may be a sound, alert message shown on human machine interface 8 or indicators 17 or change of color of any part of the device 100.

A resistance sensor may measure the skin resistance, since it may vary for different patients, as well as the humidity—wetness and sweat may influence the resistance and therefore the behavior of the skin in the energy field. Based on the measured skin resistance, the skin impedance may also be calculated.

Information from one or more sensors may be used for generation of a pathway on a convenient model e.g. a model of the human body shown on a display of human machine interface 8. The pathway may illustrate a surface or volume of already treated tissue, presently treated tissue, tissue to be treated, or untreated tissue. A convenient model may show a temperature map of the treated tissue providing information about the already treated tissue or untreated tissue.

The sensor may provide information about the location of bones, inflamed tissue or joints. Such types of tissue may not be targeted by electromagnetic radiation due to the possibility of painful treatment. Bones, joints or inflamed tissue may be detected by any type of sensor such as an imaging sensor (ultrasound sensor, IR sensor), impedance and the like. A detected presence of these tissue types may cause general human perceptible signals or interruption of generation of electromagnetic radiation. Bones may be detected for example by a change of impedance of the tissue or by analysis of reflected electromagnetic radiation.

Furthermore, the device 100 may include an emergency stop button 16 so that the patient can stop the therapy immediately anytime during the treatment.

It may be part of the invention that the method of treatment includes the following steps: preparation of the tissue; positioning the proposed device; selecting or setting up the treatment parameters; and application of the energy. More than one step may be executed simultaneously.

Preparation of the tissue may include removing make-up or cleansing the patient's skin. For higher target temperatures, anesthetics may be applied topically or in an injection.

Positioning the device may include selecting the correct shape of the pad according to the area to be treated and affixing the pad or the neutral electrode to the patient, for example with an adhesive layer, vacuum suction, band or mask, and verifying proper contact with the treated tissue in the case of contact therapy. In the case of contactless therapy, positioning of the device may include adjusting the aiming beam of proposed device so that the device can measure the distance of the active element(s) from the treatment area and adjust the treatment parameters accordingly.

Selecting or setting up the treatment parameters may include adjusting treatment time, power, duty cycle, delivery time and mode (CM or pulsed), active points surface density/size for fractional arrangement and mode of operation. Selecting the mode of operation may mean choosing simultaneous, successive or overlapping methods or selecting the switching order of active elements or groups of active elements or selecting the proper preprogrammed protocol.

Application of the energy may include providing at least one type of energy in the form of RF energy, electric current, ultrasound energy or electromagnetic energy in the form of polychromatic or monochromatic light, or their combination. The energy may be provided from at least one active element into the skin by proposed device. Energy may be delivered and regulated automatically by the control unit (e.g. CPU) according to information from thermal sensors and impedance measurements and, in the case of contactless therapy, distance sensors. All automatic adjustments and potential impacts on the therapy may be indicated on the device display. Either the operator or the patient may suspend therapy at any time during treatment. A typical treatment might have a duration of about 1 to 60 min or 2 to 50 min or 3 to 40 min or 5 to 30 min or 8 to 25 min or 10 to 20 min depending on the treated area and the size and number of active elements located within one or more pads. A typical treatment with 1, 2, 3, 4, 5 or up to 10 pads may have a total duration of about 1 to 60 minutes or 2 to 50 minutes or 3 to 40 minutes 5 to 30 minutes or 8 to 25 minutes or 10 to 20 minutes. A typical treatment with one pad may have a total duration of about 1 to 30 minutes or 2 to 25 minutes or 3 to 22 minutes 5 to 20 minutes or 5 to 15 minutes or 5 to 12 minutes.

In one example, application of energy to the tissue may include providing radiofrequency energy and/or electric current and/or ultrasound energy or any combination of these, from the active elements embedded in the pad, to the skin of the patient. In such embodiment, active elements providing radiofrequency energy are capacitive or resistive RF electrodes and the RF energy may cause heating, coagulation or ablation of the skin. The electric current is provided by the RF electrodes and may cause muscle contractions. Ultrasound energy may be provided through an acoustic window and may rise the temperature in the depth which may suppress the gradient loss of RF energy and thus the desired temperature in a germinal layer may be reach. In addition, the RF electrode may act as an acoustic window for ultrasound energy.

Alternatively, the application of the energy to the tissue may include providing electromagnetic energy in the form of polychromatic or monochromatic light from the active elements into the skin of the patient. In such case, active elements providing the electromagnetic energy may comprise optical elements described in the proposed device. Optical elements may be represented by an optical window, lens, mirror, fiber or electromagnetic field generator, e.g. LED, laser, flash lamp, incandescent light bulb or other light sources known in the state of art. The electromagnetic energy in the form of polychromatic or monochromatic light may entail the heating, coagulation or ablation of the skin in the treated area.

After reaching the required temperature and therapy time the therapy is terminated, the device accessories may be removed and a cleansing of the patient's skin may be provided.

The invention claimed is:

1. An applicator_configured to apply radiofrequency energy and electric current to a patient, the applicator comprising:
    a pad configured to be attached to a body part of a patient, the body part comprising a face, a neck, or a submentum, the pad comprising:
        a flexible substrate, comprising an underside configured to face the patient during a treatment and a top side configured to face away from the patient during the treatment;
        a conductive adhesive layer; and an electrode coupled to the underside of the flexible substrate, the electrode configured to be in contact with the body part through the conductive adhesive layer, wherein a side of the electrode configured to face the body part is at least partially embedded in the conductive adhesive layer and has a surface area in a range of 1 cm$^2$ to 25 cm$^2$, and wherein the conductive adhesive layer is configured to attach the pad to the body part and to attach the electrode to the body part; and a sticker coupled to the top side of the flexible substrate and having a dimension exceeding a corresponding dimension of the pad in a range of 0.1 cm to 10 cm.

2. The applicator_of claim 1, wherein the conductive adhesive layer has an impedance for AC current at 1 kHz in a range of 100 Ohms to 5000 Ohms.

3. The applicator_of claim 1, wherein the conductive adhesive layer has an electric conductivity in a range of 20 mS/m to 200 mS/m.

4. The applicator_of claim 3, wherein the conductive adhesive layer has a thickness in a range of 0.1 mm to 3 mm.

5. The applicator_of claim 1, further comprising a liner configured to cover the conductive adhesive layer, wherein the liner is configured to be removed prior to attachment of the pad to the body part.

6. The applicator_of claim 5, wherein a surface area of the sticker is larger than an area of the pad by a percentage in a range of 0.5% to 50%.

7. The applicator_of claim 6, wherein the sticker has a thickness in a range of 0.05 mm to 3 mm.

8. An applicator for a radiofrequency energy and an electric current treatment of a patient, the applicator comprising:

a pad, comprising:
a flexible substrate comprising an underside configured to face the patient during the treatment;
a flexible electrode coupled to the underside of the flexible substrate;
a conductive adhesive layer coupled to the underside of the flexible substrate and configured to attach the pad and the flexible electrode to a body part of the patient,
wherein the body part comprises a face, a neck, or a submentum; and
a dielectric layer comprising a hole;
a connecting part; and
a rigid connector coupled to the pad via the connecting part,
wherein the connecting part and the pad comprise a conductive lead configured to couple the flexible electrode with the rigid connector,
wherein the dielectric layer is disposed between the conductive lead and the flexible electrode, and
wherein the flexible electrode is connected with the conductive lead through the hole.

9. The applicator of claim 8, further comprising a liner configured to cover the conductive adhesive layer and configured to be removed prior to attachment of the pad to the body part.

10. The applicator of claim 8, wherein the flexible substrate has a thickness in a range of 1 μm to 500 μm.

11. The applicator of claim 8, wherein the conductive lead, the hole, and the flexible electrode comprise the same conductive material.

12. The applicator of claim 8, wherein the rigid connector is configured to connect the applicator with a main unit.

13. The applicator of claim 8, wherein the flexible electrode is configured to apply the radiofrequency energy to the body part in order to cause heating of a skin of the body part and configured to apply the electric current to the body part in order to cause a muscle contraction of a muscle within the body part.

14. A pad for a radiofrequency energy and an electric current treatment of a patient, the pad comprising:

a substrate, comprising:
a central part;
a first segment coupled to the central part; and
a second segment coupled to the central part, wherein the first segment and the second segment are divided by a slot,
wherein the first segment is configured to move at least partially independently from the second segment, and
wherein an underside of the first segment and an underside of the second segment are configured to face a body part of the patient during the treatment;
a first electrode coupled partially to the underside of the first segment;
a second electrode coupled partially to the underside of the second segment; and
an adhesive layer coupled to a side of the first electrode and a side of the second electrode configured to face toward the body part,
wherein the adhesive layer is configured to attach the pad with the first electrode and the second electrode to the body part,
wherein the body part comprises a face, a neck, or a submentum, and
wherein the thickness of the pad is in a range of 10 μm to 2000 μm.

15. The pad of claim 14, wherein a hardness of the pad is in a shore range of OO10 to D80.

16. The pad of claim 15, wherein a width of the slot is in a range of 100 μm to 10 mm.

17. The pad of claim 14, wherein the first electrode comprises one or more apertures, cutouts, or protrusions.

18. The pad of claim 17, wherein the first electrode comprises: a frame made of conductive material;
grid lines made of conductive material disposed inside the frame; and
non-conductive apertures disposed inside the frame and defined by the frame and the grid lines.

19. The pad of claim 18, wherein the frame has a thickness in a range of 0.1 mm to 5 mm.

20. The pad of claim 18, wherein the grid lines have a thickness in a range of 0.01 mm to 2.3 mm.

21. The pad of claim 18, wherein a distance between two closest parallel grid lines is in a range of 0.01 mm to 8 mm.

22. An applicator_configured to apply radiofrequency energy and electric current to a patient, the applicator comprising:

a pad having a surface area in a range of 0.1 cm$^2$ to 150 cm$^2$, and configured to be attached to a body part of a patient, the body part comprising a face, a neck, or a submentum, and the pad comprising:
a flexible substrate comprising an underside configured to face the patient during the treatment and a top side configured to face away from the patient during the treatment;
a conductive adhesive layer coupled to the underside of the flexible substrate; and
a plurality of electrodes coupled to the underside of the flexible substrate, each electrode configured to be in electrical contact with the body part through the conductive adhesive layer; and a sticker coupled to the top side of the flexible substrate, comprising:
- an underside configured to face the patient during the treatment; and
- a sticking layer disposed on the underside of the sticker and configured to attach the pad to the body part,
- wherein the sticker has a shape with a dimension exceeding a corresponding dimension of the pad in a range of 0.1 cm to 10 cm.

23. The applicator of claim 22, wherein the pad is configured to be attached to a forehead of the patient, and
   wherein the plurality of electrodes comprises a left edge electrode positioned on a left side of the pad, a right edge electrode positioned on a right side of the pad, and a middle electrode positioned between the left edge electrode and the right edge electrode.

24. The applicator_of claim 23, wherein the left edge electrode is spaced from the right edge electrode at a distance in a range of 2 cm to 8 cm.

25. The applicator_of claim 23, wherein the left edge electrode and right edge electrode are configured to be attached over a frontalis muscle, and
   wherein a side of each electrode from the plurality of electrodes configured to face the patient during the treatment has a surface area in a range of 2 $cm^2$ to 6.5 $cm^2$.

26. The applicator of claim 22, wherein the pad is configured to be attached on a left cheek or a right cheek of the patient, and
   wherein the plurality of electrodes comprises between 1 to 10 electrodes.

27. The applicator of claim 26, wherein a surface area of a side of each electrode from the plurality of electrodes configured to face the body part is in a range of 2 $cm^2$ to 8 $cm^2$,
   wherein neighbouring electrodes from the plurality of electrodes are distant from each other in a range of 0.5 mm to 5 mm, and
   wherein the plurality of electrodes is configured to be positioned over at least one of Platysma, Depressor, Buccinator, Risorius, Zygomaticus, Masseter, or Lavator labii superior muscles.

28. The applicator_of claim 22, further comprising:
   a connector comprising a plurality of contacts; and
   a connecting part comprising a plurality of conductive leads and configured to couple the pad with the connector,
   wherein the plurality of conductive leads is configured to couple the plurality of electrodes with the plurality of contacts.

* * * * *

UNITED STATES PATENT AND TRADEMARK OFFICE
CERTIFICATE OF CORRECTION

PATENT NO. : 11,633,596 B2
APPLICATION NO. : 17/941777
DATED : April 25, 2023
INVENTOR(S) : Schwarz et al.

Page 1 of 1

It is certified that error appears in the above-identified patent and that said Letters Patent is hereby corrected as shown below:

In the Claims

In Column 58, Claim 1, Line 57, delete "applicator_configured" and insert -- applicator configured --, therefor.

In Column 59, Claim 2, Line 15, delete "applicator_of" and insert -- applicator of --, therefor.

In Column 59, Claim 3, Line 18, delete "applicator_of" and insert -- applicator of --, therefor.

In Column 59, Claim 4, Line 21, delete "applicator_of" and insert -- applicator of --, therefor.

In Column 59, Claim 5, Line 23, delete "applicator_of" and insert -- applicator of --, therefor.

In Column 59, Claim 6, Line 27, delete "applicator_of" and insert -- applicator of --, therefor.

In Column 59, Claim 7, Line 30, delete "applicator_of" and insert -- applicator of --, therefor.

In Column 60, Claim 22, Line 53, delete "applicator_configured" and insert -- applicator configured --, therefor.

In Column 61, Claim 24, Line 18, delete "applicator_of" and insert -- applicator of --, therefor.

In Column 61, Claim 25, Line 21, delete "applicator_of" and insert -- applicator of --, therefor.

In Column 62, Claim 27, Lines 16-17, delete "Lavator labii superior" and insert -- Levator labii superioris --, therefor.

In Column 62, Claim 28, Line 18, delete "applicator_of" and insert -- applicator of --, therefor.

Signed and Sealed this
Twenty-seventh Day of June, 2023

Katherine Kelly Vidal
*Director of the United States Patent and Trademark Office*